United States Patent
Freier

(10) Patent No.: US 12,043,831 B2
(45) Date of Patent: *Jul. 23, 2024

(54) MODULATION OF ALPHA SYNUCLEIN EXPRESSION

(71) Applicant: Ionis Pharmaceuticals, Inc., Carlsbad, CA (US)

(72) Inventor: Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/024,359

(22) Filed: Sep. 17, 2020

(65) Prior Publication Data

US 2021/0087562 A1    Mar. 25, 2021

Related U.S. Application Data

(63) Continuation of application No. 15/490,667, filed on Apr. 18, 2017, now Pat. No. 10,815,480, which is a continuation of application No. 13/988,296, filed as application No. PCT/US2011/061245 on Nov. 17, 2011, now Pat. No. 9,663,783.

(60) Provisional application No. 61/414,848, filed on Nov. 17, 2010.

(51) Int. Cl.
C12N 15/113    (2010.01)

(52) U.S. Cl.
CPC ........ *C12N 15/113* (2013.01); *C12N 2310/11* (2013.01); *C12N 2310/315* (2013.01); *C12N 2310/323* (2013.01); *C12N 2310/3231* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,102,785 A | 4/1992 | Livak et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |

(Continued)

FOREIGN PATENT DOCUMENTS

| | | |
|---|---|---|
| EP | 2444494 | 9/2016 |
| EP | 2920304 | 3/2019 |

(Continued)

OTHER PUBLICATIONS

Abeliovich et al., "Mice lacking alpha-synuclein display functional deficits in the nigrostriatal dopamine system." Neuron (2000) 25(1):239-252.
Albaek et al., "Analogues of a Locked Nucleic Acid with Three-Carbon 2',4'-Linkages: Synthesis by Ring-Closing Metathesis and Influence on Nucleic Acid Duplex Stability and Structure" J. Org. Chem. (2006) 71:7731-7740.
Altmann et al., "Second-generation antisense oligonucleotides: structure-activity relationships and the design of improved signal-transduction inhibitors" Biochem. Soc. Trans. (1996) 24:630-637.
Altmann et al., "Second Generation of Antisense Oligonucleotides: From Nuclease Resistance to Biological Efficacy in Animals" Chimia (1996) 50(4):168-176.

(Continued)

*Primary Examiner* — Ekaterina Poliakova-Georgantas
(74) *Attorney, Agent, or Firm* — Banner & Witcoff, LTD

(57) ABSTRACT

Disclosed herein are antisense compounds and methods for decreasing alpha-synuclein mRNA and protein expression. Also disclosed herein are methods for treating, preventing, and ameliorating neurodegenerative diseases in an individual in need thereof.

26 Claims, No Drawings

Specification includes a Sequence Listing.

(56) References Cited

U.S. PATENT DOCUMENTS

| | | |
|---|---|---|
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,277,640 B1 | 8/2001 | Bennett et al. |
| 6,300,319 B1 | 10/2001 | Manoharan |
| 6,426,220 B1 | 7/2002 | Bennett et al. |
| 6,455,308 B1 | 9/2002 | Freier et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,833,361 B2 | 12/2004 | Hong et al. |
| 7,015,315 B1 | 3/2006 | Cook et al. |
| 7,034,133 B2 | 4/2006 | Wengel et al. |
| 7,053,207 B2 | 5/2006 | Wengel |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,579,458 B2 | 8/2009 | Khvorova et al. |
| 7,595,306 B2 | 9/2009 | Bumcrot |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,750,141 B2 | 7/2010 | Crooke et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,389,487 B2 | 3/2013 | Bohn et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 9,663,783 B2 | 5/2017 | Freier |
| 10,815,480 B2 | 10/2020 | Freier |
| 11,230,712 B2 | 1/2022 | Kordasiewicz et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2004/0219671 A1 | 11/2004 | McSwiggen |
| 2004/0226056 A1 | 11/2004 | Roch et al. |
| 2005/0064548 A1 | 3/2005 | Lindquist et al. |
| 2005/0130923 A1 | 6/2005 | Bhat et al. |
| 2005/0137155 A1 | 6/2005 | McSwiggen et al. |

(56) References Cited

U.S. PATENT DOCUMENTS

| | | |
|---|---|---|
| 2006/0148740 A1 | 7/2006 | Platenburg |
| 2007/0031844 A1 | 2/2007 | Khvorova et al. |
| 2007/0161595 A1 | 7/2007 | Bumcrot et al. |
| 2007/0192879 A1 | 8/2007 | Yoshimoto et al. |
| 2007/0225209 A1 | 9/2007 | Roch et al. |
| 2007/0287831 A1 | 12/2007 | Seth et al. |
| 2008/0003570 A1 | 1/2008 | Rogers et al. |
| 2008/0039418 A1 | 2/2008 | Freier |
| 2008/0039618 A1 | 2/2008 | Allerson et al. |
| 2008/0139799 A1* | 6/2008 | Khvorova ............ C12N 15/113 536/24.5 |
| 2009/0092981 A1 | 4/2009 | Swayze et al. |
| 2009/0176729 A1 | 7/2009 | Tan |
| 2010/0190837 A1 | 7/2010 | Migawa et al. |
| 2010/0197762 A1 | 8/2010 | Swayze et al. |
| 2010/0204306 A1 | 8/2010 | Tan |
| 2011/0054005 A1 | 3/2011 | Naito et al. |
| 2012/0129912 A1 | 5/2012 | Mouradian et al. |
| 2012/0322991 A1 | 12/2012 | Montefeltro et al. |
| 2013/0130378 A1 | 5/2013 | Manoharan et al. |
| 2014/0005252 A1 | 1/2014 | Bennett et al. |
| 2014/0107330 A1 | 4/2014 | Freier et al. |
| 2014/0120158 A1 | 5/2014 | Montefeltro et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2017/0039316 A1* | 2/2017 | Fofanov ................ G16B 30/10 |
| 2017/0044526 A1 | 2/2017 | Wan et al. |
| 2017/0275621 A1 | 9/2017 | Butler et al. |
| 2018/0073022 A1 | 3/2018 | Freier |
| 2020/0040061 A1 | 2/2020 | Lundberg et al. |
| 2020/0392494 A1 | 12/2020 | Kordasiewicz et al. |
| 2022/0315923 A1 | 10/2022 | Kordasiewicz et al. |

FOREIGN PATENT DOCUMENTS

| | | | |
|---|---|---|---|
| EP | 2922955 | 3/2019 | |
| EP | 3189141 | 6/2020 | |
| EP | 2982755 | 10/2020 | |
| EP | 2585596 | 12/2020 | |
| EP | 3194597 | 6/2021 | |
| WO | WO-9914226 A2 * | 3/1999 | ............ A61P 31/12 |
| WO | WO 2001/057277 | 8/2001 | |
| WO | WO 2001/077384 | 10/2001 | |
| WO | WO 2003/004602 | 1/2003 | |
| WO | WO 2004/106356 | 12/2004 | |
| WO | WO 2005/021570 | 3/2005 | |
| WO | WO 2005/097817 | 10/2005 | |
| WO | WO 2006/034348 | 3/2006 | |
| WO | WO 2007/134181 | 11/2007 | |
| WO | WO 2007/135426 | 11/2007 | |
| WO | WO 2008/101157 | 8/2008 | |
| WO | WO 2008/109509 | 9/2008 | |
| WO | WO 2008/150729 | 12/2008 | |
| WO | WO 2008/154401 | 12/2008 | |
| WO | WO 2009/006478 | 1/2009 | |
| WO | WO 2009/079399 | 6/2009 | |
| WO | WO 2011/131693 | 10/2011 | |
| WO | WO-2012/027713 A2 | 3/2012 | |
| WO | WO 2012/068405 | 5/2012 | |
| WO | WO 2014/064257 | 5/2014 | |
| WO | WO 2017/119463 | 7/2017 | |
| WO | WO 2019/164562 | 8/2019 | |

OTHER PUBLICATIONS

Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16(7-9):917-926.

Altschul et al., "Basic Local Alignment Search Tool" J. Mol. Biol. (1990) 215:403-410.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Burre et al., "Alpha-synuclein promotes SNARE-complex assembly in vivo and in vitro." Science (2010) 329(5999): 1663-1667.

Cabin et al., "Synaptic vesicle depletion correlates with attenuated synaptic responses to prolonged repetitive stimulation in mice lacking alpha-synuclein." J. Neurosci. (2002) 22(20):8797-8807.

Chan et al. "Antisense Oligonucleotides: from design to therapeutic application" Clinical and Experimental Pharmacology and Physiology (2006) 533-540.

Chen et al., "RNA interference targeting a-synuclein attenuates methamphetamine-induced neurotoxicity in SH-SY5Y cells" Brain Research (2013) 1521: 59-67.

Chiasson et al., "The application of antisense oligonucleotide technology to the brain: some pitfalls." Cellular and Molecular Neurobiology (1994) 14(5):507-521.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Clayton et al., "Synucleins in synaptic plasticity and neurodegenerative disorders" J. Neurosci. (1999) 58(1):120-129.

Conway et al., "Kinetic Stabilization of the α-Synuclein Protofibril by a Dopamine-α-Synuclein Adduct" Science (2001) 294(5545):1346-1349.

Crooke et al., "Basic Principles of Antisense Therapeutics" Antisense Research and Application (1998) Chapter 1:1-50.

Davidson et al., "Stabilization of alpha-synuclein secondary structure upon binding to synthetic membranes." J. Biol. Chem. (1998) 273(16):9443-9449.

Elayadi et al., "Application of PNA and LNA oligomers to chemotherapy" Curr. Opinions Invens. Drugs (2001) 2:558-561.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

European Search Report for application EP 11840796.4 dated Dec. 4, 2014.

Fleming et al., "Early and Progressive Sensorimotor Anomalies in Mice Overexpressing Wild-Type Human α-Synuclein" J. Neurosci. (2004) 24(42):9434-9440.

Fleming et al., "Olfactory deficits in mice overexpressing human wildtype alpha-synuclein." Eur. J. Neurosci. (2008) 28(2):247-256.

Fountaine et al., "RNA Interference-Mediated Knockdown of a-Synuclein Protects Human Dopaminergic Neuroblastoma Cells From MPP+ Toxicity and Reduces Dopamine Transport" Journal of Neuroscience Research (2007) 85:351-363.

Freier et al., "The ups and downs of nucleic acid duplex stability: structure-stability studies on chemically-modified DNA: RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Gautschi et al., "Activity of a Novel bcl-2/bcl-xL-Bispecific Antisense Oligonucleotide Against Tumors of Diverse Histologic Origins" Gautschi et al. (2001) 93(6):463-471.

GenBank Accession No. NM_000345.3.

Gorbatyuk et al., "In Vivo RNAi-Mediated α-Synuclein Silencing Induces Nigrostriatal Degeneration" Mol. Ther. (2010) 18(8): 1450-1457.

Henry et al., "Chemically Modified Oligonucleotides Exhibit Decreased Immune Stimulation in Mice" J Pharma Exp Ther (2000) 468-479.

International Search Report for application PCT/US11/61245 dated May 18, 2012.

(56) References Cited

OTHER PUBLICATIONS

International Search Report for application PCT/US18/60097 dated Sep. 30, 2019.
Iwai et al., "The precursor protein of non-A beta component of Alzheimer's disease amyloid is a presynaptic protein of the central nervous system." Neuron (1995) 14(2):467-475.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.
Kramer et al., "Presynaptic-Synuclein Aggregates, Not Lewy Bodies, Cause Neurodegeneration in Dementia with Lewy Bodies" J. Neurosci. (2007) 27(6):1405-1410.
Kumar et al., "The First Analogues of LNA (Locked Nucleic Acids): Phosphorothioate-LNA and 2'-Thio-LNA" Bioorg. Med. Chem. Lett. (1998) 8:2219-2222.
Lee et al., "Membrane-bound α-Synuclein Has a High Aggregation Propensity and the Ability to Seed the Aggregation of the Cytosolic Form" J. Biol. Chem. (2002) 277(1):671-678.
Leumann, "DNA Analogues: From Supramolecular Principles to Biological Properties" Bioorganic & Medicinal Chemistry (2002) 10:841-854.
Lewis et al., "In vivo silencing of alpha-synuclein using naked siRNA" Mol Neurodegener (2008) 3:19.
Liu et al., "a-Synuclein produces a long-lasting increase in neurotransmitter release" The EMBO Journal (2004) 23:4506-4516.
Maguire-Zeiss et al., "a-Synuclein: A therapeutic target for Parkinson's disease?" Pharmacol Res (2008) 58: 271-280.
Maher et al., "Comparative hybrid arrest by tandem antisense oligodeoxyribonucleotides or oligodeoxyribonucleoside methylphosphonates in a cell-free system" Nucl. Acids. Res. (1988) 16(8):3341-3358.
Marti et al., "Clinical Overview of the Synucleinopathies" Movement Disorders (2003) 18(6):S21-S27.
Martin, "Ein neuer Zugang zu 2'-O-Alkylribonucleosiden und Eigenschaften deren Oligonucleotide" Helv. Chim. Acta (1995) 78:486-504.
McCormack et al., "a-Synuclein Suppression by Targeted Small Interfering RNA in the Primate Substantia Nigra" PLoS One (2010) 5(8):e12122.
Monti et al., "Alpha-synuclein protects cerebellar granule neurons against 6-hydroxydopamine-induced death" J. of Neurochemistry (2007) 103:518-530.
Murphy et al., "Synucleins Are Developmentally Expressed, and a-Synuclein Regulates the Size of the Presynaptic Vesicular Pool in Primary Hippocampal Neurons" The Journal of Neuroscience (2000) 20(9):3214-3220.
New England Biolabs 1998/99 Catalog (cover page and pp. 121 and 284).
Orum et al., "Locked nucleic acids: A promising molecular family for gene-function analysis and antisense drug development" Curr. Opinion Mol. Ther. (2001) 3:239-243.
Reynolds et al., "Rational siRNA design for RNA interference" Nature Biotechnology (2004) 22(3):326-330.
Rockenstein et al., "Differential neuropathological alterations in transgenic mice expressing alpha-synuclein from the platelet-derived growth factor and Thy-1 promoters." J. Neurosci. Res. (2002) 68(5):568-578.
Sanghvi et al., "Heterocyclic Base Modifications in Nucleic Acids and Their Applications in Antisense Oligonucleotides" Antisense Research and Applications (1993) pp. 273-288.
Sapru et al., "Silencing of human α-synuclein in vitro and in rat brain using lentiviral-mediated RNAi" Exp. Neurol. (2006) 198:382-390.
Schulz-Schaeffer, "The synaptic pathology of α-synuclein aggregation in dementia with Lewy bodies, Parkinson's disease and Parkinson's disease dementia" Acta Neuropathologica (2010) 120(2):131-143.
Seema et al., "In-silico analysis for RNA-interference mechanism of α-synuclein to treat Parkinson's disease" Int. J. Bioinformatics Research and App (2013) 9(6) Abstract Only.
Sibley et al., "Identification of Allele-Specific RNAi Effectors Targeting Genetic Forms of Parkinson's Disease" PLOS One (2011) 6(10): e26194.
Singh et al., "LNA (locked nucleic acids): synthesis and high-affinity nucleic acid recognition" Chem. Commun. (1998) 4:455-456.
Singh et al., "Synthesis of 2'-Amino-LNA: A Novel Conformationally Restricted High-Affinity Oligonucleotide Analogue with a Handle" J. Org. Chem. (1998) 63:10035-10039.
Souza et al., "Chaperone-like activity of synucleins." FEBS Lett. (2000) 474(1):116-119.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26): 8362-8379.
Uversky, "Neuropathology, biochemistry, and biophysics of alpha-synuclein aggregation." J. Neurochem. (2007) 103(1): 17-37.
Vickers et al., "Efficient reduction of target RNAs by small interfering RNA and RNase H-dependent antisense agents. A comparative analysis" J Biol Chem (2003) 278(9): 7108-7118.
Vickers et al., "Effects of RNA secondary stucture on cellular antisense activity" Nucleic Acids Res (2000) 1340-1347.
Wahlestedt et al., "Potent and nontoxic antisense oligonucleotides containing locked nucleic acids" PNAS (2000) 97:5633-5638.
Woolf et al., "Specificity of antisense oligonucleotides in vivo" PNAS (1992) 89:7305-7309.
Xu et al., "Effective Small Interfering RNAs and Phosphorothioate Antisense DNAs have different preferences for Target Sites in the Luciferase mRNAs" Biochemical and Biophysical Research Communications (2003) 306: 712-717.
Yoshida, "Multiple system atrophy: alpha-synuclein and neuronal degeneration." Neuropathology (2007) 27(5):484-493.
Zhang et al., "PowerBLAST: A New Network BLAST Application for Interactive or Automated Sequence Analysis and Annotation" Genome Res. (1997) 7:649-656.
Zhou e al., "Fine Tuning of Electrostatics around the Internucleotidic Phosphate through Incorporation of Modified 2',4'-Carhocyclic-LNAs and -ENAs Leads to Significant Modulation of Antisense Properties" J. Org. Chem. (2009) 74:118-134.
Bennett et al., "RNA Targeting Therapeutics: Molecular Mechanisms of Antisense Oligonucleotides as a Therapeutic Platform" Annu Rev Pharmacol Toxicol (2010) 50: 259-293.
Crooke et al., "Antisense technology: A review" J Biol Chem (2021) 296: 1-39.
Gassmann et al., "Quantifying Western blots: Pitfalls of densitometry" Electrophoresis (2009) 30: 1845-1855.
Martinez et al., "Single-Stranded Antisense siRNAs Guide Target RNA Cleavage in RNAi" Cell (2002) 110: 563-574.
Possin "Visual Spatial Cognition in Neurodegenerative Disease" Neurocase (2010) 16: 466-487.
Sewell et al., "Phase I Trial of ISIS 104838, a 2'-Methoxyethyl Modified Antisense Oligonucleotide Targeting Tumor Necrosis Factor-α" The Journal of Pharmacology and Experimental Therapeutics (2002) 303: 1334-1343.
Singh et al., "A Review of Antisense Thereapeutic Interventions for Molecular Biological Targets in Various Diseases" International J of Pharmacol (2011) 7: 294-315.

* cited by examiner

SEQUENCE LISTING

<160> NUMBER OF SEQ ID NOS: 143

<210> SEQ ID NO 1
<211> LENGTH: 3215
<212> TYPE: DNA

<213> ORGANISM: Homo sapiens

<400> SEQUENCE: 1

| | | | | | |
|---|---|---|---|---|---|
| aggagaagga | gaaggaggag | gactaggagg | aggaggacgg | cgacgaccag | aagggccca | 60 |
| agagaggggg | cgagcgaccg | agcgccgcga | cgcggaagtg | aggtgcgtgc | gggctgcagc | 120 |
| gcagaccccg | gcccggcccc | tccgagagcg | tcctgggcgc | tccctcacgc | cttgccttca | 180 |
| agccttctgc | ctttccaccc | tcgtgagcgg | agaactggga | gtggccattc | gacgacagtg | 240 |
| tggtgtaaag | gaattcatta | gccatggatg | tattcatgaa | aggactttca | aaggccaagg | 300 |
| agggagttgt | ggctgctgct | gagaaaacca | acagggtgt | ggcagaagca | gcaggaaaga | 360 |
| caaaagaggg | tgttctctat | gtaggctcca | aaaccaagga | gggagtggtg | catggtgtgg | 420 |
| caacagtggc | tgagaagacc | aaagagcaag | tgacaaatgt | tggaggagca | gtggtgacgg | 480 |
| gtgtgacagc | agtagcccag | aagacagtgg | agggagcagg | gagcattgca | gcagccactg | 540 |
| gctttgtcaa | aaaggaccag | ttgggcaaga | atgaagaagg | agccccacag | gaaggaattc | 600 |
| tggaagatat | gcctgtggat | cctgacaatg | aggcttatga | aatgccttct | gaggaagggt | 660 |
| atcaagacta | cgaacctgaa | gcctaagaaa | tatctttgct | cccagtttct | tgagatctgc | 720 |
| tgacagatgt | tccatcctgt | acaagtgctc | agttccaatg | tgcccagtca | tgacatttct | 780 |
| caaagttttt | acagtgtatc | tcgaagtctt | ccatcagcag | tgattgaagt | atctgtacct | 840 |
| gcccccactc | agcatttcgg | tgcttccctt | tcactgaagt | gaatacatgg | tagcagggtc | 900 |
| tttgtgtgct | gtggattttg | tggcttcaat | ctacgatgtt | aaaacaaatt | aaaaacacct | 960 |
| aagtgactac | cacttatttc | taaatcctca | ctatttttt | gttgctgttg | ttcagaagtt | 1020 |
| gttagtgatt | tgctatcata | tattataaga | ttttaggtg | tcttttaatg | atactgtcta | 1080 |
| agaataatga | cgtattgtga | aatttgttaa | tatatataat | acttaaaaat | atgtgagcat | 1140 |
| gaaactatgc | acctataaat | actaaatatg | aaattttacc | attttgcgat | gtgttttatt | 1200 |
| cacttgtgtt | tgtatataaa | tggtgagaat | taaaataaaa | cgttatctca | ttgcaaaaat | 1260 |
| atttttatttt | tatcccatct | cactttaata | ataaaaatca | tgcttataag | caacatgaat | 1320 |
| taagaactga | cacaaaggac | aaaaatataa | agttattaat | agccatttga | agaaggagga | 1380 |
| attttagaag | aggtagagaa | aatggaacat | taaccctaca | ctcggaattc | cctgaagcaa | 1440 |
| cactgccaga | agtgtgtttt | ggtatgcact | ggttccttaa | gtggctgtga | ttaattattg | 1500 |
| aaagtggggt | gttgaagacc | ccaactacta | ttgtagagtg | gtctatttct | cccttcaatc | 1560 |
| ctgtcaatgt | ttgctttacg | tattttgggg | aactgttgtt | tgatgtgtat | gtgtttataa | 1620 |
| ttgttataca | tttttaattg | agccttttat | taacatatat | tgttattttt | gtctcgaaat | 1680 |
| aattttttag | ttaaaatcta | ttttgtctga | tattggtgtg | aatgctgtac | ctttctgaca | 1740 |
| ataaataata | ttcgaccatg | aataaaaaaa | aaaaaaagt | gggttccgg | gaactaagca | 1800 |
| gtgtagaaga | tgattttgac | tacaccctcc | ttagagagcc | ataagacaca | ttagcacata | 1860 |
| ttagcacatt | caaggctctg | agagaatgtg | gttaactttg | tttaactcag | cattcctcac | 1920 |
| ttttttttt | taatcatcag | aaattctctc | tctctctctc | tcttttttctc | tcgctctctt | 1980 |
| tttttttttt | ttttacagg | aaatgccttt | aaacatcgtt | ggaactacca | gagtcacctt | 2040 |
| aaaggagatc | aattctctag | actgataaaa | atttcatggc | ctcctttaaa | tgttgccaaa | 2100 |
| tatatgaatt | ctaggatttt | tccttaggaa | aggtttttct | ctttcaggga | agatctatta | 2160 |
| actccccatg | ggtgctgaaa | ataaacttga | tggtgaaaaa | ctctgtataa | attaatttaa | 2220 |
| aaattatttg | gtttctctttt | ttaattattc | tggggcatag | tcatttctaa | aagtcactag | 2280 |

| | | | | |
|---|---|---|---|---|
| tagaaagtat | aatttcaaga | cagaatattc | tagacatgct | agcagtttat atgtattcat | 2340 |
| gagtaatgtg | atatatattg | ggcgctggtg | aggaaggaag | gaggaatgag tgactataag | 2400 |
| gatggttacc | atagaaactt | ccttttttac | ctaattgaag | agagactact acagagtgct | 2460 |
| aagctgcatg | tgtcatctta | cactagagag | aaatggtaag | tttcttgttt tatttaagtt | 2520 |
| atgtttaagc | aaggaaagga | tttgttattg | aacagtatat | ttcaggaagg ttagaaagtg | 2580 |
| gcggttagga | tatattttaa | atctacctaa | agcagcatat | tttaaaaatt taaaagtatt | 2640 |
| ggtattaaat | taagaaatag | aggacagaac | tagactgata | gcagtgacct agaacaattt | 2700 |
| gagattagga | aagttgtgac | catgaattta | aggatttatg | tggatacaaa ttctccttta | 2760 |
| aagtgtttct | tcccttaata | tttatctgac | ggtaattttt | gagcagtgaa ttactttata | 2820 |
| tatcttaata | gttatttggg | gaccaaacac | ttaaacaaaa | agttctttaa gtcatataag | 2880 |
| ccttttcagg | aagcttgtct | catattcact | cccgagacat | tcacctgcca agtggcctga | 2940 |
| ggatcaatcc | agtcctaggt | ttattttgca | gacttacatt | ctcccaagtt attcagcctc | 3000 |
| atatgactcc | acggtcggct | ttaccaaaac | agttcagagt | gcactttggc acacaattgg | 3060 |
| gaacagaaca | atctaatgtg | tggtttggta | ttccaagtgg | ggtcttttc agaatctctg | 3120 |
| cactagtgtg | agatgcaaac | atgtttcctc | atctttctgg | cttatccagt atgtagctat | 3180 |
| ttgtgacata | ataaatatat | acatatatga | aaata | | 3215 |

<210> SEQ ID NO 2
<211> LENGTH: 115001
<212> TYPE: DNA
<213> ORGANISM: Homo sapiens

<400> SEQUENCE: 2

| | | | | |
|---|---|---|---|---|
| agaatcatct | aatgatattg | tggttatttt | taaacagtcc | ttaaattttg tggatgcata | 60 |
| ctgaatgttt | acagctgaaa | agatatatat | aaagcttgaa | tttggtaaaa aaaaaaaaaa | 120 |
| aagagggagg | attggtagtg | ataaagtgag | tggacttatg | gatgagacat gatcagccat | 180 |
| gcattgaaaa | aatgtaaaag | ttggatgatc | ttcacatgag | agtcctttat tctgtctact | 240 |
| tttgcatatg | tttgaatatt | tcccataaca | aaaagttgaa | aatagagtga tcacatgagt | 300 |
| taatctccta | atttacaaaa | aagaaaactg | gaaacagaag | gagaacaaaa cttgttcaag | 360 |
| gtctcaaagc | cagacagcaa | actagctccc | aagtccaacc | ttcttgctct ggtcctaagc | 420 |
| aaacaaaaaa | tattaatatg | agctactgca | ttaaggaaag | tctgcttttc caaagggcag | 480 |
| accaatagtt | caaggaagag | tttaaataat | aaatatttgt | gatcttactt tcatgctttt | 540 |
| ctatttcca | ctgaacacat | atgcattatc | ttctatatgt | cttttatgta taatcatttg | 600 |
| cttcctgttc | cttgtggttt | taagttgtt | ttgtatgttt | aaatttgatt ttactcaaat | 660 |
| ttcagaaccc | aaattagcgc | aagaatcaga | caaagcataa | cttctataa atataaaaac | 720 |
| aattaaaaaa | aaaacataca | gcaaaaacga | gttgttgttt | ccccctcct cttccagtgc | 780 |
| ttaactaatc | ttccgaatcc | aggcacagaa | agcaaaggct | ttctgctagt gggaggagct | 840 |
| tgcttctcca | ttctggtgtg | atccaggaac | agctgtcttc | cagctctgaa agaggtgaaa | 900 |
| atgtgttaag | cgatgcaaaa | attgtcttga | agttcgcgtg | tgtatgtctg tgtgcatgtg | 960 |
| cgtgtggtgg | gtgggggag | agaaaagggg | gtgtcaattc | tgagggcaac gagaatcaga | 1020 |
| agtcagaaag | gtgagtggtg | tgtagcatct | ccctttcaga | agggctgaa gaagaaattg | 1080 |
| gatatgatgg | tccggtaggc | taaatcacgc | tggatttgtc | tcccagataa agggaggtct | 1140 |

```
gcaaagtaag tcccatttct agagcgaaaa gccttaggac cgcttgtttt agacggctgg    1200
ggaatattta ttccttgttc cactgatggg aaaatcagcg tctggcaggc gctgattggt    1260
ggaaaggaaa atggtgatag tggcgtggaa agaggatttg ctgagccttc tcctgcctcc    1320
tcaacctgtg actcttcctt agtagtctcc ctttcaccct caggacccct tccggctctt    1380
cctagattaa gagcaaacga aaaccttgaa gatatttgaa ctaaagcgac ccctaacgtt    1440
gtaacctgtg accgtgatta aatttcagcg atgcgagggc aaagcgctct cggcggtgcg    1500
gtgtgagcca cctcccggcg ctgcctgtct cctccagcag ctccccaagg gataggctct    1560
gcccttggtg gtcgaccctc aggccctcgg ctctcccagg gcgactctga cgaggggtag    1620
ggggtggtcc ccgggaggac ccagaggaaa ggcggggaca agaagggagg ggaaggggaa    1680
agaggaagag gcatcatccc tagcccaacc gctcccgatc tccacaagag tgctcgtgac    1740
cctaaactta acgtgaggcg caaaagcgcc cccactttcc cgccttgcgc ggccaggcag    1800
gcggctggag ttgatggctc accccgcgcc ccctgcccca tccccatccg agatagggac    1860
gaggagcacg ctgcagggaa agcagcgagc gccgggagag gggcgggcag aagcgctgac    1920
aaatcagcgg tggggcgga gagccgagga gaaggagaag gaggaggact aggaggagga    1980
ggacggcgac gaccagaagg ggcccaagag aggggcgag cgaccgagcg ccgcgacgcg    2040
gaagtgaggt gcgtgcgggc tgcagcgcag accccggccc ggcccctccg agagcgtcct    2100
gggcgctccc tcacgccttg ccttcaagcc ttctgccttt ccaccctcgt gagcggagaa    2160
ctgggagtgg ccattcgacg acaggttagc gggtttgcct cccactcccc cagcctcgcg    2220
tcgccggctc acagcggcct cctctgggga cagtccccc cgggtgccgc ctccgcccctt    2280 cctgtgcgct ccttttcctt cttctttcct attaaatatt atttgggaat tgtttaaatt    2340
ttttttttaa aaaagagag aggcggggag gagtcggagt tgtggagaag cagagggact    2400
caggtaagta cctgtggatc taaacgggcg tctttggaaa tcctggagaa cgccggatgg    2460
gagacgaatg gtcgtgggca ccgggagggg gtggtgctgc catgaggacc cgctgggcca    2520
ggtctctggg aggtgagtac ttgtcccttt ggggagccta aggaaagaga cttgacctgg    2580 cttttcgtcct gcttctgata ttcccttctc cacaagggct gagagattag gctgcttctc    2640
cgggatccgc ttttccccgg gaaacgcgag gatgctccat ggagcgtgag catccaactt    2700
ttctctcaca taaatctgt ctgcccgctc tcttggtttt tctctgtaaa gtaagcaagc    2760
tgcgtttggc aaataatgaa atggaagtgc aaggaggcca agtcaacagg tggtaacggg    2820
ttaacaagtg ctggcgcggg gtccgctagg gtggaggctg agaacgcccc ctcgggtggc    2880
tggcgcgggg ttggagacgg cccgcgagtg tgagcggcgc ctgctcaggg tagatagctg    2940
agggcggggg tggatgttgg atggattaga accatcacac ttgggcctgc tgtttgcctg    3000
agtttgaacc acaccccgag tgagcagtta gttctgttgc ctacgccttt ccaccatcaa    3060
cctgttagcc ttcttctggg attcatgtta aggatacccc tgaccctaag cctccagctt    3120
ccatgcttct aactcatact gttaccctt agaccccggg aatttaaaaa agggttaat    3180 cttttcatgc aactccactt ctgaaatgca gtaataacaa ctcagaggat tcatcctaat    3240
ccgtggttag gtggctagac ttttactagc caagatggat gggagatgct aaattttaa    3300 tgccagagct aaaaatgtct gctttgtcca atggttaaat gagtgtacac ttaaaagagt    3360
ctcacacttt ggagggtttc tcatgatttt tcagtgtttt tgtttatttt ttccccgaaa    3420
gttctcattc aaagtgtatt ttatgttttc cagtgtggtg taaggaatt cattagccat    3480 ggatgtattc atgaaaggac tttcaaaggc caaggaggga gttgtggctg ctgctgagaa    3540
```

```
aaccaaacag ggtgtggcag aagcagcagg aaagacaaaa gagggtgttc tctatgtagg    3600
taggtaaacc ccaaatgtca gtttggtgct tgttcatgag tgatgggtta ggataatcaa    3660
tactctaaat gctggtagtt ctctctcttg attcattttt gcatcattgc ttgtcaaaaa    3720
ggtggactga gtcagaggta tgtgtaggta ggtgaatgtg aacgtgtgta tttgagctaa    3780
tagtaaaaaa tgcgactgtt tgcttttcca gattttaat tttgccctaa tatttatgac     3840
tttttaaaaa tgaatgtttc tgtacctaca taattctatt tcagagaaca gttttaaaaa    3900
ctcatagtct tttaaaaaat aatcaagaat attcttaaga atcaaaatca ttgatggatc    3960
tgtgatttct tttaccatca tgaaaaatgt ttgtcaattt taatccattc tgattttaa     4020 aatatgactt tgatatgccc ctgtgatgtg tataaagaga cctatttgtg gccctaaaat    4080
ggaaagaaca gattagtctt tgatagagtt acttcatgtg atcatttggt ctctgtgaac    4140
actgaggaca gagaaaagtg cttgagggct gctactaatc tctcagaaac atttgtatag    4200
ttcatccatc aaatgacaca catactaaaa gaataaagaa attgatgctt attacctact    4260
tgttcctaaa gttccacctt ggggtataca cccaaactct gactctcttt tctgtaactt    4320
gaactgtatt caattgagtg ttattttaca aaccactttg aattccttgg aaagaatag     4380 acacacactc tcatccacag gcatagacac acacactcaa cacagacaca ttgcccattc    4440
ttcctctctt ctttctcctc tgagcttttt cacattctct ggtggcaact atagcagtaa    4500
gagtcacagg atgaacagtc aggtggagga tgaccacatt gagttgccta gctgaaacat    4560
gtgctccgtc tatgtctgca aagtgaaaga aagctacact atctcttcaa catagatcag    4620 tggggaaat tttatacttg ggatgattta tatgaatgca tctcatcaaa gttcacaaca     4680
catttttttt tcagtttttt attttcagtt tttagagtca gggccttgct ctgtcgccca    4740
ggctggactg cagtgatgct atcatagctc actgcatcct gaattcctg ggctcaagtc     4800 atgcccccac ctcagcctcc tgagtagcca ggattatagg catgtgccac tgcctcatta    4860
tttagacttt tcttatgttg acttaatctt cccacaaatc ttcaattaaa ttactttttt    4920
tctaccttaa aacatatttt cagaaagtca ttgaaatagg gtgttacaag aggaaaaat     4980 tgatgagtta attttaaata ttttatgaag tgtgaattat acctttttag atggaatttg    5040
gaatactgaa tcagtgacat gcagtttatc aatatctttc cgtttgtcct cagatttcca    5100
agttctgcaa gcacaagttt cttgtactta gttacctttt aactgttcat tgaaatcatt    5160
ttcaatgtct ctcatggcat ttaacacata gcacattcta taaattttt attggttaca    5220 ttctgagttc taattgagag ttgaacttac acacagaatt taagataaaa aatgaccatg    5280
tgaagacaca atagtatagt ccagggattg gcaaatttt gggtaaggaa tcagatagca     5340 cgtatttaa gccatgagat ctatgtcttg gccaggtgcc gtggctcagg tctttaatcc     5400
cagcactttg agagcccgag gctggtggat cacttgagcc caggggttg agaccagcct      5460 gggccacatg tgaaaccct gtgtctacaa acaacgcaaa aattagccgg gtatggtagc     5520
atgcatgtgt attgccagct acccaggagg ctgaggtagg aggatggctt gagccataca    5580
gctcactgca gaggttgcag tgagctgaga tcgagccact gcactccagc ctgggtggca    5640
gagtgatacc ctgtctaaaa aaaagaaaaa aaatctatg tctcaattct gctgttgaag     5700
tgtgaaggta gtcataaaca ataactagtg tggctgtgtc ccaataaaac ttcatttatc    5760
aaaacaggtg gtgggctgga attgtcttgt atgttgtagc ttgctgacta ctgatagagt    5820
ggaaagaaca tgcactaatc acacaaacca aagttttagt tgagactaca tcacttatca    5880
```

```
cctttagggt cttggggaag cgtacttaac atctctgagc atcacttccc tgattagtaa    5940
aaaatatgat ttagaaaact gcaactacct tgcagttttt gtgggaatgt cataataaga    6000
caggacatat gaataattga gcacactttt atatatagga accatggtta ttattatcaa    6060
ataaactctc caacggaata attactttgc caacacgttt tccatttatt cttttatcct    6120
tcattacata actagtttga aagattggag gcgaccaaag accattttat aatttcactt    6180
atggctgaag atgtttggta gaagcctcat aagaaaagta atctcattcc tttataagaa    6240
tatactttta acaactactt tttaactcat tgaagaacta ccttaatgat cagtgttatt    6300
tttatgggtt ttgttccctc cattttttgtt atctgcgtac accaattttc aatcaacata    6360
cttcaattta atagacaaaa atttcttcaa atgactcaga aattaattag atctaaatcc    6420
aaaagcagaa agatttaatt atctttatat aatgctcagt aatataaatg caataaatac    6480
aagaaaatga tgatctttga gtgtcttcca atgccactct gctcaataag cagcagtggc    6540
catcagtgaa attgatagca aattctcaag tcaaaatgtg cttcacctca ctaagctgac    6600
aaagtcaaca taacatgcac aacagggata actgagttct caaaactctc aggtattact    6660
tctgaccttc ttctccactc tgtgctcttt tgaggttggg aagacaagat agggtgtgtg    6720
tgggacacct ccgctcaggg aagccatcag ctctggtgtc cctacagcat ttataccttg    6780
ctagtcacat aaccacttgg cacctatttt gtaggtgtac gttatcaatt acagattact    6840
cataaattaa aggctaacca tcaattacag attattagta aataattatg acctcaaaga    6900
acaactgatt ggtttgatac atggtaacct tatgaggact ctcatttatc tcgttttttt    6960
aagttatata cctatctctt tggggttgca ctacaaaaat ataaaatatg ttgcataaga    7020
tatttataaa aaataattaa ttataagttc taatggtgtg gtttagtggc attcttttt     7080 ttttcttttt ttctgagata gggtctcaat ctgtcatttc actccaggct gaagtgcagt    7140
ggtgtgatct cggctcactg caacctccgc ctcctgggtt caagttattc tcctgactca    7200
gcctcctgag tagctgaaat tacaggcatg caccaccatg cccggctaat ttttgtattt    7260
ttagtagaga tggggtttca ccatgttagc caggatggtc tcgaactcct gatctcatca    7320
tccccgacct cggcctccca aaatgctggg attacaggcg tgagccattg cacccggcct    7380
agtggcattc ttttttaaaa ataaatttaa ttgtgtatat ttagggtatg caacatgatg    7440
ctatcagata cattagacac taaaaaatta ctatattgaa gcaaattaat atattcataa    7500
tctctcatag ttaccttttt tgttgttttt gtggcaaggg cagctaaaat ccacttattt    7560
atcatgaatc tcaaatatag tacaatttta tcacctacag tcctcataca ttagatctgt    7620 acacttttttc atcttacaca tctgctactt gcttggatcc tatggcctat atgtccctat    7680
tttctaccta cttttccacc cctattaacc ctgttttttta cgtagtctct gtatatttga    7740
attttgtttc aagcttccac atatatgtga gataatgtaa tatttttctt tctgtgtttg    7800
gcttatttca cttagcataa ttttgtctgg gttcatccat gttgtaaatg gtaggatctt    7860 gttttttttag ggctgactga tattccattg tatctatgta ccacaatctt tttatctacc    7920
tatctatcag tagacacttt agttgtggct attatgtttt tctttttttc tttttttggag    7980 acagggtctt gctgtcaccc aggctgcaat ggagtggtgt tatcatagct cactgtaacc    8040
tcaaacttct gggctcaaga gatcctcctg ccttggcctc ccaagtagct gagactacag    8100
gcatacatta ccatgcctgg ctaatttttta atatttttttg tagatatagc atctcactct    8160
gttgcccaga ctggtctcaa actcctaatt caaatttaga atagagtatg acaattctgt    8220
aaaatataaa aaacatgtcc actccgtata ggaagttata caatgagaag aagacaaaca    8280
```

```
ctatttacat tactcttgat aagttttta caaagaaata aaacacttta atttctaatg    8340
ttttaaattc tggtttgcta aataaataaa tattagtttt agtgttttta aaattcctta    8400
tatagttata agtgatcttc ctgcctcagc ctcccaaagc actgggattc caagcaagag    8460
ccactgtgtt ggggcccttg gaaacagata tgctgaaatc ttttcttgtg gatctacacc    8520
cagaagaggg attgctgggt catatgctac tctatttta attttctttt tattttagt     8580 gaatatgtaa taattgtata taattgtggg atccagaatt atatttccat acatgtatac    8640
aatgtgtgat aatcaaatta gggtaattaa catatccatt acctgaaaca tttatcattc    8700
ctttgtggtg ggaacagtaa aaattaaaaa ttctctcttc tagatttttg aacatatgca    8760
ataaactatt gttaagtata tcaccctaca gtactacaga atgctagaac tcattcctca    8820
tatttggctc caatttcata ttctttaacc aacctctcca tatcctcccc tccctcttac    8880
cgttgtcagc ctctaataat cataattcta ctctctactt ctatctcatt gtctttgatt    8940
tagaatatgt ttcataattt aaccaaaggt caaattctta ggtactgcta aggcaaagaa    9000
caaagatcgc attccagctg ttagacattt cttactacta gtcatttta agacaacatg     9060 gggtgcaggt ggtgaggatg agagatagag attgaaacat attctcttaa atatcagctg    9120
ttctcactct gcatagttcc agcacaaaca aattccaggt actatggtta gttaaataac    9180
accagccact aacaacacaa ttcaaatttc tgttaccaca gtataccgaa agtcattgca    9240
taaagtacaa actttgctgc taactcttca gccttcaaat cattacataa ataacagaaa    9300
cccattataa tcagtgacaa aaccacagca cttctttcaa agcttttttgg agattggttg   9360 cttcacatct gttatgcagt tcatacagac agcaatgccc ggacttgtgt ggccacattg    9420
tctcccagtg gtgagcccat gtgatgtttc acgaaaatgc gcaatcaaaa gaggaaactg    9480
gccagcaaag atgaaagagt agcaaacaaa ggaagtgaaa cattctggaa gtaaaatttg    9540
aatcaaacat aagttgatgt atacaggaag tagctaccct gaggatgttg tcactgctgc    9600
aattcaggag actctaaata tgcagtcaga ggaacgtagt gaggtgaagg tatccgtata    9660
atggggaaag aggttgtgat aaagagtgaa ggtgtcccag aggaagtgtt gctgaaaaat    9720
acaccttatg ttaaatacac tgtcagtata tcatgacatt aaagtgcaaa tgataacatt    9780
ttgtaaactg atccaaactt aaaaaggagt atgataattc tgtaaaacat aaaaatcatg    9840
ccgattccat aaaattataca gtgtgaatta cactgaaaaa tccaacatta gagaggtat    9900 gaatacaatt ttttacaagc ataattttaa taatacacat aataattatt tgtattcaag    9960
tttagtaatg ttcaaggttt ggaagaaatt ctgatcctgt gtagagaccc tagttttgaat  10020 gtgcttatag cctattatta catgtgtaat gttacataaa ttacttaact cggattttta   10080
atttcatcag ctatttaaaa tgggcataat ataactatat taaatggctg ttatgaagat   10140
taaataagat gatatgtaaa atgtgttttt tgtttgtttg tttgtttgtc tgtttgtttt   10200
tttgagacag agtcttgctc tgttacccag gctggagtgc agtggcacaa tcttggctca   10260
ctgcaagttc tgcctcccga gttcatgcca ttctcctgcc tcagcccctc caagtagct    10320 gggactacag gcacccgcca ccacgcctgg ctaatttttt gtattttgg tagagatggg    10380 gtttcaccat attagccagg atggtctcga tctcctgacc tcgtgatctg cccacctcgg   10440
cctcccaaat tgctgggatt acaggcatga gccactgcgc ccagcctaaa atgtttttt    10500 tacataatgg gtgttcagca catgttaaag ccttctctcc atccttcttc ccttttgttt   10560
catgggttga ctgatctgtc tctagtgctg tacttttaaa gcttctacag ttctgaattc   10620
```

```
aaaattatct tctcactggg ccccggtgtt atctcattct tttttctcct ctgtaagttg    10680
acatgtgatg tgggaacaaa ggggataaag tcattatttt gtgctaaaat cgtaattgga    10740
gaggacctcc tgttagctgg gctttcttct atttattgtg gtggttactg gagttccttc    10800
ttctagtttt aggatatata tatatatttt tttctttccc tgaagatata ataatatata    10860
tacttctgaa gattgagatt tttaaattag ttgtattgaa aactagctaa tcagcaattt    10920
aaggctagct tgagacttat gtcttgaatt tgttttttgta ggctccaaaa ccaaggaggg    10980
agtggtgcat ggtgtggcaa caggtaagct ccattgtgct tatatccaaa gatgatattt    11040
aaagtatcta gtgattagtg tggcccagta ttcaagattc ctatgaaatt gtaaaacaat    11100
cactgagcat tctaagaaca tatcagtctt attgaaactg aattctttat aaagtatttt    11160
taaataggta atatttgatt ataaataaaa aatatacttg ccaagaataa tgagggcttt    11220
gaattgataa gctatgttta atttatagta agtgggcatt taaatattct gaccaaaaat    11280
gtattgacaa actgctgaca aaaataaaat gtgaatattg ccataatttt aaaaaaagta    11340
aaatttctgt tgattacagt aaaatatttt gaccttaaat tatgttgatt acaatattcc    11400
tttgataatt cagagtgcat ttcaggaaac acccttggac agtcagtaaa atgtttattg    11460
tatttatctt tgtattgtta tggtatagct atttgtacaa atattattgt gcaattatta    11520
catttctgat tatattattc atttggccta aatttaccga gaatttgaac aagtcaatta    11580
ggtttacaat caagaaatat caaaaatgat gaaaaggatg ataatcatca tcagatgttg    11640
aggaagatga ggatgagagt gccagaaata gagaaatcaa aggagaacca aaatttaaca    11700
aattaaaagc ccacagactt gctgtaatta agttttctgt tgtaagtact ccacgtttcc    11760
tggcagatgt ggtgaagcaa aagatataat cagaaatata atttatataa tcggaaagca    11820
ttaaacacaa tagtgcctat acaaataaaa tgttcctatc actgacttct aaaatggaaa    11880
tgaggacaat gatatgggaa tcttaataca gtgttgtgga tatgactaaa aacacaggag    11940
tcagatcttc ttggttcaac ttcctgctta ctccttacca gctgtgtgtt ttttgcaaga    12000
ttcttcacct ctgtgtgatt tagcttcctc atctataaaa taattcagtg aattaatgta    12060
cacaaaacat ctggaaaaca aaagcaaaca atatgtattt tataagtgtt acttatagtt    12120
ttatagtgaa ctttcttgtg caacattttt acaactagtg gagaaaaata tttctttaaa    12180
tgaatacttt tgatttaaaa atcagagtgt aaaaataaaa cagactcctt tgaaactagt    12240
tctgttagaa gttaattgtg cacctttaat gggctctgtt gcaatccaac agagaagtag    12300
ttaagtaagt ggactatgat gccttctagg gacctcctat aaatatgata ttgtgaagca    12360
tgattataat aagaactaga taacagacag gtggagactc cactatctga agacggtcaa    12420
cctagatgaa tggtgttcca tttagtagtt gaggaagaac ccatgaggtt tagaaagcag    12480
acaagcatgt ggcaagttct ggagtcagtg gtaaaaatta aagaacccaa ctattactgt    12540
cacctgatga tctaatggag actgtgggaga tgggctgcat ttttttagtc ttttccagaa    12600
tgccaaaatg taaacacata tctgtgtgtg tgtgtgtgtg tgtgtgtgtg tgcgtgtgtg    12660
tgagagagag agagagactg aagtttgtac aattagacat tttataaaat gttttctgaa    12720
ggacagtggc tcacaatctt aagtttctaa cattgtacaa tgttgggaga ctttgtatac    12780 tttatttttct ctttagcgta ttaaggaatc tgagatgtcc tacagtaaag aaatttgcat    12840
tacatagtta aaatcagggt tattcaaact ttttgattat tgaaaacttt cttcattagt    12900
tactagggtt gaatgaaact agtgttccac agaaaactat gggaaatgtt gctaggcagt    12960
aaggacatgg tgatttcagc atgtgcaata tttacagcga ttgcacccat ggaccaccct    13020
```

```
ggcagtagtg aaataaccaa aaatgctgtc ataactagta tggctatgag aaacacattg   13080
ggataaatcg gctgctatca taatcattcc tctcccacat cagataaatg aattaacttt   13140
ttgaataggg ttatttaata taaagtgctt aagtctaatt atgagaagaa ataagataat   13200
tacacttcaa tggttaaaga gagggagaat aatttgcata ttatgcctga tgtaaaatgt   13260
ttattatggg tacatattaa gtgctaacta attgttaatt gttcttgcta caagtcttaa   13320
tgcagggaaa caagaaatta ttacatagta cctaatatta tcttctaata ttaaagaaac   13380
aatttcccct aaattcatcc cattagcttt ttttttttcg gtggggcagg ggagaaatac   13440
agacttcagt aaacttgggc tgggaacttt ctacctacaa agttcaaata aaataaatta   13500
tcctagttag ataatatcaa tgaaaaatcc accaacttaa atcctggctg tttgatctca   13560
ggaaattatt tcagttatca acttaatgca tcatattata gaaatatatg aaaatgtgtt   13620
taattaaact tactgaatga tatgttttt caggtacttt aaaaataaac tatgatataa    13680
agttacctat ttttcatgca agtatagtat aaagaaattt ctaacactgg agattttctg   13740
aaggttttga ttcttataaa tttattacat cataatgaac aaaactaatt ttcaacatat   13800
tatgatttaa atttccttag taaattgttt caaatttatt ttctttaaat ccatatttac   13860
atatgtatat ttaaatatac atatttactt gtataacaat tcaaaaccat atattaattt   13920
tataattttg tttaatgtca aaggttagat ttggctatat ctattctaaa agttggtatc   13980
acatttcctt tttggaattt tatttttaaa gtagctaaag tcaaatataa acctattatt   14040
tatattaatg cagacattag aggtagacac taaattcatt ttagtatatt ctaaattatt   14100
tattatctac tatgaaataa tataaagaaa aataaagcag aatccctgat ttcaaagaac   14160
tcaattgccg aaaaacagtt accatttatt agacccaaaa tgtactaata tgagtgtgtc   14220
tcttttcctt ttgttttgtc acccgtcatt tggaatgtca gtgagtagag agatagtgtg   14280
aaaggccctc aaggggaaaa atagaggtta aaggtcagca gagacccctac tagagaaatc   14340 agttctacag aaatgttttt aaatgtgtcg attattgcta catgtacact ctgtcatttt   14400
gtaatgtagc cattttattt atgattataa taataaaaca acaaaattat aataatgtgt   14460
agagtacatt ttactgtgca gtgtattgca ttaaaactag attaaaattt atacatatat   14520
aaaaggctat ctagatatta taaaatttat ggctggatct gtaaaaaatt caaaacctat   14580
ttttaatctc gctttgagat tttataacaa gaaaatgttc gtttcaagca aaattttcaa   14640
ttcacgtcct tgaaaaggaa aaaaatgaca acttgaaaca cataattgac tattttttaaa   14700 ggatcaacat ttcagaaatg ttttaaaaca taagattttc agtacagctt ttcgctggca   14760
tttaaatcga actttgaatt gtaaatagct cttgctctta aggagacatc agccatatcc   14820
ttagaagtgg cacggagttg ttaggtagtt gtacaaaatt ctagcctaaa agacaaatag   14880
ggagcaacac tactgtggac cgtttctggt cttgggctgt gtggctatgt caggcttgcc   14940
cacattgcct gtactaagga gaaagcctct tgtccttaca gaccccctta gcttacatag   15000
tctatttgaa aacaaattgc tttgtccaca ccatttaaat attggcttca ggccaggcgc   15060
ggtggctcac gcctgttatc ccagcacttt gggaggctga gcgggcaga tcacgaggtc    15120 aggagatcga gaccatcctg gctaacacgg tgaaaccctg tctctactaa aaatataaaa   15180
aaattagccg ggtgtggtgg cgcgcacctg tagtcccagc tgctgggag gctgaggcag    15240 gagaatggcc tgaacccggg agtcggagtt tgcagtgagc cgacatcgtg ccactgcact   15300
ccagcctggg tgacagagca agactccgtc tcaaaataaa taaataaata aataaataag   15360
```

```
taaatattgg cttcttcaac tggtgagatg aaacctatac aatagtcatg tgaatagcac    15420
taaacagctg acatggtgta actcctctca gactgaggct tatctgggga gtacaaagca    15480
tgtcaagaaa atgtgccttc atttccttag atgagtgtcc ccatcctcca ctctcctcca    15540
ctgttctcct ctctgcttct atgatatcaa cttttctttt tctttagatt ccacatgagt    15600
gagatcatgt ggttgtttgc ctttctgttt ctggcttatt taactgaaca agaaagtttt    15660
tgacatgaaa ttaaacttct gcttgtaaac tcaattcaaa ctatttacac tgtcttctca    15720
aaaatgttaa cttatttaa taaatctact gaatgaccgt atctcatttt gttttatgaa     15780
aagaaattgt aagggtgctc aatagcctct tcattttcat actgtctagc tcctgtgctc    15840
ctattaaaat tactgcaaat ttagcttttt aagaacccct tgtttcacta cctgaagttc    15900
tataaaaaga tccaagttcc ttcacaaccg tttcttatgc tgttattcgt acatatgtga    15960
taataccacg tctgaacacg tagataataa gtagggctg ggtgcggtgg atcatgccta     16020
taatcctagc actttgggag gctaaggcgg gtggatcacc tgaggttagg agttcgagac    16080
cggcctggcc aacatgatga aaccctgttt ctactaaaaa tacaaataat aataataata    16140
ataattagcc aggtgtggtt gtgggcacct gtaatcccag ctactcggga gactgaggca    16200
ggagaatagc ttgaactcag gaggcggagg ttgctgtgag ctgagattgt gccattgcat    16260
tccagcctga acaacaagaa tgaaactcca tctcaaataa ataaataaat agaagtatgt    16320
attgtgttgc ttagaaggtg tggtggaaat taacttgctg agtgagatca aaggattggc    16380
actgaattga aataaagaaa tattcatgct gagtctggtt caaatataac tgcacctgta    16440
agaattgctt tctgtaaact ttccatagta taaaccaaat ccaatcact catggcttta    16500 cattcctgat cgttaaactt gaagcacttt ttaatactgc atgactttag ccaaaatatc    16560
ttagccaaga ttcaatgttt ggttgaacca cactcacttg gacatcttgg tggcttttgt    16620
ttcttctgac cactcagtta tctatggcat gtgtagatac aggtgtatgg aagccgatgg    16680
ctagtggaag tggaatgatt ttaagtcact gttattctac cacccttaaa tctgttgttg    16740
ctctttattt gtaccagtgg ctgagaagac caaagagcaa gtgacaaatg ttggaggagc    16800
agtggtgacg ggtgtgacag cagtagccca gaagacagtg gagggagcag ggagcattgc    16860
agcagccact ggctttgtca aaaaggacca gttgggcaag gtatggctgt gtacgttttg    16920
tgttacattt ataagctggt gagattacgg ttcattttca tgtgaggcct ggaggcagga    16980
gcaagatact tactgtgggg aacggctacc tgaccctccc cttgtgaaaa agtgctacct    17040
ttatattggt cttgcttgtt tcaggcatta acccagataa atgccatgca aattttataa    17100
ttattatgat tgtttcaatt tctggaagaa agttaatgaa acaaaaatg tagtaaaatg     17160 ccaaaggaac agtgacattt cagaaagaat gagggctttc atgttaattg taagtcttgg    17220
aatttctctt ccttggagta acaaatccct ttgtgcctaa tttcctaatt tccaaaataa    17280
agttctttta cttatttctt tatagtgaca tcatctctta ttaaatggca tatctgcata    17340
ttacataaca gttcattgcc aaatacatat ttgtgggaaa tgagagactt aaaatacata    17400
ccaaccagag atatagtttt gaggtagatt ttaaaattct gagaagaatt ttgactgaat    17460 tttttttgaca aacatgggac acgaataaga ttataccaaa gatattataa ctttcatttt    17520
aaatatggaa ctaatacagt atgaggtgtc aacaacgttg aagtttcaca aacatcacca    17580
ctacaacagc aaaataattt ttgcttttc cctgccacaa tgacctcctt gctatttctt     17640
gaataaatca agcatacct tgccctgaca cgttcttggg gaggcctgcc ctaatctata     17700
taaaattgga gccattcttc tcacctctgg tattcccagt ctccctactt ttttccttc     17760
```

```
tttctttctt tttcttttc tttctttctt tccttcttc tctctttcct ttctttcttt    17820
tccttccctt ccttcctttc tcccttcctt ccttcctccc tctctccctc ccttccttcc   17880
tcccttcctt tctttctctt ttttctttct tgcttccttc cttccttctt tccttttctt   17940
tcttttcct ttctttgcca aagtgttatt caccttaaa tataatacat aatgtgctta     18000
ctttaatgta tgattttat tttatttctc ccttctagaa tgtaggcacc atgagagtga    18060
aatatatta ttttgttcat tgatattca caagtgtctg ggagagttc caacttacag      18120
tagacaatta acaaacattt attaaattaa ggagggaagg aagtgagtaa gcacaacaac   18180
tttcatttct gggtctttta taatcatatg cttagtataa aacagtgct attcagctat    18240
ccaaagtta caatcaaaat gattttggat gaatatcttg aaaattgtga gaagaagtt     18300
ttatttgctg gcaaactatt ctgggttgtt tccacttcat gtaatcctaa gtagcagcct   18360
taccttgata gcccattaaa actctgataa taaaaaggca gaacaaaaat atctgtgata   18420
tatttagatt tactacatgt acttacatgt ctagtgtctg gtgcaatgga tgctaatgat   18480
ggcaaatcct tactgggctt ctagtgaagt tcttcagcta atgtttgaat gcatggttgg   18540
tcatggtggt acccctttgt acaaaatatg cttttcaaat aatcttatta gggataataa   18600
ttatattaat tcctggtttc catctaaat tttaattcta ttatagctt cgtaagattt     18660
cacaagttaa gagggacctc agattaaatt agtacacagg caattaatca gttttgtgtc   18720
tccgacccct ttcacgggct aatagaagct atagaccctc ttagcttcag aaaatgcgc    18780
actcacatac gcacatcaaa gagcttaatg ggaagtccat tgacagaccc tctgttcaga   18840
tcaatcttct gattgtagag atgaggaaac agaaatctac agaggaagtg ggtagtccaa   18900
gattgcacag tcatttggaa tagactggac accagtagta cttttccagc cactatatca   18960
cttccccaag cacttcctca aaacttacct tcctttgggt cttatacat tcagttatgg    19020
acaactagat ttaactagag gatttattg cttcagaata ttaagcaaca gggaaacatg    19080
taccgtctt tattcacctg catttaaggc atacaatata aattgcaaat ggagcatgaa    19140
agtgcttaat cttttacaaa actgggttg cttccaccc atctaaaat acttctattt      19200
attttaatat ttaaagcaga aatctaagtg atgtgacaaa attaatcatt tggagatatt   19260
tcccttatag gtagtatagt ttcttactga tttctaatat gaaaatgaag ccatagaacc   19320
tagaaattgc agcatagttg tggaaataaa cattggactg agagtgaaaa tggctagtct   19380
tcctctctgc tcatacacca cctgactgga taacctttcg cagatctcct aaaagtcttt   19440
ctcataaaat gaggaagctc tactagaaaa ttgttgaagt ctaatttagc aataaagttc   19500
tgagtttcta taataattca aagaatactc taataaatgt ctgcaattgt ggtcacatct   19560
atgggatgct aaaaaatctg gatggtttca atgaaagtat ttaatttgtt cattatgaac   19620
tttgaaataa tttatttcat tttttaaact ttgatcaaaa tgaccctggt aaatagaaat   19680
aagcaaactc ttttgcttg aaatgcttat taatgactgc attgagacac tcattcatca    19740
ttcaagaaag aatgtttgct cacactgtgc cagaaacttg gaggaagagg gatgtgacaa   19800
gtagggtac tggatgtcta gcttgtagaa gtggattaat ggctctgctt ttaagatcag    19860
gaacactgaa agggagtaat ggcaccggtt ttcacctttc atgcccttg agggtatctg    19920
gtccatcacc ctctagttga tgagggaggg aaagttccct ctcccttcac aaataggtgg   19980
aaattaaatg acataattct gaacaaccaa taaatcgaga gtaaatcaaa gcagatacct   20040
gttttgttaa tttgatcata tgaatgtagc tgcccttagt aataatttct aagtataaga   20100
```

```
ctagttaaag gacaaatgag ttatcttgaa ttataagatt ttgttttaca gaacaatatt    20160
aactcttgtg tttagtacat tagaataata gatcttttga tccatatttt tactcatgtg    20220
cacataagaa gttatcagtc atacaattca tttcttgaag ttcataccct tcattggcag    20280
agtagaaaca ggttaaaagt gcacaggcag aaattttaag tgcaaagcaa cagtgatgtt    20340
atatagagaa aatttatatt tcctacttct attgaagaag aaagatctgc ttgttctaag    20400
aatattgtac aaagaaagtg acttgaatca gcgttattct gtaatgctac tatgcgtgca    20460
gtgtggagta gccactagaa cacttggtct atcccagctc ctcaacagtg tcttgcttgt    20520
ggctggtgct caaataaatc cttgctgaac taatgagcat ctctttcatg ccacatggaa    20580
tgctctaaaa gagttggatc ctgaagtttt tatattttg taattttctg gagttttaga     20640
gagcaaaagt cctgaataaa ctgtgaagcc actgcctgac aaataataca gcagtcagct    20700
tcgttatcat atcccattga gacacgactt atctacatga tgattaatag ttttcacgca    20760
agaaataagc ttgaaatgtc tgttgccttg gatacttaaa acatccaggt tcagcgatgt    20820
tatttattgt tgttcaaaat cagaatgaag ttcctaagca atgccatttt ggaaaaatta    20880
catcaatata ttatgaacaa ctttttttaa atcttgattt caaatggatt gacacgtgta    20940
tattctgtaa taatcctgac ttaattcata aaaggatagc tagccagttg tgtgctagat    21000
gaataaaaaa aaagcaggtt ttaaaatgtc aggtttgaca ttgtgaatat aatatctaag    21060
tatcctttta ctcatttcct ttgacttact atggctgtca tgttgggctt catgaaaatt    21120 tattttaaa cacttgagtg ttatggaccc tctgattaaa tgattaatca gatgatgtat     21180
gttgccatca gctgaatcat ttaatgttga tttcacaaac aagcacaggt cacaggcaac    21240
atttcagatt tctttgaaga agcacacaca ggtcacaggc ataatcttaa ataaattta    21300 taacaaggta gtaataagag atgtcaggac tggagaaata ttttaattta tagtaagctt    21360 tcccttaag tgtctaataa ttgttaatat aatacattgc ctcaaataat aaaagtttg     21420 gttcttgtcc ttgtgcttga cttcagaaga taaccagatg actattaggt atatttagac    21480
ctaaattaaa agctttgaga cacaatgaat tgcctgattt gtatttgtgt ttcgagtggc    21540
atatactatt actggcacta taatcttaga ttaaagcata ctgtgattat taagaaaaa     21600 tttaagattg atttgtttct aaaggtatgt aacagtgaca ttttgcaatg tggtatgtaa    21660
aagttggtat ttctcactca tatgagagcc cactaatggt acataaactg tccccactta    21720
gaaacacaat tattatggcc tttctttgta tctgacaaaa tttcactggg ttcaagatgg    21780
atgaatagtg aattctaatg acccttaatc ctgtaaggtt ctaggtggga aagtactctg    21840
taattatgta taaaattata aggaaaatag gcttactgct atgttttcat taaaaatcat    21900
taactgagta cttaatatgt gccagacact cagctgggca ccatgagaaa tacaaaactg    21960
agtaacatat gggtggctcc tgccttcaag aaatgggcag ttcaggccgg gagactgaca    22020 tatttacccct gggaaaaagg gagcagctgt ggtctctgag aacaatatgg tttgttacaa   22080
gtatatatcc atcatggaaa aaaagagatt tatcttagaa atgagagagg ctgatgctct    22140
caataaatat catacattaa attgtgtttt tgtcagtaga ctgaaattac ctcacataca    22200
cgcacagata gtagccatga tattttagct gcttagatat agagacaaat acttccaccc    22260
aaatcttagg atcagtggtt aatagtctgt aagcattaca atcccacaac atatgcatga    22320
ctatacatcc aatttaata ttcaaagaac tgattgcgat gatagttttg tttgtcaaag     22380
aaatgtatta taggatgagt gggatagaac tgcatcacgt tacaccaaca aataggttta    22440
aatcatattt gtgcacttcc cttgttcctt cataaatgtt taacatagct taaaattctg    22500
```

```
tggactgcaa cgtgagagca atgaccacac ttctgtgaac ccattttac tgtgcatgtg   22560 ctaacgtcta ttgttagtat tccttcactt gcaaagatgg catgataatt ttgctggttt   22620
cattaatgag atactgttaa atgtaggatg acttcaaact tagttgtatt gtaaaattat   22680
ttttaattgt atacatttaa gttgtacagc atgatgtttt gagatactta tctttattta   22740
tatatatata taatatacac acgtatataa aagtgattcc tacattgaag caaattaaca   22800
tacccatcat catatggtta tctttgcttt tttactatca gtgcctaaaa tctactttct   22860
tgaaaaatta ccagtatgca ctacaatatt attaacaata atcttcatgt tgtacattag   22920
atctttagac ttactcatct tacatgactt aggtttgttt ttacctctac taccatctga   22980
gccatatttc cactttgtaa tttgataata aacttggaaa aatagcactt atatgtttag   23040
gtgacgggca taaataggat aagatgtgtt tatatattat tccatatatc ttgtctccaa   23100
ctacaatgat aaacaacctg tttgtcccta aaaagtaaga aataacttga cttttctgcc   23160
ccttcaagca taggctgtta gcttttaagt tttagggaga cattgatgat gctatttgct   23220
ttatcaagag gaaattgtca aaagaggtct tttggttctc aaactattca aagtatttaa   23280
aaatcaggac aaaatatgtt tacgtgatat tcaagggtac agaaatgagg taatgagat   23340 gccaattgta tttgtcatgc aaatatataa ttacgtgtat gagagttaga tgatacatct   23400
catcaattta attgttcttc tacaaggaga aaatgaacaa tttgtcaact cgtatatgaa   23460 gtaatttta taagaaattt tattaaaact tttaacaaca tttggatttt taagttgcaa   23520
tttaaatatc cccttctacc aggtgattct ggaatcacta agcagttact tgtgaaaatt   23580
ccaaagtagc atttaattct tattaatgtc atagtgaata ctaatgcaaa gaatactgag   23640
ccagaaatta tgcttgttga ataaatagat tatttattga acaagtaagt gaaaaaatgg   23700
aaataaagaa cggatatata ttttatcttc ctgcttagat gtgggactgt cctacttttc   23760
tctggtgttc acaacaacaa tatgataaat ctaattggaa ttcagttcat aggaatgaat   23820
tcagttacat tatggattgt gatgaataat gtacactttt aatttaatga aatcaaatag   23880 atttaacta tctatgctta caatggggtg acataagtct gacaatcctt aatatcaagt   23940
catctccaat tcacatgtat acacactttt tttctatttg gctattggga atcctcacaa   24000
aaatcgaaaa ttgccctttc agtgtacgtt acggtatttc atgccacaca gattttctga   24060
ggttgtacat acagctttgc cttgaggttc caattttgc tcagtggatt gagtatatat   24120
tatttgctat atatcagaag aggcatgtgc ttcctactta tgtcaggtaa ctttgggatt   24180
aatataattg tcctacaaag catagataga tagaaatact tcatccttaa tttctaatat   24240
tatgacatat ctaaagtagg caccttaaa agttaatctc cactaaatac taatgactgc   24300
ttatagtggc aattcatctt tcatggtagt cctcctacaa aggtatacta acatttatga   24360
gtttgaaaca aaggcaattc acaagtgttc tgctagagat ggtctatatc tgctgtttga   24420
tccagcatga tggccagctg gccctcctgt gcatgacggc tcgtggttta actgcaccat   24480
tttgtttggt catatacagg gaaaacatgg catggtgtgg agggcatggg cttgaattca   24540
gggaacagag agttggtctt ctctctctca ctctactgga tgatgtcatc tcccctctct   24600
aagcatgagt tttcttatct gtgaaataaa aatgttgaat taaatgagtt caaaatgctt   24660
tcagtctgtg tttaatagct tgaatcttaa gacaatgtat tcaattatgc gttgccagat   24720
ccctggcaac tcatgtaacc tttctaaacc atagctactc atctgtaact ggccagccaa   24780
ctgcccaggg ttggagtgtg aatgaaataa gataatgcag acaaaagatt tttaaaaatt   24840
```

```
gtagtgcatt atacagttgt aatattttgc caagaactta cattttctct aagaagtgtg   24900
tcgatacatg atcacagaaa atcttttcca tattcctttg tagtttgatg atattaagta   24960
agtaaattgt ataacacaaa gagggaaaag catcactgaa catgccgttt tatttagcta   25020
aataaaatgt aatcactatt agttttcctc tgatttcccc aaagtcatgt gattccattg   25080
agtattatgc acatggtata attagaatgg attctctgct caaataattt tgggaaacat   25140
ttaaattaac aaagtttaaa agtatctctg ttaagctgaa gcaaatctca aaggccttaa   25200
tattgtatgt aagaggaata gttaccatct ttcctaatgc ctctttgacg ccaaacccat   25260
ggagaatagt tctaggtgtt cagtaaaaca cagatttggg atgccacagg ttaattggaa   25320
ctgtcccctg caatcctttt ctctttttct taataatggc tgattgcagg tcctagatga   25380
aagacattta gagagattat caggactcag catcccatat cagaatccat tcttttatag   25440
tcattttctg ttacatttct tgggacaaca ccaaagaaat gaccatcttc attcacatag   25500
gctttgtacc aaatgctgac aaagatcctt ggtgacctag atgggggcag gtctaagtag   25560
attgcagctg taaaattggc tgatgaatga tctcagcccc ttttactcac actcaaaggc   25620
aggacagtcc attaagggga aggagggcag agttttcct taggccaatt ccctatgcca   25680
gaacttttta aatggaagc atttccagag gagaaacaac cccaagcaca gttcaaagcc   25740
ccctcctccc aagttcattt gaaagtggga tggtttatct gcaaggggg aaaagatgag   25800 ggatagggac gggaatatcc ctaccctca gagagtctgg tttcatcctg cacttttact   25860
gcacagccac aaatgccttg gggtgaatct acaatatgat acatcatatg gtctaaacgt   25920
gcctggctga tcctctctaa tacttcaggg gtctaaaagg gataacatgc tctcctgtta   25980
ctcaccgact ctgtccgcca tatttcaccc agccagccac tgccttcact tccgtccgag   26040
gcctaatctg agcccatggg aaacctaaga accctacca caactgcctc aactcttggg   26100
aatcagggtg tatgggggtg acaggaagtg agcatacatt ctccaacttg atatgtcagc   26160
ccccacgtct gtatgaatgt ttgctcacac tgtgactgcc ggccttgctc ctcaggctgc   26220
atcctaccag ggagtaagac ccaagtcctt cctgctttca gacaacacca agcctcatga   26280
gtccccactc agaggaagga ccagagacaa actctaatgt tccactaata cttccctct   26340 tattactttc cttgaaaatc ccttctccct ctttcttttt atacttcgct aatgaaaggt   26400
aatgaaaggg tctggcactt ggaatttaga attgatacat ggttttaac ccgcggacgt   26460 attccacaat aaccccttgca tcttctacta agatgtgggc taggaaggga ccagccagtt   26520
cccagggtca cagtgcctca gctgatgttt catattttca gcaactttat gttagagatg   26580
tccatcaatc agaacaatat ggttagagaa taaactaata aaagtcattt ttgaggacat   26640
gttggaagtc tatcaaaagc attgaaatta tgcatgctct gaccagtcgc atgtctaaga   26700
atttaaatat gatcataagt ttaaatatga agatgtttat cacagaattg attataaaac   26760
aaaattgaaa aaaatagtgc tagaagtttg atcataggga cctcattaaa tgcattatgg   26820
ttgatccatg cagtggtttg ctgaacagcc attaaaatgt tgtagaataa ttattaatgg   26880
tgtggaagga tgctattgtt gcagtatgtg aaaagaacaa attacaaagc agtttgtgca   26940
gcataatatt tttatttttt aaaaacctgt atgtggctta tgtacatata aagacgtgga   27000
ataaatgcac aaggtactca gttttctca gtgaagccca ttttgcattt tgggctgggt   27060
aattcttcgc tgtgggagaac tctcattcat tgtaggatgt ttacaagccc tgggccttac   27120
ctctttaacg ccagtaggca cccccagcat ggcaacaagc acaaaatggt ctctctcata   27180
ttgcccttga ggaaattttg caactaagta actattactg ggtcctagat tacagtctgg   27240
```

```
attattgcgt tcctttctta tttttatttt ctccaattcc ctttaataag catgtactgg  27300
attcataaaa aaacaacata aatggtaatt acaatattcc gcactggtta aaacttatgt  27360
aaataagcat tctgctgctt tagccacaat tgcaatttat gctccttctc tttcttaagt  27420
tcccagttcc cacgtacatt cattcgactg attcaaagt catttagct tgatagactc  27480 ttaaaagtta gagttatcat ttctgctatt tattctttca attatccatt tgtccaccca  27540
tccatctgat ccatttgtt gatgcatgct gtgtataaaa tactcacca gcctggtgcg  27600 gtggctcacg cctgtaattc caggactttg ggaggccaag gcgggtggat cacctgaagt  27660
caggtgtttg agaccagcct ggccaacgtg aaaaaccct gtctctacta aaaatacaaa  27720
aattagccag gcatggtggc agacgactct aatcccagct acttaggagg ctgaaccagg  27780
agaatcgctc gaacccagga gatggagttt gcagtgagct gagatcatgc caatacactc  27840
cagcctgggt gacagagcaa gactccgtct caaaacaaa caaaaaaaat acaatgccaa  27900
gcatcataaa aaatatagtg atatataaga cctatttgtt gtgctctagg cattgacatc  27960
tagctgtcaa ccattaatat gtgtaggagt ctatctatca atattatgga ctgtgcttga  28020
agacttcttc cccaatcttt ttctcttccc attaagtttg aagtgaggtt ttctgagtga  28080
agtatcatag tacatacagt ctcattattt ttcaaaaatc tctggttata gtacatttct  28140
ttcctttatc ccctttgttc ccaactatca aaccattttg gatatccagt attggtatcc  28200
agtattatta aaaagcaaaa cagagaacta ttaacaaaaa aatttgtagg agtaattggt  28260
tgtatggtat ccagtactat tagatagtaa atcagaaaat tattaacaaa aattttagac  28320
gaataatgga ttgtcttgcc caagtgaatt gagtgattta gttgttcttt cattttagc  28380 aagtacagct gatcatttga ggccttactc attgtttgat tttgcaaatt cttactatta  28440
taaatgtttt gggctctgag aaagctgttg tcttaatctg tttgtgctgt tataacaaaa  28500
tacatgagac tggtaatttt acaaacaaca gaaatttatt tctcatagct ctggaggctg  28560
ggaactccaa gatcaaggca tttgtcttca ggttcagtat ctggcgaggg ccggttctct  28620
actcccaaga tggtgtcttg tcactgtatc ctccagaggg ccaaatgctg tgttctcaca  28680
tggtagagag atagaaaggg ccaactcact ccctcaaggc ctttcataat gttaccaatt  28740
ccacttgtca gggctctgcc cccgtgactt tattacctct gcaaggcccc accacttaat  28800
actatcacgt tggttattac gatttatcac atgaatttcg accatactag ttgccatcct  28860
ttcattttca tatatcctta aaactttgcc tttctcattt taatgtactt tatccacagt  28920
atgccaactt ttcgatactt ttgttaacct gtctgacgat atataggaaa ctgtaaaagt  28980 gcagttttg atacactctt tagctgcccg tttacttcta ctgtcgttag agaaccccat  29040
ccatagtgca tgtgtttatt ttgtgtatga acaaagactt tatatatagt ttgggtcatt  29100
tttattcatt agtgcttccc ttataatctc tgaataccat tttattagta catactgcta  29160
ttcttaatag taactagcat gcctgatcat cccaaatgtc taggttcaca ttttaaaata  29220
agttatatct ttgggcttaa cagtttattg aaaggtaaca aggattgagt catagttgta  29280
tgttttggga agtagaattc aactgtaaat agaaattggt tgtttagatc tcactatata  29340
tgaaaaaatg aaggctttag gagaaaatct ccccaaagta cccatttttc atgtgataaa  29400
tatcatgaaa tgatttgaga aaaaatgta tatttgttac agctaacaaa tatttgtgtt  29460
ttttattctt catggagaga atgaaatttc ttctcttctt tacacatttc ttttctta   29520 tagaaactaa ttggtgcctt tataaaaatt aactgcagag cactaacgtg tatatataag  29580
```

```
tattatgtag ggtgtagggt atgttcaggg tatggtgtgt gtgtgtgtgt gtgtgtgtgt    29640
gtgtgtgtgt agctgtgtgt gtatataatg aaatatatgg tagtgttgtt tcagaaatct    29700
gcttggtctt cccagagttc attcatctta taaattcatc tacattgatc tctatttttg    29760
gaatccatga aatgtttttt ggcagtactt cctttaatat agtgtgctgg aaatctggaa    29820
atttctagcc agattagtta caaaaaatta gccagtggtt ttgcactctc tatagaatca    29880
aggcccaagg cctactcttg ttactcaggg ccttgtttta tctggcctct ttcttttcag    29940
ccatatagct ctcaaatact caacaaaatt cttcattcta ggtagacaag tatcttcaaa    30000
atacttccca attatctaat aactgtctta ccactaagaa ggcttttatg tctcctgtct    30060
gaattttatc catgcaaaaa agtccagccc aagcctccag aactccaaaa agttatccct    30120
aactgctgaa acacagtaat ttcactatgt gaaatttcac tttggtctcc tagcatttgc    30180
agatatacca tacatatcct tgatcctttt cctttcatac cttttatatc taacccttaa    30240
gctaataatt ttacctacac tgtaattcaa aatgtatccc cagtcttacc atgtctccct    30300
tctctactgt taccacccta ggctaggcct tcatcatttc tcacctggac tccttcccta    30360
acctctgaac tgatctgcct gcttccactt agacacccaa cctagtccat tcttgagcag    30420
tcggaataat tcttttaaga aagaaaccag atcacatccc cctctgctcc caaccatcca    30480
gtgacctctt atcatacata gaatgaaatg caaatcttta ctgtgtttta aaggccctac    30540
attatctgga cctcagtaac ttcttacttc ctatcccttt tctccttgta tgccaccctc    30600
caactacact ctaactacac tgtcttttc cctgttcttc agacctgcca accatatttt    30660
cactgctcaa ttaatatgta gaaatgaat tgtttgttaa atgtagactg tttccttct    30720 aaagcaaaga taaatgacat tgtcttcaaa aacaactaac tgcccagaat tcctgatttt    30780 aatttttaaaa agacaaactg caagaatgtg ttaaacagta aggaaacaat tcactacttc    30840
agaattctat atgatttcac tgcacgttag taattttgta tattatagaa tatgagggta    30900
ttctaataaa cttaactcta tgctgtatac ttatcatgat agctcatttt cttatatgtt    30960
tataacagca ctacttattg tacatggata cgtgggaaat aaattaattt tctccttaag    31020
aacaaagcaa ccatttcact catgagataa atcttgaaga tttaaaaact acttataatt    31080
aattatacat tattcatata atgttaagta ttttcttagt aaaccacata atttagaatg    31140
gcaattggac agatgggcag aaccacatgc atccactatt aggcagttgg tgagcataag    31200
atgccagaaa gaagattagg aatatcaagg cagggagctt ccgatcgctc ttgaaaacat    31260
tgacccttca ctcctcactc tccacgatgc atttcctttg aaaagtaatg ccttccaaaa    31320
caaagttctc tgttttatat ctaaacttac tcaatagttt ctcatggtta ttgatatata    31380
aaaaataaag taaatgtttt aggcagacca aagaagaat ttcccctcc ctctgccttt    31440 tatgccaagg tgacagctat gaaatgtaca gtacgtttcc tctgcaagga atgtagcagt    31500
gttccattgc aagaagatga gagggagaga aaggttgcac gctgaggaat atagtgtcat    31560
ttgtcactgc ctagactcat cagctgtgtg gaactctgag aggcaccagg cttctttatt    31620
tatttcttca gaaacttcag caaaaaagat ttcattagga gcagagaaaa atgtgaaaaa    31680
cgaattagct tttgtgatgg ggagtagtca tctctgaata ttgatcaaga ttaagagggt    31740
tgtcttcgta acttctttta tccatagtct atactgattt aactagaaaa ctaatttcag    31800
gtggtatttc gggtgtggca gatctttata gtaaatgaag aatctagtca aatctactga    31860
aaaactctgc ttacttaat gtttgatctg gttgaaacca ttttagctta caatccttc    31920 ctctgaaaca gggaatcaat tgatatccta cagcaaaatt atgtggaagg gccattagct    31980
```

```
tcacatccaa tgcaaatttt gcctgtgttt actcttcccc aatccaaaat atatcagatc   32040
ctagatgcca gtgaaatcgt ttgagctaga tggcttgagg gtcatagctt ttttcatttc   32100
ctgttctcag acctcttata attgatagaa taaaatcaga agagccctag agctgtccca   32160
cctattctgc ctcacaaaag tagaagtaat ggcaaccact atcataggga tcatgctcac   32220 cttttttctta ccagacaaat ttggatatta gcttgaaatt aataccttcc ttaaaatgtt   32280
ggaatttggt tatatgcgaa atttttgctct atttattcat tatattttgt atggaattat   32340
ttttgcccta tatttttcact taagtgttct ctacccaaga ttttaattga acccaaatca   32400
gccagacaca cagacatgga ttttgctgcc accaaggtta attcttcttt taaagttaac   32460
ttttaaaatt tggtaaaata tagctttgaa aatttgcatt cgtctagtgt ttgttatgta   32520
tttccccctt ttgtttgatt atatgtctat attttttcttg tagaaattga tttttaacct   32580 gcttttttatg ttagctttta tgagcttctg tctgaattct gaatatgtct ttcttaatgt   32640
cttctaaatg ttttctttctg gattattaaa agatttatta ggcttttaat aattatattt   32700
gttaccttag ggaatgtgtt tgaaaatatt ttaaatggaa ttgccagtta acacagcatt   32760 gaacttttttc ttgttagaga tacattgttt tctaggcatt ttattgggag agaagttagt   32820
atgatataat gtctttggct gatattaact cttctaagat gcattgtttc tgagaacacc   32880
attgtctgat ttcattcagg gaaatttcac acaagccagt agagtcaata cttttttcaa   32940
gacctgttaa ttgatatata taaaaacttg ccattgttta catgcccatt tcagatcctt   33000
tatgtgacct aagctagaaa tgcattttaa cagcatttgt ttttccaaaa atatttattt   33060
atttatttat tatagagata gcgtctctct atgttgccca ggctggcctc gaactcctgg   33120
gctcaagcaa ttctcctgcc tcggcctccc aacagtgctg ggatacaggt gtgagccatt   33180
gtgccaggcc cttgttttta tttttttttga acattgtatt ttgaaagggg tttgaaggtg   33240
atccctagat agcaaccagt aatgattcga gcagcaaaac aatctaaaaa gtaatttttat   33300 aagaaaatgc agaacataaa tgagcccata aaaaattata ttaggttcta tttacattac   33360
taccttcttt cacatgtaat atttcactaa catttaatga atttctgtgc agtgccatat   33420
accattatga attctaggat agaagaatga gtgagaaatg ttcttaggcc ttaggaagaa   33480
ggaacaagca tctctgtgta ataagttattt caactcttct tttacacctc attcccatat   33540
taaatctcag aaaagctaaa gtaatagcta tcccagatct attttagact ccagacactt   33600
acttcaatgt cttgttctcc ttatcagact ggaatcattc caaacctctt aacttctggg   33660
caaccatgat aatgcgacag aaaggacact aaatctgtcg caaatttatc ttgatattct   33720
atccagtctt acttggtact gaaggtcaca agtaaaataa ggtggttgtt ttttgtttgt   33780
tttttttttt ttgacagaag agaaaagaac actgtgagca cagagtgaat gtctaacatt   33840
gattcttgag tagcaggaat tctctatgcg agaggatctc tatgcaaaaa gatctcatat   33900
tctagcacaa tttaaggatc tctatgcaaa gatatcccat attttagcat tatcaataag   33960
ctatggggta atatattgta tgtggtgtgg cttgaattct agaaatttga tttctagaaa   34020
tggtccctgt agttaaggat atataatgtg gccgtctcca gttttctatg aggaatagga   34080
aaatactatc attattagct gtgtgaccat ggacaacttg cttcgttctt cagttgcatc   34140
atctgtataa aataagaata agaaaattta catctgcaag gtgtgatgga gatcacatgg   34200
gataattgtg gtcccagagc ctggcacaaa agggcttaat atttataatc ctccccattt   34260
ctccgtatac tctaaaggaa gtttattgct tatcaaattg tgccgtggtt agttgtacag   34320
```

```
cttccctgcc aaattgtaaa ctccaacact aatgtgacgt tacattttat atagtgctat   34380
gattttcaaa ttgtttgcat aatttcaaat acacagtaaa ttgctttttta ttagtataat   34440 tattgctatt gtcaatatta ttattacaac agcttcacag taagatgggc agaaaaaaat   34500
ttaatttcca ttttacaaat gcacttttga ggctcacaga agtcaaatag accaaagtca   34560
cagggctagt gagggaccca aagaaacaa attgtaattc actgattcca agttcagtgg   34620
ttgccttact gcatcataaa ggctattaca caatccaggt gtatcatatg attcttgtct   34680
atatattcat acatatcaga aaaagtgttc tactcaaaat tgctagcaat caacagatac   34740
tgatagtcat tagtacttaa atctttatca aatgaaatat taatacccat gaaagagagg   34800
acaatgaaag gtttgtatca tttgtatgtc acaagtcaac ttttttcaat cactcattat   34860
tagtttaact gtaaaaaatt atttacattt agcgtgaaac tttcctgtat tctcaacata   34920
tttccttcgg tagaaaagca aacctccagt tctctgttct ttgcttggat acttgccagt   34980
ttgtaactca gctatcaaac agtaaagctc acaaaacact tattaaaatg actaaaatcc   35040
aaaacaccaa gagcacagca tgctggtgag atgtggagca acaagaactt tcattcattc   35100
actaatgctg gcaatacaaa atggtacagt aactttggaa gataggttga caatttctta   35160
cgaagctaaa ctatacttaa catatatatt tgtccatttt cacagtgcta aaaagaagtt   35220
cccgagactg ggaaatttat aaaggaaaga ggtttattta attgactcac agctcagcat   35280
ggctgaggag gcctcagaaa gcttataatc atggtgaag gagaagggga agcaaggcac   35340
ctacttcaca aggtgacagg aaggagaatg aatgcaggag gaactaccaa acacataaaa   35400
ccattagctc tcgtgagaac tcactcgcta tcatgagaac agcatggggg aaacagctct   35460
catgatctag ttacctccac ctggtctctc ccttgacatg tggggattat ggggattata   35520
attcaagatg agatttgggt ggggacacaa agcctaacca tatcaccata tgatccaaaa   35580
tcatgctaca tgatattcac ccaaaggaaa tgtaaactgt gtccacacca aaacctgcac   35640
atgcacgttt atagcagctt tattcataat tgccaaaact tggaagcaac caagatgttc   35700
ctcaataggt gaatgaacaa aaagactggc acatgtactc aatggaatat tattcagtga   35760
taaaaagaaa tgagctatca agccacaaaa acacatggag aaaacttagg tacgtaagcc   35820
agtttgaaag gttgcattct atatgattcc aatatatgac attctgaaag agacaaaatt   35880
ctggagacag taaaaagatc agtgattgcc tggggctctg agaaagtgca gagggatgaa   35940
tgggtgaagc acatggcatg tttaggacag tgaaactatt ctctatgata ctgtcatggt   36000
ggatacatga cctttatacct ttgttaaaac tcagaatttt acaatacaga gtgaattcta   36060
atataaacta tggactttag ttgtaataag gtatcaatgt tatttcataa gttttaataa   36120
tgtaccacac taatgcaaaa ttataataat aggggaattg ggggaagggt aatggagtat   36180
atgggaatgc actgtaatct cagtacaatt attccacaaa cctaaaactt ctttcaaaaa   36240
tacaagctat tggtcaggtg tgatggctta taccagtaat ctcagcactt tgggaagtca   36300
agaccctcag atcacttgag gccaggagtt cgagaccagc ctggccaaca tggtgaaatc   36360
ctgtctctac taaaaataca aaaaaaaaaa aagaaagaaa gaaaagaaag aaagaacaga   36420
agaaataaaa gaaagaaagg aaagaaagaa agaagaaaag aaagaaagag aaagagagaa   36480
agaaagaagg aaagaaagaa acagaaagag agaaagaaag aaagaaaaag aaagaaagaa   36540
agaaagaaag aaaagaaaga cagatgcggt tgctcatgct tgtaatcaca actactcggg   36600
agactgaggc atgagaatcg cctgaactca gaaggtggag gttgcagtag ggtgagatta   36660
cgccactgca ctccagcctg ggtgacagag caaggctctg tctcaaaaaa aaaaaaaaaa   36720
```

```
agctattaaa aatatgtaaa gctcagtcta gatacagtac cagaatagta ggaactttat    36780
ttcacctgtc ctacaaatta tggttgtgtg ccacttgggt aaaactcaga atccaaatat    36840
gtgaatgtaa gatttatggg gaaattattt gtatttcaaa ataatcctta atgaatgcac    36900
tccttctaaa gtagccatta ataaagcagt taatgtttca tttaattata gattaatgta    36960
cataagatat gccaggaatg caattaggaa ctgggaaggg ggtgttattc taataacttc    37020
cacatagcat tgtgagacat tttctgcttt cttcaaattt catttaatta cattttaaac    37080 aaatatttt gtgagcctat tatatagtcc ttcgctagca ctgaggagac atgctttgtg    37140
accttggtga tttcacattc aaatttccct ttcacctaca ctcttccttg ttttttcatg    37200
cctgtgtaga ttgtaaattc ttcctcagat taagacattt tattcacctt tgtaacatcc    37260
acagtatcta gcacaatcag tgccttcaaa aacaattggc ctcaagaatt gattgactca    37320
atgagtgact gaaagactaa attaataagt acacatctat ttgtacttcc ctgcttactt    37380
ataaggtatg acaatgaaat actgagacag ttatacatta cttacggact caatctcatt    37440
tctttacaat ctctattctt ctttttgag tataatgtta ttttacaatt ccactaactt    37500
gtcactcttt attataaatt catatctcca tttcacctga gaataataaa ggcaaggaag    37560
tattttaaat gatcttgttt tttataacta gcattcattg agcaaatcaa agtatgaaaa    37620
taatataggt gtcagtgatt attataaagt tgtatgcaca aaacattcca atgattgggg    37680
ccaatacaga gaaaacatct caatatttgg aattttgctt ttctgtaaat actttgatat    37740
gtacttacat catatcaatt ataactcctg ctgaaaacaa acagtgcaca caaatttggt    37800
agttggagga gactttataa agggactaat tacgaaggtt tagaccgggt taggaaaaac    37860
acacggaata gtgcaatact ttaggatggc aacagcgagc accgttataa ccactaggcc    37920
aaaatgaact aaatgaacag ggagattacc atttatcaga aaaagaggga gaaaggaagg    37980
agagatgacc aagcaagtcc tatgtgaaga cggctgcctg acttgagctg tgtgatcttt    38040
ggactgatac cacctgcctg cactggccta gcagggcgag aatagtcaat atctggaaaa    38100
tggatcacct gaccttactt tcctccctcc ctgtttcctc tttgtggtgt ttccactggc    38160
caaactcaca gcgtagacaa aaggagtgca ttgatgtagc agtggttcta atccagggcc    38220
aattgtgctc ccagggaaca ttagtggtta tcacagctca ggggaggaag ggagaggagt    38280
ggagtgctac tatgattcac tgagggattt ttttaaacat ctacaatgca caggacatcc    38340
ttccacaaca aagtatccag ttaaaaaatg tcattactgc caaggttgaa aaaccgtggt    38400
gtagtcagta caattcatct tctccaggca cagtgcagga gtggggtgga gtgtctgaag    38460
gggaagaagg aagaaaccag cacaccccac aaaagtaacc aatgcaaata ccaaatagga    38520
aaagacagca cttaaaatac aaaagtctca ggaatatatc tgatagtgtt ttatggaatt    38580
tattaaaatt tagcctggag tgagtaatat ttagcaagcc aggtttgtct ttagagaaat    38640
ccttgtgggg tttatacaag gatttattaa caaagggcac acacaatact catattacag    38700
tcagtctggt tatgtaaaac atgggcaaga atgtaatagg acaatgtgat gtattcacaa    38760 aggatttag gactacacag ataatcctct aatgctttca cttacgtact atgaaaggct    38820
atagtttgca tagtgatata gccacgtaag atagtaaact tgacattcat gcagctatac    38880
atgtttgcac acaccaggat gcatgccctt tctacctggt tgattttta ttcttttatt    38940 aatctctaat ttattcccca gaacactctc cataaaaact ttctcacaac ttaaatcttt    39000
aatctattgt gtggatttct gactcattct ccaagctttt cctcttccct ccgcaatgcc    39060
```

-continued

```
ttatagtctt atgactattt atccctttgc ctacatttct agccagatct cttgcctgat   39120
acacactctc atatttctct ttgcacgcta cacatttta tttagatatc acactactac    39180
tttgatttca acaggtctca gtttaactta atttttcctt caagcaagga gtcccttcat   39240
atcagttatc accattggca ccagaatttt tcttatgact tcccatgacc tacaatataa   39300
accatataaa tcactgatgc ctccatagtt ccctccctct caaatttagc cataagatga   39360
ttttaggatc cttgttttt ccaatctctc tttcattctc tcccccatct cttccattat    39420
gaaggtttgg ataggacaca actcatgcct agattagtgc aatagatgct gagcctgtgc   39480
agcggtagtt tagcttttctc tcctggttaa ctttaactgc cacatatatc acttcacacg  39540
tcattttca ttcaaacgta tttaactggc tcttcattca taagaagctg gaatttgtcg    39600
tttgactgat attttaaaga ttttatattt tttctccatc ctcgttctaa tgttgtatct   39660
tgtgtcattt gttcattcat aaacttaaga cttagctaac cactgagcat ccaggaaatt   39720
cagtatctat catgtgaatt ctctaatact ggttgatcca ttgtcaccag agcatagcag   39780
gcttctcctg cctttatgta tgtttgtcat atagttcatg cctaaaattc tttcttaaat   39840
cttaaattcc taagatacac acttttgccc aagatcacag taatctctgc cataatctct   39900
gctggaatct gttcactgtg ttgctcctgc taaacttctt acagatgact ttttttcttt   39960
ttggtttccc tggtatctag tataatttct tatataggta ctcaataaat gtttcctgtt   40020
gatctctaca cctactctgt acaataccat agtgactaga cacatgttgc tatcaagcat   40080
ttcaaaagta gctagcctga gttgagatat aggggtaaaa tacacaacag atttcaagac   40140
atattatgaa aaaaacccat aaaatttctc agtaattttt ttatagatta catgtagaaa   40200
ctataacatt ttgaataagt tgtatcaaat aaaatataaa attcacccgg ttctttttaa   40260
tttgttaaat gtggtggcta gaaaatttaa aattacataa ttggctcaca gaataattat   40320
aatggatggt attgctttag atcaagtttg tctaacccgt ggcccatggg ccacaagcgg   40380
cccaggatgg ttttgaatga gatccaacac aaatgtgtga acttccttaa aacattatga   40440
attttttgtt tgttttgttt ttgtttttt ctcatcagct atcatgagtg ttagtgtatt    40500
ttatgcatgg ctcaagacaa ttaattcttc ttcaaatatg gcccagggaa gccaaaagac   40560
tggacaaccc tgctttagat agtaaagcat atgagtagtt aatgtgtact ataagcagtg   40620
tgatctgata gactatttaa tgttgtttga tggtacatta ttcaagtcga ttattatgtc   40680
tacctatgca gtttaacgac ggtaatgaga gagggcagct tgattacagg tcttatcttt   40740
tgactaactt gctaggccac ctgagaagga cccaaattat ctgaatgctt aactcaacta   40800
atttgtattc acttgaagaa tttcaaggat gtttatatgc catcaacttg ctttaaattt   40860
tttctctcag tgaaaatttt tcttaaaatg agtatgtggt attcaaattt atccttgttt   40920
tctatgatta tcttttcata gcactgtggt ttccaggaac cttttttttt ttgagatgca   40980
ttctacatgt aactattgca cagtttgcat gtagtaaggt tcattattct tctacttttc   41040
caaacacctg gcatgtttac ttgaggttgg tacaccttgt atcccagatt ttgctgtttt   41100
taacttaaat attgaatatt ttgattaaac attatggaaa gtttaaatgg gtcaagaaaa   41160
atagcttttc ttcccatgaa gaacaatacg gcataggagt taagagcata gatttaaagt   41220
cagaaaacct gtgctgccta cttgtgcaaa gtcacttaca tgctgtactt ctgtttcttc   41280
atctgtaagt tctaccccta ggtatttact taagattaat ggaagcatat gttcatacaa   41340
tgacttgtac agaattattc acgatagcat tactcttaat agctctaact ggtaacaaca   41400
caataatcaa tcaacaattg tgctgtattc atacagcaga atactactta gcaacaaaaa   41460
```

```
tggaatggac tactgataac ctcaacaaca tggatgaatc tcaaaactat catgctgtgt   41520
gatgccaggc acaaatcagt acatactata attccagaaa agacaaatgt catccatggt   41580
aacaacaaga tccatgcttg ctggaggtag aggcatcagt tcagtcattc aggaagctga   41640
ttccaagatg gtgttagaat tacaaccatc cacaagagat ttattgcagg caatagctat   41700
gaaaggtaga aagagaacag gagaaaaacc aggcaaggaa aaaccacaat gtagttgtga   41760
tatcacttca aagggaggca gaaggaagga gaattgggta ggaatagcca cagattacag   41820
tgcagttaca agaaagtctt ggcttccaac aaaggttact tgttgaggag tcatgcatta   41880
ggcagacatg tctgggctgt agtttccttg ctgctcccag tcattggctg gaggccagtc   41940
tgggttcctg tgctgtggtg gatcccattg ctgctgcagc aggaggccaa tagcactcct   42000
ggcagctaat tggagagaaa agatccaaga ggtgtacctt catggctacc cccatggggc   42060
tggggtggag gtggaggaga aggagaagga attaactaga aaaaggcaca aaggaaaatt   42120
ggggaaaata atgaagatat atgatttctc aattgtggtg gtcgttacat gggtttatta   42180
atgcatcaaa actcaagaaa tgtacattta aaatgagtgc atatgattgt aagtgaatta   42240
tacctcaata tagttaattt tttaaaaatc atagatttct ttatatttaa tgcatgaaca   42300
taaacctaag acactcctcc actccaaaac ttaattacct tgtgatcagc agagcagaag   42360
gtactttgtg atatataggt agagaagatg aagtcttgtg acatttaaca agggacagga   42420
aaatggacct tgtcctaagt taccaaactg caaaaatatc acctacaaag gctattcata   42480
acatacattt tcaaggggt tacaatattt gcctactata aaattttgga tctgtaaagg   42540
ggttaaatta tttgtgcagg ggaataaaca tcaaagaaac attaagaggt ccagagaagt   42600
aaaataggaa gggtcttttg gctagaggag atatttaact ttcagaacat gtggaattaa   42660
gttgtattga ttatgatctg atcttcttcc ccctaaattt gatcctcttc ctgtaatcta   42720
ttgtttccat catcttcaac tcttcccttt ccctctccct tgtccctcag ttctagtcaa   42780
tcacaaagtc ctacagtttc actttctgta taccttattt ctggaattca tctctagact   42840
tcaaaatata tatatatata tttttttttt tgagatggag tctcgctctg ttgcccaggc   42900
tggagtgccg tggtgcaatc tcagctcaca gcagcctctg ccacccaggt tcaagcgatt   42960
ctcctagttc agcctcctga gtagctggga ttacaggcat ctgccaccac gcctggttaa   43020
tttttgtatt ttcagtagag atggggtttc gccatgttgg ccaggctgat ctcgaactcc   43080
tgacctcagg tgatccaccc gcgtcagcct cccaaagtgc tggaattaca ggtgtgagcc   43140
actgcttcca gcccaaaata tcttaagtag ataattgcac gactaatctc tgcttttctc   43200
tcccagcagc cttccaaatt catgtctcac agctgacaga gttgttcctg ccttcagatt   43260
catgacctgg ctctgtgttc tagctcaggc tttctctctc atatcacctc ttgcctctct   43320
gttgccccca tattttcccc tctggttggt tggtgctcct ttggaaccct ctgcatatct   43380
tttcaagaat attatgactt attatgccta taaactttgt ttaattattt atttctaaaa   43440
tttgacaggg aacttttcga aggcaggtat tgtgtctttc tcatttaaaa gcaaattctc   43500
gcctggcatg gtggctcatg cctgtaatcc cacactttgg gaggctaagg tggacagatc   43560
acttgagcct aggagttcat gaccagcctg ggcaacacag ttagaccaaa aaaaaaatat   43620
atacgaaaat tagcctggca tggtggcaca cccccgtagt ctcagctagt ctggtagctg   43680
aggtgagagg atcacttgag cctggatggt tgaggttgca gtgagctgtg attgtatcac   43740
tgcactccag cctgggcaaa aaagtaagat cctgtctcaa aaaaaaaaaa aaaaaaaatt   43800
```

```
agtgaatcct cagtgtttaa aaagtccata aacatactaa acatagaaga cctccaaatg    43860
aaattaatca attattattt agtgggttgc ttctcttttg ttttaatata gttttaacaa    43920
agagtaaaag ttatgatctt tttatatgta aaataaataa tgccgggttt gacataaatt    43980
ttaggaaaac tagagacgct acttcctaaa aattttcttt ctataatctt cctaaatatt    44040
tttccataaa gtacaaaata atagaaaaaa attaagagat tgagtatcct ttcaggaagt    44100
gatatgacaa atagggttcg agaactattt gaattctcac cacttttcat aagggcagat    44160
ctcaagttaa atttttctat tcgaatttaa atgactttca ctggaatacc attacagaaa    44220
agcttctgtg tttagatggc aatatggagt ttcttttctt ggaatattaa ttgaaggaga    44280
agtcttaatt ttttaagtct atatctccgt atatatttga acctatttta tatgttagtc    44340
cttctcttta gtaaccttca tccacagtga acaagattta cccttacctt taagcagtag    44400
cggctacttt atgtgaagtg aacagctgct ttttttatct gcatctagac atcaagtagt    44460
ccagagtcct ttctaacacc ctagcaatag aagtaagaat attttgacca ttccatgact    44520
tgatgatact tctagtaata atactgtatt attaaaaaca aacaaacctt tgtgcagtgg    44580
taattgaagc agttccttgg gaacatgtat taagtacttt ttagcagtta agtccactct    44640
ctgtaggtta aggaatattt aaataaaata atgtggcaaa tgagttcaag atgataaatg    44700
cgatgagaac taaaacagct ttaattttat gtgggaaata aatagaggaa aagtacatta    44760
cagggctcct ggacttattt ctttcttcaa agtgtttctc ctagcgaata ttattactat    44820
tttttctctt aagtaaaaaa tacacaaagt atgaatctac acaggataat aatattgaag    44880
ttaaggatga tgtctcctcc ttcactctcc aaaatactat ttacttggct tcatggaaat    44940
ctctctcact ccaattccac cgtgtcaact gaggtcttct gttctttctc tccctatagc    45000
atattcctgt tacataaatc ctaaactgtg tcgtgttagt cacacactgt aacctctaga    45060
taagcgcctg tccagaggtt ctcaatcaga gccttgcaaa tatgtattaa atcaatgggt    45120
catcttcagt gtctcagtgg gccccttggat atgttttgca gactgctgtg agtatgtagg    45180
gatgtccagt atcgagggaa gtgtggatgg cttttcattgg ttcttatagg gctgaagaac    45240
acatagagca gtaagcactt ctactgtagg gagagatcga gcttctccca tccccactgc    45300
tggcaccacc accaccctac accccatttt gagttctgaa agtgaatcct tgagaaagaa    45360
cacacaaaac aaccatcata atagtgggca cagctgtggg tggtagaata acattcccaa    45420
gcttcttttc ctacacatga ttaatattaa ttcagcaaac atttattcag ctcctacttt    45480
taaacaggca ctattctagg tactaaagac atagaggcaa agcatacaag actctgcctt    45540
tgtgaaacaa ttaagaaata agtaaaaaga aagaaacag aaaaggcaat ttggatagtg    45600
tcaggtgcta taaagaaaac aaaatgccat tttaataaat aataataata caatgttttc    45660
atactatgtg ctagacacta tgctagtagg tatttataga cataacctca attaatcctc    45720
aaaatggcat gttgatatca ataccccaag tttacatatg agacttaaga tgtctgagta    45780
tattccccca ggtaacaatt aatatgcaca ataaaacttt ttgctcattc atttattaac    45840
ctatgttgat tgagtaccta ttttgtgtca ggcatcattt taaggcacct ggatatagtt    45900
atgaacaaac aaataaaaat ctctgccctc aaataattaa tatctcacag aggttaggca    45960
aaatataatc agaaaataag tataacgtat aggatgccag atcatgaaag aagctatgaa    46020
tggcatcaag aagctggaaa aggcaaggag acagattttc tcctagagtc tccaaaacag    46080
aacacagtcc tgccgacacc ttaactttag gctagtgaga cccctattgg acttcagact    46140
tacaatccca caatgtaata aatttgtggt aattcagtag gggaacaata gaaaactaat    46200
```

```
acgatatcaa aacaaattat atcatagaac aagaaaatgt aattgtgaca aataatacct    46260
acaaaaatgt tgtaaatgct aggcaaataa tgtgtttaaa gcacttaggc caatgttcaa    46320
cgtaaagtaa ttcatgctat aatatcatca tcatcattac caatatttag gggctctaac    46380
aaatgatgta cgtgtaagca gatgtaagaa aatttccttg ctgaagagga ggtattaata    46440
gagtatataa caatagataa caaattccaa ataaaggcaa actaaatgtt ttattggatt    46500
aaatttaatt ttaaaaacta caagaggccg ggcgcggtgg ctcacgccta taatcccagc    46560
actttggaag ctgaggtgg gtggatcacg aggtcaggag atcgagacca tcctggccaa     46620
catggtgaaa cgctgtctct actaaaaata caaaaattag ctgggcctgg tggcgcgtgc    46680
ctgtaatctc agctatttgg gaggctgagg caagagaatc acttgaacaa ccaaggagtc    46740
ggaggttgca gtgagccaag attgtgccac tgcactccag cctggcaaca gagtgagatc    46800
ccgtctcaac aacaacaaca acaacaacaa caacaacaac aacaacaaca acaaaactgt    46860
gagatccatg gtgggctttt aagaggaaaa tgcaagctaa ggtttgttta gactctgagt    46920
actgcatgtg taaaaataaa ggcatgatga aaagatcaag agattagagt gatactttt     46980 atctactagt gtcagagtca tgaccagggg attggctatg agaatacata agctgtgcca    47040
ggagtaatcc aaggagattg tttcaatttg gaagagtgtc cacagaatga ttctcatact    47100
agacgttggg ctattgtaaa gaaagttggt aggtactcca tcgctaggat catatcaggg    47160
agaaattgaa caggatggcc ctaatgaccc tgttgtaccc ctagcttatg gattaggcaa    47220
gtcacttcta ctcgtatacc ctgtttcccc atttgtaaat aagaggatgt gttactctaa    47280
ggatctctaa gattctttgc agttgttaaa ttgcatagct ctccactgat tccatggtgg    47340
aaatttgcta ttctattaca aatattctaa atgtatgaga tatcagacat actcatttaa    47400 aaacaaaat acaaaaaata agtattctac aaataaacac agataatgtt taaattctat     47460
atgtctttgt ttctcttcag aagcatccaa aatacaaacc atctaagagg caagaaaatg    47520
tcgtgatgtt cctagtgcaa gttaaaaaga tttgctttcc tcaagtcgga aagcccttct    47580 cattttgag gtttttttct tcttttttttt ttcaagtgaa agcatttgg aggagtcaat     47640 atccatcttt aaaggtagcc aggtcacatg tatacatatg taactaacct gcacaatgtg    47700
cacatgtacc ctaaaactta agtataatt taaaaaaaa gaatttaaat aaaaaaagaa     47760
aatcagagag aaaaaaaaaa agatgcatgt gcaccctgat actaccatcc atagtgatac    47820
ggtttggctt tgtgtcccca cccaaatctc atcttgaatt gtaaccccca tgtgttgagg    47880
gagggaccct atgggaggtg attggatcat gggggtagtt tctccatgct gttctcatga    47940
tagtgaatga gttctcataa gatctaatgg tttaaaatca tggcacttcc ttttgctctc    48000
tctttctcct gccatgtgag gtgtgccttg cttcccttc ccttctgct atgattgtaa      48060 gtttcctgag gcctcctcag ctatgcagaa cggtgagtca attaaacttc tttctttata    48120
aaaaaaaaaa aaaaaaaaaa ggtagccagg taaaaattac ttgtttccag gacattttca    48180
cctgaaagaa gcattgtcat ataacataga agcaagaaat ccagtagtgg gggttattta    48240
aaaatagctg gaaatttca atcagcatga gtttgaagca acaatttatc atcaccttt      48300 atggtgggtg gggttaagaa catttcagcg ggcaaagtgg tggtgatggg gaagagacac    48360
caggggaggt gattcccatt gcattgcttt gtaaacagag gcacaggttc ttcattttg     48420 tcacacaaaa tcacagctat gcagaattta ttaatttatt cttctgagac aagaaaaaag    48480
ccaccaaagg aaaccaacag cttgctcctc tcacactggg ggaaccatat gagagactta    48540
```

```
tctatccctg actttaattt tgacctgagg agagctcctc ttaaggaaaa caaattaatt    48600
caatgactat actacttaat cattgacctt tatttaataa gagatttttc cataggatat    48660
gctgagctgt ctcacttaca tcagttgtgt ctcctgaggt gggtgacagg agaccacaaa    48720
tattgcatag cacacaaatc gttaatagca gctgtatacc aaaccattac ctaaatatgt    48780
agagtacaat tcattctcac taatgtcaga gagcatgcta taaaatggtg aatccggaca    48840
gctgaagata ctgaataata acctctattt tgaacaagtt tacagtgttc caatcagtaa    48900
ttaaattgat acctgatgaa tatatgtgtg tgtatgtatt catagcagag atggttttcc    48960
tgagataagg attttgttat tcggataggc tgctgctgga attgtccttc taccettgtt    49020 tctttgtcct tagtcatcac tcatacctct ttccactctt ctgccatcac ttttgtcacc    49080
aaagtcatgg tcctttcccc gccgattgct gctgcaggtc tagggcacca agacttaggc    49140
agcactcacc atgtgccaag aactggacca caggtaccat ccagcattgc tcatggagac    49200
tctgtccctt tctgtaggac accctccttt tagctagcaa cccctccacc acctagagcc    49260
tctggacctc tcattttaat attaagaact aggaaaactt accgctgaga ataactagta    49320
caactagaac tggtagagaa atctgggtct cttgggaatg gattttttagg ctttattgat    49380 tagaggtgta ttaataatgc agtgtttatag tttcatgaca taacgaataa aaaagttcat    49440
tttggacttg cctttcagct ccctaggagc taaaagacgt atttaatgta acttgtgtgg    49500
tggaaataag ttcttttttc aggcaaaaga tgtgcaaacc catctgggga agaacatta    49560 aaaactaagg agacagtgtc ctagataact atgttctttt cctgttttag tctaaaataa    49620
tgattagttt tcttatatat cttcatttgt cttggttcct tttagcccaa tttaataata    49680
ttattgcaga tattgatgaa aacctttacc ttcctcttaa ttcatcaaag tacttgataa    49740
aatttataca tagtacatta attgggaggt ttttatgaga ttaattaata taatgaactg    49800
atgttgaaat tatttaaaac ctgaattatt attgtattaa gtaggacact taatacagtt    49860
aatcagttct gtctttattc atttgtgaga attttttggca agctattgtg aatattcagg    49920
gaagggaatg tattttagc aggaatctta tacctcctac atagaaatga agcatttact    49980
gaaacatcca tgaaacaaaa tgtttctgaa tgtgtactat acacttgtta taagcccctt    50040
ttcttctgta gctatatttt ggagaaaaat ctttgctttg acaaaaaaaa ttatgttgac    50100
ttacacatat attttataac taagcagtgt ttggtttgtg ataaaggata caaaaatata    50160
aaaatgttca gcacacgtaa gtaaggcctt gttgacagtg tgagttatgc tactggatac    50220
tcaaaaggaa cattcagtgt tctcaggtgg tctctagact gtctcaagcc taggaagata    50280
ttttataagc aaaggaataa gagaaggaag attcagattt aatccaagtg aagaattcag    50340
ttttgtgtgc cttatcctgt tattttgaga ggcagccaaa agatgctggt cagcaaggag    50400
aattgtaagt tgggcagcca actctgattt ctcaacctct tagctgtttt cttaaactca    50460 gaattttttaa tgaatttaaa tgtccatatc aggtagactt tggggatgct tttaccagtg    50520
attttcagaa tgttactttc tggcatttct tttcacgtag cattatatta aaaatgaatt    50580
cattcatcca ccttcccttg tccttactaa ttttccctcc tactcccttc ccccttgttc    50640
ttgccatggg gacatgcaaa cactggtggt tgatgtctga gcaaggctgc tgacaggggg    50700
aggaaggaga tgtcaagcag aggtcaatgg cagtgtgccc agcagcctag gaagtaggag    50760
ggaaaagaga gagagacaga gatggtggat gaaagagaaa gccaggatga ttatggtggt    50820
tatgatactt gtcatgctga acacccaatt gagcacccaa taagcacata ataatttaat    50880
catcctctgg cttggatggc agtgttctat cagtgttgac ttcctggttg tgacagtttt    50940
```

```
acagtgttag tgtagaagag aatccttgct ttagagaggt acttactgaa gtacttaggg    51000
ttaatgcacc attgtgctgg aaaaagatac gcacacacac gcacacacac acacacacac    51060
actctcacac acacgcacaa atacatccat gtgttaggca gagggagcaa atgaggtaaa    51120
atgttaacaa ttaggaattc tgggtgaagt ggatagaggg actctttgac tgttcttgaa    51180
acttctctat acatttgatc tgtttcaaat tcttcagaaa atcaaactac aaaaacttaa    51240
ttcatttagt gaacatctac tgaacatctg tatattaaat agtgttaaat gaatgtcaat    51300
taaaatgctc aaacacagta gaggttgatt ctcattcaca taagtccatg gtaggtgttt    51360
ttggcaggtg ggtgagtttc tcccttaggg agattgagga acccagactc ctcccaagtt    51420
gcagccccac cgtcttctga ggggatgcat ccatacccac ttcgaagtag catacattat    51480
ttcctttctc attcctttgg ataccagcca caatttattc aaggtagaca gaaaattgta    51540
gtatatagcc atatgccctg acaaagaagg gagaacagat tttggtggac aactagcaaa    51600
ctctgataca atctgttatt aagcactgtg tgtggataga tgctaactag aaggagatta    51660
tcttcccttc agcaaatata aactgaatgc cgtttatttg gttgaaacta agctagatca    51720
tgggagtata gaaattttat aagaagacat agtcacttct gtcagtgagc tcaagaagaa    51780
ttagtatgcg gaatgtaatc ataccctacag ggggcttgtg ccacttaagt aaaatgaaac    51840
attattttga gtacaattta gcaataaatg tactacgaga tcattaaaaa tcatgtttga    51900
atgttattgt gtcaaggatg ggaaaaagac ttttgggttg tagacttgat aattatagtt    51960
aaaaacagtt tttattcttg tttagtctta tttttttatgt ttaaacatat ttatacttgc    52020
taacatttat acttgctaag taaagactgt ttttacaacc atgacaagaa caaaacatat    52080
tagtaatgca aatgccacat ttcctacaat caactaatca cactaacata tttgcatgga    52140
agaatcactg ggattgatct ggccacgtgt gtagtcatgc ccaaaatgtg aagtccatct    52200
gttttgcaat ttttttttaac cactgttatc caaatgctcc ttggattttt tttattagtg    52260
gatatatttt ggaggtcaga caccctcttg gctagatcat cacctttata acaaatatat    52320
atactattct catggaaata tatttagaca ttgccctact gggaattttt ttcaagtaat    52380
taatgtacag cttgtgcaac agcttgatct tggcttcatg gaataattc actcttagca    52440 gcatctaatg ccacaaagca tttatggatg tcagctcaga acttactttt atttatctct    52500
gagttacttt tttttttttt ttttgagac agagtctcac tctgtctttg gcttgtccct    52560
aacctcttaa cagacttaat attaagctcc atttcactca gtcgttctgt tgtcatataa    52620
atgagacatt ctacaagcat agtttttagt ttctgccaga gcatcataca acattgtgag    52680
ctatgatgaa gataaagacc tagagaagat atttaatatg aagttcatta tctaatattt    52740
ggtatgtgtg gcaaaatagc aatctactgc ttggttctgc tgtaatctat ttacccaccc    52800
atcccatctt tctttcaatt taaaaggata atgatttag tcacgattat acataaaccc    52860
attaccatag gcaataaaca atggggcaaa ccattggtcc catagttgga gtgtggtctg    52920
aagtgtgttt tggtggagag agatctatgt ctggagatag ctaacatgga tttggatccc    52980
agatctgctc ctacctgttg ctgtgcctgt gaccaaatca tgtgatctct ctggtttcag    53040
tttacttgtg aataaagtaa ataccttcat caacacctgt ttttgaatac aatgttttc     53100 tgtaattttt gcttcttata atgttataat gatcatcctt acatctaaat cttggtttac    53160
attttcatca attcttttgg aaagattgga gaagtaaatt ttggagatgt atgtcggcta    53220
ttaaaaatgt ttaattttttt aattaaaaat taaaacgttg aaaaatcctg atgcaaaata    53280
```

```
aatgcattat gcttagtgaa ctcttctcat ttcgaagttt attcaccttc ttgttttttgc    53340 aagtttcctg aaaaatgcat ataaagtcac taagttagca gaactttata aaattatata    53400
actatatata atcttttgat atcagtgaag ccagctgatc ctatagaaat aatgtaggaa    53460
ttataatcac tagcacataa tttaagagtc ctgtggtctt attcatgtta tttaccctct    53520
ctgaatctta catatagtaa gagggttatt atacataata tgtgtacatg tatacaggta    53580
agtaagtata tatgcttatg tgtaaaagca gagttattgt gagagtcaaa tggaaatgtg    53640
aaagtacttt gtagtttttt attactatta ttaattttta ataaaatggt aacattcatt    53700
taataatcat tagttttaac ttcagattgt actggatttc ctctagtatt tcttaagatt    53760
agtgaataaa gtatttctcc taataaatat attgactact gtctttcgat caaacatatt    53820
aggtatattt ttacagtagc atcaggcagt gaaaatttga agctctttat agaggactga    53880
tttatgatga aaaggaataa catgaacaaa tggaattata tgaagcttcc ccagaaatat    53940
ctaagagggg ccaattttaa gaaatatctg acttcttttt catggacatt tcaaaataaa    54000
cctaactcat atggtacagt ttttaagagg gaaaagaaaa aaccatctga gaatctctgg    54060
aattctgccg aaagtatcac ttggcatttt attctacctt ctggatgcag ttgattgaca    54120
gtagtgttat gatgccaggg gtatagtgac tagaaaaaga aaaccaggga attcagtgtt    54180
cttgctcatg aagaacagct tggttctttt aaaacaatga gattttgcca ccccatctca    54240
caaacctatg atttgtgaga acaatccctt ttgtgttgca agacttttac atttctcttc    54300
ccacactata ttagaagaat aaacattgct tcataagtac cgattgatag tctcatttca    54360 tattttttaaa atagagttac tttaaggtta aattttttcat gtagattaaa atgactaagt    54420
aaccattcac atatttcaaa taaaatatat ttttactaca aaaggaaaat aactagattc    54480
ttaagtgtta tagtcaagtg taattgagta atatgaattc taaatgaatt tctaagatct    54540
gctcagcttt cactacttta ggaaggaaca acttaagaaa aattttaata aagatatctc    54600
ttcacacaca tggcagtgtt gtacttagag aacatgaccc aaaatttttt atgactgcat    54660
attgaattcc tgatactctt gggaagctcc aaaagcacca gtggagtttc cagatgtaac    54720
tgtggctgca gacccgccag tcccggtgtt ggaagggatc attataggct cttgtgtgca    54780
gactcatctt cagacccaga ggaattaaat aacttgccca aagtcgcaca actttctcat    54840
ggtaggttgg gcactagaat aaatattgct ttttcttaag agttttagcc tccgtattat    54900
gaaatcttct atgttctgct gatgatatct cctttcttca tctgtttttct attttttaagc    54960 aatgaaata caaacttgca actccccatt tccaacacaa cttagaaaaa acaatattta    55020 aagaaaaat tacaggcatc tcatctcctt tacctgacag atgcttgata gtaatggcct    55080
ctagataggg atgacatcta atataaatgt gtcctttcaa gtcaagcttt ctctgttcat    55140
tagtagaaat attgtatatc aagtgtgcaa aaatttctt caacagggag ctttgtttcc    55200 ctcctttttat tataacaatc tgagcttgt ggtcccaggg tctcctagtg cctgtcttta    55260
ggtctgttta ttcacatgaa gaaagcatgt catatagtat tatctaagac tcaggctgct    55320
tatgcatgat gacagaaggg ttcccaggca caaacattca tccatgcatt catccatcca    55380
cctattcatc cattgatttg gctgataatt ttgactact gttgagttgc cctcagattt    55440
agtttctgtc cttctgccat ggggaaatat ggggttaagc cacaacatac tcttctcttc    55500
tttttctgca ccttcttagt atatttagtt ccatttgtc tagccctgcc tctgacttct    55560
ttgttgtact tcaggttttt tatcattgaa agttatttct ggatcataga tcattctctt    55620
ggtcactttg cttgttcact tataaaatta attcagaaaa aatgacccac agtaattacc    55680
```

```
gtaaatcaca gaccataaac tataatactg tatattgtat tatagtacag aaatatttat    55740
actttaaaat gttttaaata tagatattat aaaaagatat gtctcatata agtaatataa    55800 atacttttt  attacctctt ctctccctat tctccaggcc agtgttttaa aaatccatct    55860
ttatatgtcc atcctggaaa aaactcatga tcataaatga gtttctcaat agagtttata    55920
agcccacagt tgaaacacaa ttgtcttagc atccatttag ttgtcatact tttaagattt    55980
aatggcaaat attatgtttt gtttcttcaa agaaatatt  ttaaaatttt agtaaaggca    56040
gttagagaag gtagagataa tggactgttt aatcctactt ttcatcccac aagtgaacaa    56100
aaaaatgata aaacattttt cccaaaatgt agctttaact atacttaaat ttggactaaa    56160
atgggagata tcttttctac tattgaaaag ccgtgtctgt agattaatgc taaaatcggg    56220
tgtaaaagca aaatttgttt ggcttgattg ccaatggccc attcatttgg ctacagaaac    56280
aatagcacat agcaacagat aatgatgtga gatcacctag ctcaagtaag agtgtctgat    56340
ccgtcaaaaa tatatacatc aagattcaaa agaaatgtgt gttttctcaa gtcatctctg    56400
taaaaataca ttaaatagag gaatagaagt ttgactttga aaatacattg cagacccaat    56460 ccgtcttttcc tattttctgg tgaaaagtat caaatatgtg gaacctggaa ctgctattct    56520
ccttcttaaa aatctttctt aatattctat tgataactgg tgcaagccta acttttgtc     56580 ttacccgatt cttctcacac caaagtgata ggaccttcag gtagcctttg gatagaagat    56640
aaataataat ttaactattg atggaagtta gtattagaat tagacttgga agtctatgga    56700
ataaaatgat tctacaacaa tttgtacttc agacattagt ataacaaaac atgtttgccc    56760
gtgcatgcgg aaacaaccaa tttcatgtgg atgcttatat tcacaaagga gtaaccacct    56820
ggggtttccc actgttgctc cagagaaaac tagcagcagg agaacttctc tgaaggtatc    56880
aagacatctt taaaaacac  ttgttaagtg ttggttcagc taaagcaggg agttttcagt    56940
tagtaatggc ttttaaaaat taaacaagt  ttagcatgta ggtcattaac cttgaatcac    57000
tgtcatgatt attattaacc atctgttctc aaatcgaaag atattttctt tttctagatc    57060
acatttattc tcacattgct caatttcact atatatcaag acatgaaaac tgtaaaaatc    57120
acaccttcta cattattatt tttattgaaa aattcctaat gaaacagtgc gctctgggat    57180
agagaaagga actaactgac attttgcttc ttaacttgtt tttatgcaag ttctaagtgg    57240
tttctggcca tgtacataaa agacaaatat ctggaaaaaa aactagcaga agtcagttat    57300
ttggctctat ctactttgag aattatgtta tataaatgtt aggaaatttt ttgtaatatt    57360
cttatttaga aatgaaatat aaaaagtttt aaaaatatct aaggacagta tacagtccta    57420
aagtaaagct gttaggtaaa tgctacacaa tcctcttatt acagagtcac ttacctgaga    57480
atataagaag agggcctctt gtttaagagt aaatgtgagc tgcaatcagg attctgcact    57540
catttggaca cttagttttg tttttccatg actggtgttg cctgttactg agacacctac    57600
ctgtcatgtg accacagctt atgttacaat gtgtctagtc agacttagag atgtgtgaaa    57660
gagcagtacc tagacgggaa actatgggtc tataaaggtt ttgccttctt gggcggagtt    57720
caaactagga agccacaaaa cttccagttg cattttcaca gattaatgaa atatattta     57780 cactttttcct gaaagatatt ttatttgtgc aaaccttgtt acaaagtaca gccagttgat    57840
taatcgatga agtgatttgt agtggattct tatattttgt gtaagggtat atgtgaggcc    57900
ctatatatga ggctttctat ataatgaagt ataattcagt tcagcatttc aattcagcaa    57960
tcacttattg ggcctctact cagttgcctt cagggcttta taatttaatt gataaaggga    58020
```

```
ggttaattaa ttaattataa caacagatcg cttaatagtg taactactaa tttaattaat    58080
gacaaataac aatacattaa aagaaatgca ttaataaaaa taatatattg gtgttataga    58140
caataatttt ctgattaact ttattattat tatttcaata gcttttgggg agcaggtggt    58200
ttttggttat atggagaagt tgtttaggta tgatttctga gattttggta cactcataac    58260
ctgagcagca tacactgcac ccaatgtgta gtctttcatt cctcaccttc ctcccaccct    58320 tccccctcaag tctccagagt ccattatatc attcttatgc ctttgcatcc tttagtttag    58380
gtggcagtta taaatgagaa catgtaatgt ttggttttcc actcctgagt tacttcactt    58440
agaataatgg tctccaactc tatctacgta gctacaaatg ccattatttt gttccttttt    58500
atggctgagt agtattccat agcatccaca cacaccccCC tatgctttat atatatatgt    58560
aaatatatca cattttctttt atccactcat tggttgatgg gtatttaggc tggttccata    58620 ttttttgcaat tgtgaattgt gcagctataa acatgcatgt gcaagtgtct ttttcatata    58680
atgacttctt ttcctctggg tagataccta ggagtgggat cgctggaaca aatgattgtt    58740 ctactttag ttcttttaagg aatctccata acttttccat ggtggttgta ctagtttaca    58800
ttcctaccag cagtgtaaaa aaatgttccc ttttttaccac ttccatgcca acgtttattt    58860 tttttatttttt taattatggc aattcttgca ggagtaaggt ggtatcacat tgtggttttg    58920
atttgcattt ccctggtcat taaagatgtt gagcattttt tcatatgttt gttggctgtt    58980
tgtctatctt cttttgagaa ttgtctattc atgtccttag cccactttt gataggatta    59040 tttgttttttt cttactgatt tgtttgagtt ccttgtagat tctggatatt agtcctttgt    59100
cagatggata gtttgcagat atttctccca ttctgtgggt tgtctgttta ctctgatgat    59160
tatttctttt gctgtgcaga agctttatag ttttaggtcc catctattta tcttttttgt    59220
tgttgttgca tttgcttttg gtttcttggt catgaactct ttgcttaagc cagtgtctag    59280
aagagtttta ccaatgttat cttctataat ttttaaggtt ttgggtctta gatttaagtc    59340
tttgatccat cttgagtgga ttttttgtata agttgagaga tgaggatcca gcttcattct    59400
tctacatgtg gcttgccaat tatcccaaca ccatttgttg aataggatgt cctttcccca    59460 cccttatgttt tgttttgctt tgttgaagat cagttggctg taagtattta gctttattttс    59520 tggattttct attctgctcc attgatctac atgtctattt ttatagtagt accatgctgt    59580 ttcctaact atagtcttgt agtatagttt gaagttgggt aatctagtgc ctccagattt    59640 gttattttttt gcttagtctt gctttggctg tatgggctgt tgttttgttc catgtgaatt    59700
ttaagatttt ttttcttgtt ctttgaagaa tgatggtggc attttgatgg gagtcgcatt    59760
gaatttatag attgtttttg gcagtgtgct cattttcaca atattgattc tgccaatcca    59820
tgaataaggg atgtgttttc attagtttct gttgtctgtg atttcttca gcaatatttt    59880 gtagttttcc tgtagagatc ttccacctct ttggttaggt atattcctaa gcatttttttt    59940 tttttgcagc tgttgtaaaa aggctcaagt tcttaatttg attctcagtt ttgttgctgt    60000
tggtgtatag cactggtact gatttgtgta cattgatttt gtatctggaa actttactga    60060
attaacttat cagatctagg agctttttgg atgagtcttt aggttttcta ggtatacaaa    60120
catatcatcg gcaaagagca acagtttgac ttcctcttta gcagtttgga tgctcttat    60180 ttcttttctct tgtctgattg ctctggctag gatttccagt actatgttga atagaagtgg    60240
tgaaagcagg cattcttgtc ttattccagt tctcggggga aatgctttca aattttcccc    60300
cgttcaatat aatgttggct gtgggtttgt cataagtggc ttttattacc ttaaggtgtg    60360
tatcttatat gccagttttg ctgagggttt taatcataaa gcaatactga attttgtcaa    60420
```

```
atgcttttc  tgcatctatt  gagtttatca  tatgatttt   gttttactc   ctgcttatat   60480
ggtgtatcac  atttattgac  ttgcatatgt  taaagcaacc  ctgcatcccc  ggtatgaaac   60540
ccacctgatc  atggtggatt  atcttttga   tatgctgctg  gattcattta  gctagtattt   60600
tattgaggat  ttttacatct  ctgttcatca  gggatattgg  tctgtagttt  tctttttg    60660
ttatgtcctt  ttctggtttt  gatattaggg  taatactggc  ttcatagaat  gatttaggga   60720
ggattccctc  tgtctctatc  ttttggaaca  gtttcaatag  aatttgtacc  aatttttctt   60780
tgaatttctg  atagcattca  cctgtgaatc  catctggtcc  tagactttt   ttgtttcctg   60840
acatttttc   tattattgtt  tcactctcac  tatgcattat  tggtctgtta  ataatttcta   60900
tttcttcctg  ttttaatcta  ggaggtttgt  atatatgcag  gaatttgtcc  atctcttctt   60960
ggttttctag  tttgtgtacg  taaatgtgtt  cacagtagtc  ttgaataatc  ttttttattt   61020
ctgtggtatc  agttgtagta  tctcccattt  catttctaat  tgagcttgtt  tagatctttt   61080
ttcttgtttt  cttggttaat  cttgccaatg  gtctattgat  tttgtttatc  ttttcaaaga   61140
agcaggtttt  tgtttcattt  atcttttgta  ttgtattttg  tgtttcaatt  ttatttattt   61200
atttatttat  ttttatttt   atttttgag   atggagtctc  actcttgtta  cccaggctgg   61260
aatgcaacag  tatgatcttg  gctcactgca  acatctgcct  tccaggttca  agtgattctc   61320
ttgcctcagc  tgcccgagta  gctgggacta  caggtgcctg  ccaccacacc  tggctaattt   61380
ttgtatttt   agtagagacg  gggtttcacc  atgttggcca  ggcaggtctc  aaactcctga   61440
cttatggtga  tccgcctgcc  ttggcctccc  aaagtgctgc  gattacaggt  gtgagccacc   61500
acactaagac  tcaattttat  ttatttctat  tctgatcttt  gttatttctt  ttcttctgct   61560
gggtttgggt  ttgcttttgtc ttgtttttcc  agttcctaga  ggtgtaagct  cagattgtct   61620
atttgtgctc  tttcagactt  tttgatgtag  atatttaatg  ctatgaactt  tgctcttaac   61680
atggcttttg  ctgtatccca  gaggttgtga  taggttttgt  cattattatt  gttgaattca   61740
aatatttta   aaattttcat  ctttcttgat  ttcattgttg  acccaaagat  cattcaggag   61800
cagattattc  gatttccatg  tatttgtata  gttttgaggg  tttcttttgg  agttaatttt   61860
taattttatt  ccactgtggt  ctgagagaat  acttgatata  attttgattt  tcttaaattt   61920
attgagactt  gttcatatgg  tctgtcttgg  agaatattcc  atgtgttgat  gaaaaggatg   61980
tagttgttgg  gtaggatttt  ttgtaaatat  ctgttaagtc  catttgttct  agggtatagt   62040
ttaagtccat  gtttctttgt  tgactttctg  tcttgatgac  ctgtctagtg  ctgtcagtgg   62100
agtactgaag  tcccccacta  ttattgtgtt  gctgtctatc  tcatgtctta  ggtctagtag   62160
tgattgcttt  ataaatttgg  gagcccaagt  gttagatgca  tatacactta  agattgtaaa   62220
ttttttcctgt tgaactaatt  atttttatcat tatataatgt  ctctctttgt  ctttttttaat  62280
tgttgttgct  ttaaaatctt  ttttgtctga  tataagaatt  gctattcttt  ctcactttga   62340
gtttccattt  gcatggaata  tctttttcca  ccccttacc   ttaagtttat  gtgagtcctt   62400
acgtgttagg  tgagtctctt  gaagacagca  gatacttggt  tgatggattt  ttatccattc   62460
tgccattctg  tatctttaa   gtggagcatt  taggccattt  acattcaaca  ttagtattga   62520
ggtatgaggt  actgttctat  tcatcatgat  agttgttgcc  tcaatacctt  cttgttgttg   62580
ctgttgttaa  ttgtgttatt  attttatggg  tcctgttaaa  tttatgcttt  aaggaggttc   62640
tattttgatg  tattcaagtt  actgtttcaa  gatttagagc  tccttttagc  atttctcagt   62700
gctggcttgg  tagtggcaaa  ttcagcattt  gtttgtctga  aaaagacttt  atctctcttt   62760
```

```
catttatgaa gcttagtttc actggataca aaattcttgg ctgataatta ttttgtttaa    62820
gaggctaaat atagggccca atctcttctg gctagcaggg tttatgctga gaaatctgct    62880
attaatctgc tatgttttct tttataggat acctgatgct tttgcctcac agctcttaag    62940
attctttcct tcatcttgac tttagacaac ctgatggctg tgtgcccagg tggtaatctt    63000
tttgcattga atttcccagg tgttctttgt gcttcttata tttggatatc tagatctcta    63060
gcaagactag gaagttttc ttgattattc cctcaaataa gtccttaatg accccactat    63120
ataacatgaa atatctgtta ttggtactga ggtgctggcc acaaacaatt ctgtgtgtcc    63180
tgaaaactct tcagaatatt cgtcatcttt agcacttgtt atcttagtgt ttgggcttgg    63240
cttagagtga tacatctcat aacagggcaa cagaaagaac caggaaccaa gatttatata    63300
acataagtca gtaaaactag aggcaccaga ggtttacatt tacattaggt tacattttct    63360
aacaggtagc aaagcacatg aatgaagttc agtggaaggc cttcctcagg aatccagtaa    63420
aaaccaaaca tacacacaca cacacggaca tccgtgaggc aggaagggat gtccactata    63480
gtacagacaa gcatcctgga aggccatcaa ggagtaggtg ggtttcagtt gcctcaggaa    63540
tgtggcatgg acccaaacta agtgagtaca gatacttgtc attgaggaga agattcaaaa    63600
tagcatccta ggtgtaaaaa ctgaggcacc tggggcaggg gaactaggtc tctggaatgt    63660
tggcttaaaa gcacccctct caggaaaggc ctcatatgcc atgcaggggg ttatatatgt    63720
gttgtgggac acagatggca aggagataat tctatgcacc aggctccact actaacaggt    63780
aaacagacca acattaacag agacttaggt aaaaggtag gtgcccagtg gtcagttctc    63840
aggcacttcc aagatgcacc taacagaaat gtaacttggt gtctattgtg tcctaggtct    63900
aacaactgaa gagaagtgaa ttagtacctc ttgtggacag agaaacaggg gcagagaccc    63960
attacaaagc tgtctcagat aggcatttga agctgtttaa gtatgtagag gcttaagtca    64020
ggctggttct gaaatgtgag agagggttaa gcttcatggg aaatcagcag ggtagtttgc    64080
tattttttat tataaccaat ctcacaatag tttgggacat caaatatcaa attgttggga    64140
atatttatcc atattagtct ttttgccact aatatttaaa aatagtttac aatatacaac    64200
aaaaagttgt aaaatttcca tctccactta atcgatctta tgtaacccat acaatacatc    64260
aaatgtcctt tccccacttt atgtttttat ttgctttgtc aaagatcact tggctgttag    64320 catttggggtt tatttctagg ttctctattc tgttttattg gtctgtgtgc ctatttttat    64380
accagtgcca tgctgttttg gtgactatgg ccttatagta tagtttgaaa gcaggtaatg    64440
tgatgcctcc agattttcct ttttgcttaa tcttgctttg gctatgtggg ctctttttg    64500 gttccatatg aattttagga ttgttttttc tagttctgtg aagaatgatg gtggtatttt    64560
gatgggaatt gcatttaatt gtagatttct cttggcagta ttacccaggc ttttcttatt    64620
ttggcaccct gtgctgctgt ctcctttcc ttctttctgc ttctcttaac caactgttac    64680
ctacacttca atactttctg agggcaattc atcctccagt aagtctccct gaatcttctc    64740
ttccttccct ggcttattat atatccttcc tcttggttcc catagcacct atgcacactt    64800
ctgtcattgc acttgccaat ttgtttata atgatctgct catctgtctc ctcacttaga    64860
ctatgagctc actgagagca atggctgttg cattcacctt atatcctcaa caccattctg    64920
aaggcaagag aaagaatacc cagaggtgga gctgggaagc tggttgtcca agtagtgaat    64980
gactctagtt tgaattgaac tctatagcca gtgggcaatg tggatgtgtt gacagttttt    65040
taacagggga ctagtgaaaa cacatttgg gtttagaaaa aattgcaagt ctgatgcat    65100 acataggaga agagattaga gataggaatt tcacttcaga aatttaacca caagagcaag    65160
```

```
tgacagatca cggaagtctg aaccagacta taaatgtgag aatagagaaa aaagttaaca    65220
atttgggtgt gaaagggcga gggagagagg tgtgaagaat gactaagtgt ggatctgttt    65280
ttaaggattg aatggaaatt tgagcatttt agctaatcag gcctaatatt gagcaaagca    65340
aaactcttgc aaattgttat ttcaagtgtg ggctgagaaa atgaaaaaat ataaattctc    65400
acgttataac ctcttccgtg tgtctgattt gatagaatcc agccccattg cctccaaatt    65460
ccattgcatc ttagaccagc aaacacaagt gaattctact taaccccaga attctgtatg    65520
aaaatcttac tgcctttttt tttctaatca tgtgtcaaag tgtgggaaga acttttattt    65580
atgttttaat aaattgtcag tataaccatt tttacttgaa aatattataa tttttcaagt    65640
aaacaaattg tttctctaag ttgaaaattt tatgatggaa taaaagtatt tttcctcaaa    65700
acacatagaa attttacaac aatattttag agttaactaa atgtttcttt agtagtttag    65760
tcacttaaaa agtgatatga ttatgaaaat acttaaactt tgtcttttaa ctatttctaa    65820
taatgctatt ggtataattt catatttta tactgatctt ttctccaaac tttagtaaaa     65880
catacttctg taaacccctg cccacaaaac tgaagtccac atttacttct gaatgactga    65940
taagtttgta aaagtatgca tgaatttcgt tattaaatta agttttat tatattttat      66000 gcacaatggt ataaattatt aaattaattt tcaagcttat agaacattga taaagattgt    66060
cattagaaaa ccctgagttg attgttatac attacataac ctttcattgg tggattagtg    66120
aatatgttat agggtgacca tgaatccaaa gaatcaaagc tggctacagc aaacagaggg    66180
tcaaaaggat atggaactat gcatgatcca gcaaaacact caatatctgt tttcctggaa    66240
tgttaaaaga caaagaagaa aacttgggga acactagatg catatagttc tggttcttta    66300
agaataaaaa tatgggccgg gccggtggc tcatgcctgt aatcccagca ctttgtggga    66360
ggccaaggcg ggtggatcac aaggttagga gttcaagacc agccaggcca acatagtgaa    66420
accctgtctc tactaaaaat acaaaaaaaa attacaaaaa aaatacaaaa aaaaaaatag    66480
ccaggtgtgg tgacaggcac ctgtattccc agctacttgg gaggctgagg caggagaatc    66540
acttgaaccc gggaggcaga ggttgcagtg agccaagata gtgccactgt gctccagcct    66600
gggtgacata gtgagactct gtctcaaaaa aaaaaaaag aataaaaaca agaatggtca     66660
gagtcctagt accttgtcca gtgtagtgct gccttgagat tgcattgcaa tctgtctgag    66720
agatagtaaa agaaagtgat accttcctta gccctgtttc tctttagact atgctttccc    66780
ctctccaagt taatatctct cagtctaaag cctgggaaaa ggtgccaatt ttgttttct     66840 ttcttcctca cacctcctag aagttacact gggacactat tacttttttc caggctttgg    66900
ccatgtgtat tgttttggag agtcaacttc cttttttctt tcattctgca aatagttttg    66960
agctgtcact ctgtactagg tgctataaaa cttacaggtg catttttacat gcctatttcc   67020 tataggccac gatttaacaa aatgttcata aatgagaatt aggagtgcat gtattgaatc    67080
accacacatt aactgaacag ctttcattgg ccagagacta tattgacagt ggagattcaa    67140
agataaacta gagaaatctc atgcttaaat aactttctat aataaattat ataagagaag    67200
taggttcagg gatcttggga gctcagaagc aggatgagtt aaacaaaagt tggattttgc    67260
ctttagcttg gtttcattat cctgaaggaa gagcctgaaa tatagtgtag ggtgcaagta    67320
gtatatgtgg gtggcaatct cgggaaacag gagcatgtga tgaataagga gaaaagcca    67380 atataaaggt actgcattga gggcaatgag ggctctaatt ctctgcacct tctcaagcat    67440
tgtgcagatt ggttttctgg attatcagcc tgaaggacaa aacgaagaaa cagccattag    67500
```

```
ctcctgtctc ccattgtctg agagctgcca ctaggatatt aacttcctga aattctgcag   67560
aaatctcctc ttactttggc actggagatg cccatacgca gaaagcaaaa aggcacagca   67620
tatttaagga agctcataag aaacagtgca tccagaagtg gcgagaattg gaggaatgga   67680
catgagactc taagaaccag cgcctttgat gttccttttg atctgttatg tagctcttct   67740
tgtacacagg tgagcaaagg catgctggac aaatggattc acatgtgcta aagcatgggg   67800
caaaaaccac atattaattc aggaaaagac aagatgcgtg gccctctctg tctctgtcta   67860
agggtgaatt aaagagggga tatatgtaca gagtggcagg gcaggacttg agataagaag   67920
gctaggtggg tgctctcatg ctagtagcat tatagtacag gtgatgagaa gctcctgaag   67980
aatcatctta acatttgtat tttagagcaa cagtattgag ttctgactta gagacagcaa   68040
aactaaagac agaaagacta tttgattat taatgatgta gatataagaa tatcgtcaat   68100
gtgaactaaa gcatgaagct acttatgata tatcattaaa aggatttaac tgattggaga   68160
caaacgagag ggatggggaa aagaattcat ttgtttttag ttgctctttt tttcctactt   68220
attcctttgt tccgagtgtg aataaacttt gtaaactttt atactaaaac attctgctca   68280
ttcatactta tttctttgat gaaacaagga aacccttgta tagttataaa cgtgtgaatc   68340
aatttaaata ttaggaaatt ttttaaata aagctagttt tctgaagggg aaaaacttgg   68400
ttcaattttt tgctggcaat ctgctttgtg attttgaac atgatatcta catctagact   68460
catgttttgc tagctggaat ttttttcaa attaacgcta ccattattat atgctttact   68520
atttagcttt tgcagccttg gaaatctatg attaatacaa ataattctct atggcaattt   68580
taaaaataca tgtaaaagcc ttcaatctac attgctactg tgtcgtagca caaaaaaga   68640 aaatgtgatc aaatttttaat aaaatctaca atttattccc ttctaaatac agtcctagct   68700
caggagaaag gaagctattt gtattttca gaatcaaatt tccctaaatg aatatagaga   68760
aagaattata actgaaatat tgttgaaaca gtggtcatct caaatctgaa ggtcattcca   68820
aaaaagtttc tgagttttca ttgcctcaat ctaaaagttg gcctttttgg taatagatga   68880
aagtaaaata attgaaaggg tctgttgcag ttttggaata tcttgaaaat atagtagagt   68940 gaagcttct tccctaaat aaaagacaag ttgctgattg ttttctttct agccagataa   69000
gaataatgcc ttcttctct tgttagtctt aacacctcac ttgttactat gtgtcagaaa   69060
ggcgagacac cataaatgga gatactactg atggaggtca tctgacatgg ggctggtagg   69120
cagtgggaag actggtatgg acacaggtgg cttagggggtt ggggaatgat atggaactaa   69180
ggaaatgata attagcagaa cccagtgtgc atgtgtgtgc attcgtgtgt ccgtgtatgt   69240
gtgtactgta gcacaatgca agaaagaaaa aacaaggcag acttttcata atttcaggga   69300
taaataaatc ctttatcact tcatgtagaa tattggctac ttggaggtat atctaaacgt   69360
aaatatataa ctatataact acatgctaat taaaaacata caaagaagaa gtgcctaaag   69420
aattacaaca gaaagtggca tagtgattat tagagttaat ataatataaa taaggccagg   69480
catggtggct catgcctata atcccagcac ttttggaggt caagttgcag ggatcacttg   69540
aggacagggg atagagacaa gcctagccaa catggtgaaa cccatctcta ctaaaaatac   69600
agaaattagc tgggtgtggt gatgggcgct ggtaatccca gctactcaag aaactgaagc   69660
aggagaattg cttgaacccg gaagctgggg ctgcagtgag ccaagatcgc gcactgcact   69720
ccagactggg tgacagagaa agacccggtc tcaaaaaatt aaaaaatagt ataaataata   69780
tttcaaaaca caagtctgtt aagataaaag gtacagagga atggtgagat gactttttta   69840
tttgtgtgat aagggactgt tttctgtgat tgtgagaaag accaggagtt aagaaaaagt   69900
```

```
ggccatcaat aaatcagcca cttatgggga agaaccataa accactctca gatgaaatac    69960
aaatgcagtc attatttaat attattggaa tatttgtatt agtttttggt atgtgctgct    70020
agtgctggta cattttagta gtcaattaat attttgttaa tcttaatttc taactaaatt    70080
ccagagtgaa atggaaataa taatgaaaaa attttattta caaaacagat tttgtttttt    70140
tctgttaaga atgatacaca gttgtccttc agtagccata ggggattggt ttcaggacct    70200
cccttgggta ctaaaatctg cagatgccta agccctgtt ataaaatggc ttagtatttg     70260
tatataacct atgcacatcc tctcatatac tttcaatcag gggtccccaa ccccagggcc    70320
atgaccagta ctggtccata gcctgttagg ctgttcgata ccaggctgca cagcaagagc    70380
tgagctcctc ctcctgtcag ctcagtggtg cattagatt gccataggag cacgaaccct     70440
attgtgaact gcacatgtga gggatctagg ttgtgcgctc cttatgagaa tctaatgata    70500
aatgtaatgt gcttgaatca tcccaaaacc attccccttc ccctcaccat ccctgtccgt    70560
ggaaacattt cttccagaaa accagtccct ggtgccagaa aggttgggga ctgctgcttt    70620
aaataatctc tagattactg ataatgccca atacaatgta aattctatgt aaatagtttt    70680
tatactatat tgtttagaga ataatgaaaa gaaaaagtct acatgttcag tttaagtgtt    70740
gataagtgtg tagagaaaag ggaacccttg tacattgttg gtggaaatat agattggtgc    70800
agtcattatg gacaatagta cggaggttcc taaagaaatt aaaattagaa ttacctaaga    70860
cccagcaatc cctcctctgg atgtacccaa aggaaataaa atcatcacct cataaagata    70920
tctgcactgc tatattcatt gcagcattat ttacagtagc caagatatgg aaaccaccta    70980
ggtatgtgtt ggtgcatgaa tggataaaag aaactgtggt atatgtatat acaatggaat    71040
attattcagc cttaaaaaag gagaagaccc tgtcatttgc cacaacatgc atggacctgg    71100
aggatattaa gctgtgggaa ataagtccaa cacacatcca cacacaaaat tgcataatct    71160
cacttatatg tggaatctaa aaagaaaaag ttcaaatata aagttagaat aaaacagtgg    71220
ttaccggccg gatgtggtag ctcacgcctg taatcctagc cctttgggaa gccgaggtgg    71280
gtgaatcacc tgaggtcagg agttcaagac cagcctgacc aacatggtga atcctgttt     71340 ctactaaaag tacaaaaatt agccgggcat agtggcaggt gcctgtaatc ccagctactc    71400
aggcagttga gaaggagaa tcacttgaac tcaggaggca taggttgcag tgagccgaga     71460
tggcgccact tcactccagc ctgggcaaaa gagcaaaact ctgtctcaaa ataaaaaaac    71520
aaaaaacaca gtccacacac tggttaccat gagtgaggtg gcagggagga gattgggaga    71580
tgtagatcta aggatacaaa gtagcagata tgtaggagga actaaaaagc tgacatgcag    71640
gatgacaact atagttagta atagtgtatt gtattcagga ttttgctaa ttgagtagat     71700 tatagctgct cttgccacag gggaaaaagt gggtaactac gtgagataga caatggatgt    71760
gttaattttt gtcactataa taacctttc accatataca ttcatcttat aacagcatgt     71820
tgtttactgt aaatatatac aataaaattt attttttaaat atctgagtat gatttgatga   71880
tttgtgaaaa tagagtgaat tataataatt ttaaatgtaa gttaatgtta ttagaaaaga    71940
aacagaaaga acataccaca cagaaagtct gtctgaagga tctttgtttt ctccaccaat    72000
acaagtgttc attgattcag aggtggatta tgagatatga ccataaaaca aaaatttcaa    72060
gggaaatata ttttattcaa tgaaaaattc tcaacacaac tgttatatgc cagtaaacac    72120
tatatctttt aaataacagg tcatatctat tatatttaaa attcaaggag agactacatt    72180
agagatgcta ttagatcaac ttctaatttc aaagatttct aagatatgga acagttactc    72240
```

```
cttatacaaa ttaaaaaagc aaatgctgaa gaaattcagc tacatggata caccatgagg    72300
tggaaagatg ctccataact cttagttaaa ctgcactaat tacacataaa aggaaaatgt    72360
ttcatttcac tgtaatttgg aaaccaaaga aagaaaagac tgaattttta catactgtta    72420
aagagattgc gtatctgttc taagtttaag acagaggcaa aatgtatttt attcatttgt    72480
cctgcaccgt ttagaaataa aattcaactt ccttttaatt tttttttaaga ataaaaaact   72540 cagtctaagg aaagtcttaa agttttcatt ttaagtgatc cactgttcta gaagtttaat    72600
attttgttta aaatgtttat gttctgtatt ccaccaagtc tagttttaaa acaaaacaaa    72660
caacaacaaa atacttctct aacttggagt ttaaggtgaa agaaaccaat tacgtggttt    72720
ggaaatgtca cacttttcat ctctttttta aaaaaatttt taattcagga cagaaattgt    72780
atggatttag tgtaagtctt gggatctcac aagtgtcagt atttcactct cctccatatc    72840
ttgatagcaa taacttgaaa taggatctca gtagctcaag caatactggg ctctgagagt    72900
tggttaaaaa ttatttggct gagcgcctgt tgctgaggga agaactaatc tcgagcatat    72960
ttttggagcc aaataccaaa ttgttgtgc ttagcaacac agcaccaggc ttgcccttca    73020
gaatgattct agaccaaatg ccagaaatgc tctggttctg actacagagt tctattcaca    73080
aatgacagga ggcaagaggt cctcctcact ttcagaagaa aggtcctttg ctttcttagt    73140
caatggtagg aaaaccattg tggttttcat tgcattacat aattttttaag gtgattactt    73200 caataagaag tgctctgtgt atatgtgtgt ttatagacgc attttttaaa cactggagaa    73260
tttctgaaag tagtacaaac cttgtaatgt caagtagatg tgggaaaaag ggagtttaca    73320
acattctctc ctgacattgc tctcctttgg catctgcatt tttaaaatgt taaaaatgtt    73380
taaaaacgtg tgcttaacac ttaatttggt gatagttgct gttaccaagg caactctgta    73440
actccaccca gataaaaata aatcttgaag atgagtttct gtgtctctga gcaaatattt    73500
ttgtgaatag tagaagcaga gaaagttaaa gatacctgag cttttgatct ttactagttt    73560
tatagatatg tttatagtta tacatttta ttcatacatt ttagataaat aactttgtaa    73620
agcaattgat tcttcttgta aaaatcaagt atattcttaa tagactgata aactttcttt    73680
ttttgagaca gagtcttgct ctattgccca ggctggaata cagtgccatg atcttggctc    73740
actgcaacct acctctgcct cctgggttca agcaattctc ctgcctcagc ctcttgagta    73800
gctgagatta caggtgcatg gtaccacacc ccactaattt ttgtattctt agtagagatg    73860
gggttttgcc attttggcca ggctctgaga aacttttaa ggtctctttt gcagccagct    73920
atttgtctac cttatttcat tcttaatctc actagccaat attttttctg tttaagtgct    73980
ttcagcaaat attaaatgct tgtgccttca gtcttatcct gtggaaacac tggtaatgac    74040
aaaaacacat atttcaacct aatatacaat agaaacagaa tgccagttat tcatggagga    74100
gaagaataga cttctgtatt taaaataaca ttttgctctg tgttttaaaa tcattcttcc    74160
ttcatcaatt gtaagcatct tgactataat ttatacacct aaagataaat aattcagtag    74220
caatgataac tgaaaacagg acacatacaa tgaactagct aaattaccat acattctcat    74280
ccatttcaaa aatagctctg tacttttttc agattttgtt agaagaatat tcaatacaaa    74340
tttttattca atgaacactt cagatgtcaa gattgttacc cacatggaca acagtaacct    74400
aggtaaagat tctgcagcca ggcgtggtgg ctcacacctg taatcccagc actttgggag    74460
gctgaggcgg gcagatcatg aggtcaggag atcgagacta tcctggctaa catggtgaaa    74520
ccccatctct actaaaaata caaaaaatta gccaggtgtg gtgtcatgtg cttgtagtcc    74580
cagctgctcg ggaggctaag gcaggagaat cgcttgaacc cgggaggtgg aggttgcggt    74640
```

```
gagccgagat tgcaccactg cactccagcc tgggtgacag agcgagactc tgtctcaaaa    74700
aaaaaaaaaa aaaattttat acctgggctc tgtgctcacc agcagaaggg gtaacatggc    74760
ttcttaggac aaccttactt gaccatttac ttctttgaca ctaggggtat tcttagatca    74820
gcaggtcctt ccctccactt atgcacatga ggctcacaga gagtctggga ggcagggaat    74880
ttatgattgg aaacagtata cttttatct aagaaattat taatgtcact gcattcaagt    74940
gattaacacc atcaatatct tcaagactaa ggggattaca tgatgtgtaa aattagaaaa    75000
ctgtcatcta ctagtggcta ggcactttaa ttatattaag catgcaacaa gagaactctt    75060
caaatgaatc catctctcct ctgtattatt tccaacccctt ggatccccat ctgtttctgc    75120
agacaacagc tatgctgctg aatgtcttaa tggtttgctg ccccaactag cttcaagata    75180
ctgcaggtca agcatagcat cttactcttc cctgcatctc cagcacctct cagaatgttg    75240
gtcacataga agatgtttgc tgaggagttg aataagaata tgtacaaggg acacaattag    75300
cattgtttaa aaaagatgta acaagatagg gtaaaggaaa gctttggagg ataaatcttt    75360
agaacaatca ataatatctt ctcctctgtt ggttagttgc ccttcaatct cagccactga    75420
atcaaataca acataattac tattctgata tgttcttgaa tcgaatatcc aataataaga    75480
tattcggatg catagccatg tctaatatca aagcccatgc ttttcgctat tattgtactc    75540
catacattag cttccaaatt tatttgcaat ccaaatatta aaagcaagtc ataagcttag    75600
tatcgccaat gtgatactaa gtatccactt actaaacttt attttcaaaa tgtggtttta    75660
tctcagttta atgaacacgg catgttttaa tttacacttt catattatat agtaagggcg    75720
tggttacaga tatgttaatt tcctgtgctg cttcacaatg atggaacata atagcaaatg    75780
aaactgttaa tttgcagata cccataggcc tttggtgtct gaatagaaat aaacacacct    75840
acaactgaga gaggaagcat gtgaagcatt ccagtgaaca gaggccattt attcagtcac    75900
agacacagga gaaaacaac aattaaaaaa aaatctctga tgaaaagttc ataaaaagtt    75960
cactcagttt aagcatatgt cctataacta cttaaaatag agttcttctt aaatatcatt    76020
ctttgctgtt tttagatttc ttctgcctgt atcaaattaa tagaacacag catacttttta    76080 atttgctctg gtttcttagt ggggcattta ttaaacacat taaaacaata gtctcagggt    76140
tttactgctg atgttaaagt tctgcttttcc tacttaccaa ctgtgtcatc ttaaggcaca    76200
tactttgcct ctctctcaaa tctcccaaat ggagaatgat aagaatacgt acctcaatta    76260
aagaagctat aacaagtaga atgtttggaa aagtgccggg tacaccataa gcccactatg    76320
agtattggat tgtattaccct ctgaaagctg cagaatggaa ttctcaaagt tatatgtccc    76380
taaaatcctc ttaagtgaca gaaatggaga aattagcagt ctgtctaaga gagcttttct    76440
agagtctggg catatgtttt taggacaaga cagttcagct tcagcttaaa atgagagagc    76500
acgtctgtgt ccttactcct gggtgccagg tttcttgtcc ccatcttaag acaaataatt    76560
ttggtggaga agaggcagtc tctttgattt cgctctaaaa acctttttctg gaggaggtag    76620 acactctcca ccccccgtttt gagactcatg cagctgagga tgactggctg agtacaagca    76680
attgttcctt ctaagcagtt tcaattctta taacttgtgg agatattctt aagtccaggg    76740
gattttgtgt atggtggatt tttattacaa agtcctgtac ttcataggaa caaataatt    76800 caaagtcagg aaccagatca aagccacaac tcagatatgg caccttgaga agttcatttg    76860
tatttcactt gcataaaaac cctcaccact gctatctgat tttcacaaat cattcaacag    76920
ctatccatga agcaccccact gtgtgtctgg tctctgtgtc agtccctggc ttcatgtgtc    76980
```

```
tttccttctg taccctgact ccccaactca tgaacacatg aagtaaaaaa atgaaaatct    77040
ttttctgacc tctcttcaaa atcacttttt tcaaaacaaa cacctctcac ctgctcatcc    77100
tccagccagt aaatcacagg ggcctagaaa tgtcacttac aaatattttc tgattctgtc    77160
cctcccttca agcttgccaa cattatcaca gtttagggcc tgctcatctt tcccccaatc    77220
tccaattaga tctctccaca atgcaattct gcacattccc tgttacaacc cttcaattat    77280
ttcccagccc atccaaaata aaatctaagc ctcttactaa cacattcagg aactctgtgg    77340
cctacggttt tctacagact aattttccag cagttgactt ccagtgcaag tgaaaaccta    77400
gtgtcatgcc tgcatgatag ataaatttga agctgaagag cccaaatgta tagaccatgc    77460
catgaaaggt ttatagtcat gacacagtgg ccctatagta cagtgcttga agctggctct    77520
ctactgtcag acagaccact tgccagccat gagacctggg gcaaaatgcc ttaattttta    77580
tgtgcctcaa gttctcatgt gagatgagaa taaaaattac ccctatttca taagatttga    77640
taaagtgttt agcataatac ctcataacaa ttgcaattca gtggtggtta ttattataaa    77700
gaaaagatga ttaactttat cttaatgttt aacttgttct gatagttatt gatctatagc    77760
tttgatatgg aggtttgaga atgacctgga agaattggc cacaatgatt gaagatagtg    77820
atacaagaat aaaagatgac tgcaaaatgt aaacctgcaa taacagaaag aatgaagtca    77880
ctggtctcat gggaactgat atgggagaaa aaaacagatc aaaaggctat tcatgttttg    77940
ggcctctttg tcaaaatgga aatgagaaac tggggaataa aaattaaagc aattctagca    78000
tctggtttta acataattct tatccctaaa aagaatctat aagaaactcc caaaatgaca    78060
ggcagccgtg ggtagcattg catttcaagt aatcttttaa ttgttaaaat ttaagtttcc    78120
aacatgaaca taaaattttc aacctaaaag aaatgagttc caaatctgag acaagtgaaa    78180
aaggataaag cctactaggg ggtaaattcc atctctttag agatctagta cccaatttag    78240
caatgtccaa tcaagccttt aactactaca tttgaacacc tcatcatttc aaaatgttac    78300
ttaatgatgc caattaactg tacaatgtct ctgcatagca catagcccta aaatgatttg    78360
tgcaatgtta ctgtcagtaa aactgaacta cagggaatgc tcatattcta tgtcattata    78420
tacagaaatg caatatcaat aaagtgtatat ctgttggtat tagaaaaaag tgaaaatttt    78480
catatctttc tattttcttt tttcctcaat gggatgctct tgttaaagat agctctgcat    78540
agtaaggttt gtataaacat tatttagcta aagttaaaag gggtaacata ctggttctag    78600
cacagatatt aaaacaaatt agtttgtagg tagggcagca atcaattata ttactaacca    78660
tagctttggt cctttttatcc tttcccatt gattttacac agtgggatgt taaaggttga    78720
atgtctttgg tatctataaa cttaattgaa agctgttatt tgtttgttta agtctgttga    78780
tttttataat cataatttta ctcctataga tttcttgtag gagtactata tgaatttatg    78840
ttgcactgaa ttttgttatg ttatacaaat taataggctt ttatttatgg aaagctacta    78900
ttgatctgtc atttcttaaa aaattactaa aaagtgttaa aactttaaat gttggagagt    78960
ttatatttta aaagttacat gctagaaaaa catgatgtct gagtatatta gaagttatag    79020
ataattcatc tgtcaactat aaaactctcc aacactgcct ttctttaatg aataatatga    79080
aatttagcag tgaaaatgtg acaatgtaca atcctaaata aatcaacaaa tttagagatg    79140
tacctctaaa accattgtaa attcaacagt gtaattttcc attggacttt cacttattca    79200
ttcattaaac aaatgtttgt gagtgcctgc aatgtatgag acattgtact gaagctaggc    79260
agtgtgagtt atcatatggg attatccttt aaatacttct gagggcaaaa aaaaaaaaa    79320 aaagaagaga aaaggtgtga ggaaagataa agggttaatt cattaaaaaa taacacttga    79380
```

```
ggactgtttt ctttgcaagg cataaagtta tcacccttc aaacagtaga tatttcacat    79440
ttaggatgcg agactccagt tccaacaaag ctcattgcac agctgctacc ctgattaaac    79500
tgctacatga actctgagca atgtagcatg gtagccgcat gcttctgctt gcatgatggt    79560
taattccttc cattctcatt agtgatttt tgagctttga aattctgatg gtacctagga    79620
tataaagcat atttatctaa ctgaaaaaca gataattaga tgtaacataa aatatgaatg    79680
gctttgtcac tttattgtag cagagaatga atgtgggata aattaaagct gatgctagaa    79740
catatgccta ttttttagct ggaaaatttc aagatttatg tactttgggc ttgagaaaga    79800
aatggagttt attttttatg cactgacatc tctttttttt ttttttggga agagctctct    79860
taggaatgaa tggtatgtaa atacagtagg aatgtaatta tagattttcc tgacccagtt    79920
cctaaataat agatatcatt tcagaagtgc cccaatacct gaccttttgc tccaagccat    79980
atcaaagcac acatctagtc tacttttcac tctcattcct agccactatg acaatactat    80040
tcagataaaa cttctagtcc tctacttatg tgactcatac caacttgacc ttacgatagt    80100
gactgggggt gcatatctag gttcatgctg tttgtccatt attatggttt tgtgagaaaa    80160
ggcaaaattt ctaggtaaag tgttatgagg acgaataatc caccaggcaa ccaactgacc    80220
ctttcatttg ccatcttgtc acttcaaaca gctctccaga acctgcagcc agcacagacc    80280
aaagtcaggt ttgtctcctc ttctgttgat gaacaaggt tgattccata tcgtggctat     80340
tgtgaatagt ggcagtaaac atggcagtat tgtatgaaaa tatcacagat agcccttaaa    80400
tatgtgcaac tatgatgatc tatcaaaatt aaaaattaaa attattttt aaaagttcag     80460 ttagaaagct tgtagttcct ggcaaactac tacctttctc ggcaaaagaa tttgatatct    80520
cttaaatatt ttctgcctaa tgctgataga ttgtatttac atattccatt aatgcaataa    80580
ataaaattac accaaaacat cagcattatt tatttccagg ggcatctctc aaaataaatt    80640
cctccaaaat tcacaaaacc aaaccaatg tgaaattgta ctcagggatg caaatgtagc     80700
ccagtgaagc atttgcccac ttgtttggta ttattgaagc acaattagaa aaatgtgcaa    80760
tgtatgccca aaaattctat aataagggcc aggcgcggtg gctcacacct gtaatctcag    80820
cattttggga ggccaaggtg ggcaaatcat gaggtcagga gatcgagacc atcctagcta    80880
acaccatgaa acccagtctt tactaaaaat acaaaaaatt ggcccagacg tggtggcggg    80940
atcctgtagt cccagctact cgggaggctg aggcaggaga atggcatgaa cccaggaggc    81000
agagtttgca ctgagcctac tctccagcct gaacgacaga gcgagacccc atctcaaaaa    81060
aaaaaaccat aataagaact ttttaatata ctatattata atgtaaaaag actagatgtc    81120
aaacaaatta ggtgatggga aggaattgag ggagaatttt agactaagca attgagcagc    81180
acctgttttt caccacaaat ctgttacatg tattgctcaa ttgtgctgaa tccatattgg    81240
gtcctggtgg ctatgtaata gtctctttct tggataaatg tttgtcctct cttatggttt    81300
actaatggtg tacagaacag cattgaatag tggttatttc ctatgacttc ctagatatct    81360
ctctcataat cctgaatgtt ttaaagatca ttcttagata gagtacagct agacacgaac    81420
catagtggaa atcaggtaga caaaatttaa aaggagtctt aattgaaggt catttttattg   81480 tcctcagtat taatcttact taaaacaaac ctgtcactga gcagaactca aaacaccaga    81540
gccctttgcc aaatgtgatt ttttacaaca ggagcgctgg cagttgagag gagtattctg    81600
tcacacttga gagaattcga gtccctgaag atttatatga atgcttagct attatcgaac    81660
catctcttca cagatgactt agtaaatgtc tgcctttgca tcagataatg gcttacagt     81720
```

```
taatctcctc ttgctccctg ttacacacat atacaccttc ttcctaaaca gctcataagg    81780
tgaaagaaag actcagattt ctgactatgt aattgataat atcacacgga ctgcctgctc    81840
atcatctgct agtcacattg gcagagttga cagttttgga gacactgaag acagtgcata    81900
tattaggaaa taagcagttt cctgatataa attttcttgt agtttataaa ttacatagca    81960
tttattattc cctcatattt tataacattt aataatagaa ctgacacata tattcatttt    82020
aaactcaatt gtgtataata actatcatag caacccttca gtgcctaaat atcaaatctt    82080
ccattcctcc catgaacatc ttgaatatat aggtactgtg gttagctcca acaagctttt    82140
ggttagaatt cattgcactg atacatagac attgttttaa aggcaatttc aaatcaaagc    82200
tgtcagctgt gaatcaagca caccttaaaa agtgacacat ttgtcactag attccagcct    82260
ctcaaattac tgacacgcat cctttttatg taaagatgac attgttcttt cctgatatat    82320
tgcattcctc atgaatttct tatagtcata gaatttttat aaaccatttc agaatcgctg    82380
aaataaacat caatatttt aacttttca ttctgtcaaa atattgtat gcagagatat    82440 tgctgtaagt gtgtatacct gtgcttaaga gactagggct gaagagaagt aatcaaccga    82500
accactggtg taaatgtgcg tcacattttt agtgactaga aattgaaata attccaacaa    82560
atttatgtgc tttgggcttg agaattcaga ctgcctaggg ctaagataaa aatcttttcc    82620
tggtactata taccttcttt tattgaatga ctacctggct cttttctatta tatatgcaga    82680 ttttgtacct ctggtcatct ttgtaaatgg tgcctaaaag atatttgaag ataagtgac    82740 cagcaataag aacaaatgtc tatacaaaag cacccttag ttggatgtaa ttcactactt    82800
tgagttgtta ataacctcta aggatgacag tagctattag ttgaataaac cattatgtct    82860
attattagaa cactagatag tttataagtc caaacaatgc ataaaatacc tatctcatgt    82920
taccattgtt taggttacca gataattgtt ctgtccaatt attccactta attttttgct    82980
tgcccattag ctaaatggca agataaaatt tgtcaaacgg ggggaatgt attgaaaatg    83040 ctagacaact acacttaaaa tgaaaacagg ccaggcgcgg tggctcaggc ctgtaatccc    83100
agcactttgg gaggccaagg cgggtggatc acctgaggtc gggagttcaa gaccagcttg    83160
accaacatgg agaaactcca tctctactaa aaatacaaaa ttagccgggc atggtggcac    83220
atacctgtaa tcccaactac tggggaggct gaggcagaag aatcgtttga acccaggagg    83280
cggtggttgc agtgagccga gattgtgcca ctgtattcta gcctaggcaa catgagcgaa    83340
actccatctc aaaaaaaaa aaaaaagaa agaaaagaaa acaaatgcat aatttgcaaa    83400 tattatttt atattgtatg ttatctaggg cttctaaatg cattcttctt ataagcctag    83460
gtttgcaata acattcattt agaattgagt aattttaaat ataatatttt ataaaataaa    83520
atataataat ttctcttaat tctttgaaaa tattaaatta aaaggggtt gcaaactctg    83580 cattccacat ttccatccca acatttaatt ttagcaattt tgtagtctgc ctaaaatgca    83640
atccatcatt tactgtttag aaaataggga atgtacacaa aggcctttca gctttccctg    83700
aactccataa aaatctttt gcttctttac tgccccctt tgtcaggagt tctgaggaac    83760 tgtttttat cttaagtctc acaaagcatt taggagaata tttaaactta aattcttta    83820 aaacttatgt tcaggacaaa gtaacattgt atgcattggt gtcatatgta tttaaattt    83880 gaaatttta atactggcaa aatgaggttt caatttaat ataattatt taacaatctt    83940 aaatcattaa atatattact taatatattt aatatatcta aacagtcaca attttcccat    84000
actaataatc ataaaaaatc ttacccaatg gtcatataga tatacttaat ggagttttgg    84060
gggggtattt ttgtatatta aaaaattcat atatttgcct tacttagaag aactgattaa    84120
```

```
atgaaagtat aatattaaca aacatattgt tattttatat ttgcatttgt gataattata   84180
tttgaaacgt tcaagatttt ccaatgaatt tcttttgcat ttgcgtattt gtgccttttt   84240
attataaaaa taggtggctt tttagttcca ctgcataagt ttcaacatag gtctacaaat   84300
agtgcatctt tttgaagtta atcattataa tcacaaattg aagttgcctg agctccaatt   84360
ggagtctaaa tggatgactg aatcttatta ttcgaaaccc actgttgcta cacaatatgg   84420
ccacacaaga gagtacacaa gacccgtctg attcagcctc agtgccataa atattttaat   84480
ggtttcgttg aatctggaa atggagctca ccacaggaga tgcttcttcc tttgactctc    84540
attattattt cctttacaaa ttaattaata aaaacttaga tgctaaatta gcacttgatg   84600
aaaacttata tagccttgac attttgattc tgtgagtgaa taaaaatact tggagaaata   84660
aaaatcctaa tcatgttcag gaatacccac aaggtaacaa gtacatttt aaactttaaa    84720
aacatttatt attcatgata aaacatgttg tgtgatttaa atataaattt ttattatttg   84780
ctttaactta tttccggatt aaaaagtaaa tgtttaccta gctgttctaa atggtaatcc   84840
tcatgattaa aacagcaatt tgtcatattt cagttacaaa tgatctttta ttattagtta   84900
tagaacataa gttctttcat tgactgaggc gatgtttcaa gtagataaat ctgttaaaaa   84960
aattgtggtc atattctgtt aaattctcat accaggcaat ttgtttgata ttcaggaaaa   85020
acctagccac tgaccaaaaa ctctacctgc cttctcagtt gtatcctctt ggacttaaag   85080
gggactggga agttataag atggttcatg atagtccatc aacatcccaa gaacaaaaac    85140
agatgttgta ctgacagcat catatgatca tatgcatgta agagcacatt catattgcca   85200
aatcagttgg aattttcac ggttgaaagt taaatgaaat gcttagatgt atgagtcatc    85260
ggagttaaag acaattacag ccagatttat ggctgtgcta aaataaagct agttagaaaa   85320
cagaccaaat tccatgacga taccaagtct gactaatgat tcaccttaaa tttcggagca   85380
acatttatcc tcacttgttt gtttatttga caatgtgccc ttatccatta agtaactagg   85440
aggaagggaa aagcactacg tgggtgagtg acaagacact gacactgatt tgtgactttg   85500
gataattcct ggatgctgtt atctgttttg gcatagagat ggatctgtaa ctgctaataa   85560
ttgccgactg tgaccatccc agaggccatt tacttaaccc aggtatttca gacctgacag   85620
cccgaggata aacacgattt ccctccatca ctaacttcat ctgcagggcc taagcctcct   85680
tcacagtctc tccagtgatt tattggcatc tccaagggta tctcacatgt gctgaagaac   85740
aaatctgctc actttcatct gcttggtttt cccttttgaa atctgctgct ttaaaattac   85800
taagggagga atcatgcctg ctgctaccct tgccagtgac cttgcagttt gtgccctgat   85860
tgttccaatt accacaatca aaacagaagc gtttgcagtt actgcagtgc tctctctgtg   85920
gatgtcaggt ctgactcaga gagccaggct ggggaacagc catttccact cttgtacctc   85980
tgcaaaagga cttccatgtt ccgtaaacag actcccacct ctcatttttcc ccccaagcaa   86040
agcatcataa attagagagc atgtaacggg aagaaaatc cattagccat ttgggttcag    86100
tcagacaagc cagctcatgg aaagtttata caggaaggtc acatttcaat tgagatcagg   86160
agggtgaaag ggtccagctg tgtgatgaga gagagaatgt tcgggaatgt ggaacagagg   86220
tatccaaggc agaacaaact cgtatatgaa ggctttaagg gtgtgcaaat ctagcatatt   86280
ttatgacata aaagagtcct gattagctag aatatgatga atgtgagaag aggtgaaggc   86340
tggagatagg aaaaattatt ccagatctta taagctatag taagaaattt gcatattata   86400
tatagacttg tgggaagcca ttggattttg taagaaggag attaacatta tcttatttat   86460
```

```
gttatttgtg atttataacc ccaaatgtgc cagatacaaa caaaccaaaa ataataataa    86520
taataataag aagaagaaca acaacagcaa tggaactgtg gtgatggttt tggtcacaaa    86580
atgcatatat atctattttt cacaatgcaa aaatatttca ttatttcaaa ttttaacata    86640
aatgtgggta tgcatgagct tacaaatctt gaagtttatt ggggaatatt ggtgagcatg    86700
gtttttattg catggtcaca acttactaat gggaaacatc tgaatacctc ttgagttaat    86760
gcatgcacat ttttattttc ctggaatact gagaaaaagg ttgctacata atgtcttgat    86820
agcttctaag tcatggctca aaagtgaatg tggaatctgc taatcggaat ggactcagat    86880
tcagccaagt tctcaaaaac atttgctttc atagatgtct tcaagaaaca aggagtcttg    86940
aatttaaatt gtgaagtgtc tatcttagaa tagagagatt taaaatctga ctgtattttg    87000
tttaaaaaag cctatataac tgtattatat aaaattattt atactacagt taaaaaaaga    87060
atcccatcct atttgtgcct aaataagtgc ctgcttgtag catgaaaact atttgttgag    87120
ggtccttaga tcctcagagc atgctgtgaa agtaggtaca attgttcttt ctatataagc    87180
ctcttaagat aacagataat tgccagaaat acagcacaca gtacaaaatt accttgtttt    87240
acttttgcca caaaaaacaa tttctttttgg ctttgagcaa taaagtccaa tgattttttt    87300
cctttcaaaa tatcttcctc cctctccata agttttatat ttattcacga aggaatattc    87360
caatatcgga tgttttttgtc tgtgtctctt cctggaacaa atgttaatta atctctttgg    87420
gtttgtatgt caagtggagg ggtgggggatt gggacaggt gatagttgtc tagggagtta    87480
acttcatctc tataggagag tggatagacg ctgtatacga aaagctcttg aaaagggaaa    87540
tacagcagcc acttcctcag ggcttccatg gtggtcagac tccttgattg ctttagatta    87600
actctggctt ttgtccttcg gaggccacca gattgggtgg atagacattg tccttgctgt    87660
tcttttgacc tacctacttg tactttaggg gaaaaaaatg cctgtaatag gttaaatgct    87720
ttctcaaaga tcaccaaagt atataacaca tggcaaatag acagagaaat gagacagtat    87780
aatcagtata atttataaaa gtaccttaca gcaggatccc atgggatatg ggtttttttt    87840
aaaaaaaatc tacctaatct tttcattgaa ctcctattca ggattcatta tattgaatat    87900
ggctcagaga cctggaaaat tgtttccacc ttttaatttt attcaccatc atttatggaa    87960
gttttcaagg acgtttactt acctacctca gttaacagat tgtactactt gggaagtcta    88020
taaatatgag cttaaagcat tttctgagtt taaaataat ttagattgtg tagaatgtta    88080
aaactaaaag aggaaaaat tattcagttc ctcagttgaa cctagcaatt tatctttca    88140 cagtgtgctc aagtatagtt tttgaaaagt aagaagatg gttttatac aaacataaac    88200 acatttcaaa gattttattc aactaattaa ttagtagtgg agccaataag ctggtaagac    88260
tggtttaaag gaatatctga ggaataaaga tttatagaaa cagtcaaaga aattctaaag    88320
agaattgact aatagatata aatctagtaa atatttgatt aataatagca gtaacctatg    88380
gaattatgtt ttctactgag cataaatgag catgaatctc tttgggtttg tatgtcaagt    88440
ggaagggtgg ggattgggga caagtgatag ttgtcaaggg agttaacttc atctctatag    88500
gagagtggat agatgctgta taagaaaagc tcttgaaaag ggaaataaag cagccactgc    88560
acatctgcac atataacctg tagatctggg ggctctaata aaaagttaa tggcaatgtc    88620 aaaatctggt gttttatctt agataacttc atagtcattg attgagcccc ttaaaaataa    88680
catttaaagg acatgtagtc attctgtttc tttattgcca agtttcagc aattttctc    88740 atgagaatga gtgctaagaa acttttggtg gagcgtggtg gctcaagcct gcagtcttgc    88800
actttgggac gccaaggctg gccaattact tgagatcagt agtttgagac cacctggcc    88860
```

```
aacatggtga aaccttgtct ctactaaaaa tacaaaaaaa aaaaaaagtg ggatgtggtg   88920
gcatgcgcct gtaatcctgg ctactctgga ggctgaggca cgagagtcac ttgaacccgg   88980
gaggcagagg ttgcagtgag ccgagatcct gccactgcac tccagcctgg gctacagagg   89040
gagactccat ctcaaacaaa caaacaaaca aaaagaaac ttttaaaata taacaataga   89100
gacattacat aggcccacaa aaccacctcc aaaaaagcat tctatcacct gcaagaaagc   89160
atatatatat atctgctttt gtgtatatat atatatatat atatatctgc ttttgtgtat   89220
atatatatac acacacacac acacatatgt gtgatatcag catgtgtatt tacacatata   89280
ttttgtgcat gtatattttt aactaaaaat gtgctaggag ttagatatga actgattttg   89340
gaggaggtga tatgctgtag agagagagaa tgggagaata gcagtattat aatctctctc   89400
cattgtattc agttttttc tttgtctgaa tttttaatag aagtcagcca gaagatgtta   89460
gtttctggga aatgtgttga gatttacagt caaatccaga gagaactaga ggcttatgag   89520
taaataagta aaggttatgc agagaaagta ttcttttttcc tgtgtaaact tgaatattgg   89580
ccaggcgcgg tggacacctg taatcccagca cttttgggagg ccaaggcggg tggatcgact   89640
gaggtcagga gttcatgacc agcctgtcca acatggtgaa acccattctc taccaaaaat   89700
acaaaaatta gtgggtgtgg tggcaggatc ctgtaatccc agctactacg gaggctgagg   89760
caggagaatt gctttaacct aggaggcgga ggttgcagtg agctgagaca gcgccattgc   89820
actatagcta cggcgataag agtgagactt catctaaaaa aaaaaagaa aagaaaacct   89880 tgaatatttc ttgtacttgt gttcaaatca tacagttatg aaagtttacc cctagctgtt   89940
acacttaaaa tgtacttctg aaatatacag agagatgata cagactatta atgagttcca   90000
ctaaactttt aatggtttag aaaatacaaa tattttctta ttttctgga attccagcca   90060 ttaatgtaaa acattggttt caacataaat aacacactgg catgcacata tgcctaagca   90120 tgggcccca cacatacaga cattctgaaa gaccacttt taaaaatatt cagtaccgta   90180
tattgtgcat tccttctttta tccacatact taagctgctg caagcatccc attgataaca   90240
ccagtaataa aagatgggac catcagtaat gagatttgaa agccccttt gcaagaaagt   90300 aaggactaga aggtggaaat cactctgtct tagagtcata tggattgggg ctttgctaga   90360
agtgtgtgct ctcagggaaa gctgcctttt tatttctcc agagaaaagc cttttgtca   90420 gtaaagaag atgtatcatc caatgcatat gtaaattct aaacagcaga taaacaaca   90480 ttcactatta atctctgcaa aagaagatat attgaaaaaa tcctcaagtg tccctctttg   90540
ggtttctttg ttatatatta aagcagttat ctttagatgc atgagaatca cctgaagacc   90600
ttatttttaa aattcagatt cctgtcagtt cactcccaaa gattccgatt cagtagttaa   90660
gagacaaagc ctaggaatgt gaatttacaa tcaacacctc aggtgatagc catgcatgtt   90720
cttaatgctc tactactatc tatgcataaa aggaagataa agttttaaaa acttgaaatg   90780
tggtataaca gttagtatt gaataatata catttttact tattgtaaca aattatgata   90840
tctacttggg gcaacagtat cttttattt ggatctgaat cctaattttg gctaggtatc   90900
actgagggat tcttagtcta aaacaattaa atggagttag tggttttttt tagtaactct   90960
tgattttctg ttttttcca ttggcatctt acaaatttta ttcattcatt tttccctttt   91020
tcacttggca ttatttgtta gacagtggac aaaagaacta tagaaagtag agaagcatgt   91080
gatgttgtcc tgctcttaga ttctcgcaac tcaggagagg acattcgctt acaccaatca   91140
tctcaaaaca tggcagttta tgctgaactc agtccaatgg gagagcattt gactgagcac   91200
```

```
ataggagag   aagttagctc   tgttgaagga   taatcaacga   agaattctta   ggaaaggtac   91260
agtcattcat  tgaatatttg   ctcggcactt   actaggtgca   tatgtgcact   aagatctaag   91320
gatgggctga  tgaagaaccc   aggtcccttt   tcttctagtg   gacatgcaga   ctggcctaaa   91380
aaaaaaaagg  taactggaaa   atggataagg   aaactgagtc   actcggttta   tttattatca   91440
ctcggtttat  ttgcttttgt   ttgtattttc   attttgacac   agcacagtgt   catcttaacg   91500
catcctccaa  agtgaaggat   ggggtggata   acactttagt   tggcatttct   gtagccagga   91560
gccaggatct  ttctcccata   attgcattaa   cctgggaagg   caccctctag   gtagatttgt   91620
atagcaccct  ggttaatcaa   ttatcagttt   acttcttgtc   tcactaagct   ttaacacctt   91680
acatttatga  agcagtgtaa   atataacttt   agcatcttga   tcacagcaag   cacctgattt   91740 gtatttttt   attagctcaa   gtgaaatcag   atcagagaag   tacattacag   gtcataaaat   91800
atgtgcaaat  ttcataatga   cctccttta   aaatgtgcaa   aaataagatt   gttaaggcac   91860
attccagagc  cttgggggt    gtgtgtgtgt   gtgtgtgt    gtgtgtgtgc   gtgtgtgt    91920 gtgcttgtct  tttgagaata   tctgtatatc   agaaaattttg  gctgagaagc   aatcttcttc   91980
ttagtggttc  ttttctctt    ttgaaaataa   agtactaaaa   atacttaaag   atgcagaaca   92040
gcaacctgtt  cccagtgaga   ctctcgttta   attaatgtgg   tgatctatat   agagaaaagg   92100
gacaattgca  aaagtccctc   aataattatc   taaccacagt   ctttaggtaa   ttacagcaga   92160
aagattttca  agacacaaaa   caccctggaa   atttgacct    cttatttga    ttcaggcctt   92220 tcatttctta  aatattttct   ttaatgttga   tgtttatgct   tgacaaggtc   agcctaatgc   92280
cagatgaatc  cctggaactc   aaaacattgc   tgaattcaca   gttgaaggat   tttaatataa   92340
tataccagct  tttaaaaatc   ctacagtgag   aataacagga   ctgaataaaa   aaattaagaa   92400
atgctcaggt  agaaataaat   agagaaattt   agaaaaaaaa   taaacgtat    tcaaaataag   92460 tattaagcat  tggcaaagaa   aaaatagtag   cagacaatta   catgttccat   ttgtaaagat   92520
gattattaat  tagtggtctt   gcaaaacatt   ggagaaaatt   tgctgaacca   tcacattcat   92580
aaatattaaa  accacccatt   agtgaaaatc   ttttactaa    acttcacaac   tgatagtcaa   92640
ataatgttca  gtttttctcc   attgcaataa   aaaataaagg   cttttgcctt   cagatcagtc   92700
tctgggcctt  attaattcag   tcagccagaa   gccacatgga   aatattttgt   tttgttaaaa   92760
gccagcttgc  cctcatgatc   ttttaaaatc   ttttaaaaat   cttccatcag   ccctctccct   92820
gacttgaatt  atggcagtgc   tttctaaact   ggtaaactca   atctccttgg   tgtgcctcaa   92880
gatagagtac  ataaaccctc   cttagaaatt   gagctctcaa   ttctaaattg   cactctccat   92940
gagagcaagc  aagaatgctt   tgctttgtat   taagtggtca   caatattaaa   tataaccata   93000
gacagcactg  tattttctaa   acaccttatt   ttcttttaat   gactgacata   aattagatca   93060
taagtataca  aatgcatatc   tgttgtattt   ttcagcacca   tgtgttttt    tttcttttt    93120 ctgagttatt  ttcctgcttt   cggcagcctt   ttctctcagg   tgccttgtga   tccacagtgg   93180
tgtgtgttca  cactaaccaa   agcaatagtc   ttacctgcca   gaaatagctg   tgacatttaa   93240
agagaggtcc  aggggaaggc   acagtgctta   acatccaagt   ctgaagagct   aatagtgaaa   93300
ttggggcatc  agctacagag   agatttaggg   gaagtaacag   gcaggttaaa   tattttatgg   93360
aaatgatttc  tgttctgtat   atgattgcaa   ttaacacatg   tcaatctgtt   tcattaattt   93420
gttaactcat  ctattatgct   atgccatgaa   gaaaataaaa   ttggagttct   ttattttttt   93480
gagatggagt  ctcactctct   tgcccaggct   ggagtgcagt   ggcaggatct   cagctcactg   93540
caatctccac  cacccaggtt   caagcgattc   ttctgcctca   gccacctgag   taactgggac   93600
```

```
tacaggtgcg tgcaaccatg cctggctaat ttttgtattt ttagtagaga tggggtttca   93660
ccatgtgggc caggctggtc ccaaactcct gacctcaagt gatccgcctg tcttggcctc   93720
ccaaggtgct gggattacag gcgtgagcca ccgcgcccg ccacaaaact gaagttctaa   93780
gcttcagttt agatgctcac taaatgcttg ttttgcaata cctgactgta actggcagga   93840
atatgttttg aaagtcctca ttttccaggt atgcagatga aatatagggg cattatctac   93900
tatgtcaaat tataatgatt tatcagtggc acatgaaagt cgcctcacat tcttaatca    93960 gtgatatacc attatgtcat gccacctttt aatgtaatat gtttacatct ttctttagat   94020
gtaagcattc atttagttca tcacggtggc tttcacactt actccaagaa cgctatgagt   94080
tcctttgatg tgctcaagtc tcctgcccca gggagaaagg gagtggtgag caggaatcgc   94140
tttaatctat ttacacagat attttctttt ccatttattt taaggaatt ttttttaact    94200 taatgagtat gcagtgacgg tggtgatgat gatgatacta aggtttaaat gattagatag   94260
tcaaatctgg gctggaattg taatactgtt ttgacttta atcttagaga agctccagtc     94320
tgcttatttt ctgggcataa acacatgaga acaataacac agttctgtta tctgaatgtt   94380
gttatatttt gtttgaaaca ttcagtgact ttcaaatatt gtatttgcct aagaaaattc   94440
aacagagtca gacattctct tccaggttaa atttggtgag tctgctagga aataaattt    94500 tgtgcactgg tcattctgat ctagtggacg ttctaataaa agcacctttg tgctgcctac   94560
gtcttcactt taaagataag atacctgggt actcgacacc aaattatagt ttgagatctc   94620
aaaaatggga tagggaaacc acagctcaaa aacaaaaata ctagcactgg aaaagataga   94680
actagtgaag atgaatcatt ctctagactt taaattcaga gatatcaaaa ttaagaaaaa   94740
gtaggaggaa taaaaaaga gggtaagcaa aacaatataa gtttgtatag caagagggta   94800
taaagcaaat acaatatttt tcagaaaaat taaataaaaa tagatttaca taacattgtt   94860
tttaatctca aagatcaaat ttcaattttc atctcatttt aaaacccata tgcacagtct   94920
cctttatata catcagttgg gtgtcaaagt gacttttttc ttgtttccaa atacagttat   94980
ttttaaaatt taattgtatg atttaggaat ttgaaagcaa gccagtttgc acacacatat   95040
gttattatat gtgtgcttta gacttggttt ttagttaatg taacatgaca gggccacctg   95100
agttatttgt ttacaaacta gctggaaagc caccctggag gagaaacctg gcaacaaaat   95160
ggtctgcagc tttgttattg ttatctatag gattggatgc cattattgct gtaaaatagt   95220
tcacaagaac tcagtctatg ggaaagactc aaaaattctt tgcctgttaa agaaaaatca   95280
ggatattgga ctggttagtt taactaaaaa gtgatgatac tcagattctg cttggattca   95340
ctgcttctca gcagttgttt tgtttctttc taattgatat tttatttttc agagaaccca   95400
ttataaaact cttcttcttc ccttaaaatc acaaccacac aacagcaatt aaaacatgct   95460
ttgacgtaag actgatatgg ttttaaaccc agcttgacta tcgaattttt tactttaggc   95520
aaaacacctc tgacatttat gtcttatcgt cagtaaaaag gggtgattaa cagttttaca   95580
agattattca ataaataaat ataaattcct cctttccctt cctttccttt cttcatcttc    95640
agcatctgca tgccataagc tcattttagt tctctggact catgttaaca tgtcccacct   95700
ttcccaaatt aaacatcatc tctgttattg gctccattct tttcctctca tttgagacaa   95760
ttctttatca accaacaccc tctctgctct gtattgtgaa actctgctcc tactacatta    95820
acagtctctt ggtttctta aaagaagac aaaacaatta aagaacagaa gcaaaaaatc       95880
tactcaaatc cccaattgtt accctcaaaa ttaattgtcc caccctagc tttctcattg      95940
```

```
cacaactctt tgtcaaaatg ttttctacca tcacagcctt caatgatctt tctggttcct    96000
ttatctcctg aagtctgact tctacctcca tcttttttctg gactattcaa cacactttga   96060
gaaaaaacat acttttgtta aacaggtatg catccctgaa gcataaaata catagtactg    96120
aaagtgcaca tgtgtggttc ttcccatttt ttttacagca cttgaaactg acaagtagta    96180
gtaccaatta cttagtaaaa gacctttttc atttcatttc tgaaatattg ttattttcct    96240
ttttcatctt ccatctctga ctacacctcc aattttacct ctttgctgcc ttccttccta    96300
agaaagttct tcatgcaatg ccatcttgtt tttcttcact tgcctctttt tctcacttta    96360
attttatgaa ctctgatgac ttacctctgt agtgtaacta ctcaaaatat gtatttctga    96420
agtctcaact ccaatctcat attttcaact tatatttatg gaggcatctc agactcaacc    96480
tacctaaaaa atggcttatc tgccctaaaa tctactttgt tcttttttttc tctactgcta    96540 ataattatct tcctagttgg tcaagctcaa aacctaatca tttttactcc ttgtccctgt    96600
gtcagctgtc cacattcaag cagcgtatca tttctgcaca tttttcaagc aagtcagtaa    96660
ctgccttttg tttgggactg tcttttcata tagtgaacag ccttggaaga tagaaatcat    96720
ttctccttct aaaacaaaag gcaggtgtgc ttgcagcctt ggatagaggt agtgcctctt    96780
tctaaagcaa agggacatct ttactggcca ttataaaata tccatgtttc ctgagctctg    96840
cgttcctctt ttctaatgca acccactgag catgtaggtg tcacctgagc ttttctgtgg    96900
gaattgcggc ttgaggaatc agtgcaagaa aatcatgata ctcttgctaa tgctattaat    96960
gtgagtagta aagttaattg tctctgaccc agcactattg tgtctttgcc cagcactcaa    97020
aagactggca ggcttgcaag taggacaaaa tgttagattt ttcacagttc ttctgcttat    97080
aagtacttgt taaaaccaat taaaacacaa cttgtagttt gcacctataa ttttgtagca    97140
tttgcttctt atctatgtca ctaggatgtg cttagtgaca gacccatcta tcatctatta    97200
ctcaagtttt tggctgtatt cctaggcaac agagagaagg ggaacaaaca agaggacctg    97260
tgcacagttt gagaaaggca aaacaccgag cttaattgca gacttgaatg tagctagcaa    97320
acgaagtaag gcaaaaggtt cctttttttt tttttttagat ggagtctcac tctgtcgcca   97380
gtctggagtg cagtggtgct gtctcggctc actgcaacct ccgcctcctg ggttccagcg    97440
attcttctgc ctcagcctcc cgagtagctg ggactacagg catgtgccac catgcccagc    97500
taacttttgt atttttagta gagacggagt ttcaccacgt tggccaggat ggtctcaatc    97560
tcttgacctt gtgatccgcc cattcggcct cccaaagtgc tgagattata ggtgtgagcc    97620
tccgttcccg gccaaaagtt tccatttttt aaatagttgg gttttttagtt tcgattcttt   97680 ccaaaaaaag gttttcttaa aaaaataaaa ttagcaataa gatgaaatat aacaacaata    97740
taatcttatt aagacaatat atgatataca tttatcaaaa tacttatatt ttcaaaagtg    97800
cttaaaataa tctagcacat agtagatgct cagtaaatat ttgatattat gactgtgcat    97860
gggtcattat aggctacttt atgtatatca tttcatttag tacaacatca ctctgaaaaa    97920
tgttttattg ttaccgtttt tcagttgaaa catttacgtt gctcaagatc tcactggtac    97980
catctactat taggtcagtc tgccaccaaa tctcatgctc ttaaatgccc ttttttctcct   98040 gagcttccaa caaatagtgt actgtatata attgttgaag ggaggggact gtgagacaaa    98100
atatttagag tgaatgtgta gccacaattt cagttcctca acaaagtgat aaaattagga    98160
atcatcctca atatatattc ttccaacaca cacacacaca tacacacaca cacacacaca    98220
aataccacaa gcccacttga atgcaccccca cctacacatt gcaaccatag agacaattgc    98280
agcattaaat acagaatatt ctgtgtgttg tttgtttgtt ctcccttttgc tacaaaaatc   98340
```

```
agaatttcta ctcaataaac agcaaaggga gatacaaatg aaccaaatta aagaaggaaa   98400
aaatgttgaa aaaattatat acagaactat gtattgatt tattgagagtt cagtaatgta   98460 atccagaaat aatggatgcc ttaaaagtaa ttaaaagaat gcaaataaac atttagtgcc   98520
aattaaagaa aaagaaatac aacattagac aaaataaaag atattcattt gatgcaatga   98580
ggaaataatc ttttattcct ctttaaattc tctgtggaat aaggcatggt tataaataaa   98640
taaacatctg ccccatggac ttaatggatc gttatatttt attgcgataa tcataatgaa   98700
attgttggga gggattagta tctctagtgt aatgctaaga aagataaagc ctgtgcccag   98760
gcaaaagctt tcttggttgg tcaaaaggtt tgaagacatt tcaaactatt ctaaaacaaa   98820
caaacaagca aacaaacaaa aaacatacaa tgtctttgcc acatatttag gaaacaaaat   98880
gaacaattta tttctgacaa cctcatagtc tttgttctgt cagaacaata atggaaaggt   98940
ctaaaccaga aaatgctatg cattgaattt ataataaact atttttttcct gtaacaaaaa   99000 attgataaac ttgatatttg cagatttaat gattatgtgt ttaaaaaaaa tctggttttt   99060
gcccttgcaa aaaatcatat atatacacat agatatgtat gtgtgtgtgt gcatagtata   99120
tatatatgta tatacatata tatacacaca tttatatata taaacatttc ctttaacctc   99180
ctattttatt ccaataaaaa tattggtatt agagatagtt ctgatatttc atcatgaata   99240
gttaacattg catttgggaaa ggattaattt ttttgaaacg taattttacc ttaataagta   99300
gcccagcgta atatttagt aattacacag attttttttt caagacattt gacaactaat   99360
attgcataat agttaagagt gtgggctttg gagccagact tcctatctct gttcattcac   99420
tgataaaatg gagacagtag taacttcctc aaagagttgt ttttttaagat caaataatgc   99480 atataaaact cttgaaatgg taccaaatac agagtaagca ccaaataaac attaactgtt   99540
attgttattc catgtccgaa taacacagaa aagtaagaat tttaatattt catttgaatg   99600
accttttaag gatacaccta gcccattatc tttcttgata atcttgtaag atgattcctt   99660
ttttatctcc gatctgttga ggcatggata gaggttttca gagaaaacat tttctaggta   99720
actgaaagaa agtagcaaca acaaactgtg acaaaactta acaatgagag aatttacaag   99780
atagaataat tgcaactcct tttgaaatca accactatgg tcctctggct gggatagcta   99840
agcaaagata ttccagcctg aaggttgaga tctacttgaa gagttttcta tccagattgt   99900
gagggcccct caaacttcac ttagtatctg tttctattag tatggaaact tctgaaacct   99960
tgtggtatca cattcacttg actactttat tcctgctcta gctatcttaa agcctttctt  100020 aatctttat cttttagaga agatacttct aggttttaaa tccaccgatc ttgaagctat  100080
tgccttcact ctctgcttca gagcccatcc ttttgtatat gagtagtttg ttttgcctaa  100140
agtactttct cccagtcaga ttttaagtcc agtttctcat ctgttttttga gagcaaactc  100200 ctgggccttg gctcactaac atcttgacag catatttctt cttttcctatg ggcttttcag  100260 cattccctgg gtttttctaa aatatgaaag cagactcttt atctcttact ttgtcaaagc  100320
ctaccctccc cactgatttc tcacccagtt gctagtttta agacctgcct ctggccgggc  100380
gcagtggctc acgcctgtaa tcccagcact ttgggaggcc aaggtaggtg atcacgagg  100440 tcaggagatc gagaccatcc tggctaacac agtgaaaccc tgtctctact aaaaattacaa  100500 aaaaattagc caggcgtggt ggtgagcgcc tgtagtccca gctactcggg aggctgaagc  100560
aggagaatgg cgtgatcccg tgaggcagag cttgcagtga gctgagatcg cgccactgca  100620
ctccagcctg ggcgacagag cgagactctg tctcaaaaaa aaaaaaaaaa aaaaaaaaaa  100680
```

```
aaaaagacct gcctccaaat atcattgtat ttgcaaacat gaaatgactt attgattctg   100740
agctcagcac aagagcaaac ctttctcagc ttgacccatc ttcacatcgt taatgtctta   100800
ttcagtcact acccaagggg ctgaccttca agattctaat ccatgaaagc ttaaaatagt   100860
aaacaaattt gaatatagtt taacatacat aataaatttt atttctagaa gaggaggatc   100920
agcccttaga catgaaaagt aaaaatagtt tattcccaga tttcccttttg tgcattagta   100980 tattcaaccg agtctatcca agtaacagga caaaaaaagc tggcagttgt tgctgcgctg   101040
tgaagtctta ttaggtgagt cagctaatta tatggcacta ccataaatac agcaggcact   101100
gccctgcttg ttaggcttgc caaggaaaat aaggatttaa agcagcatac tacctctttg   101160
ctatataatg acattttctt cttaaaaatg attttgcacc aattcctgat ttatccacca   101220 attattttttt aatttatggt tgaatgtatt taaacctgaa ttcagagata aaactagtaa   101280
atagctcccc aaaataaccc caaatatatt taatatatta gctttactct ctcctccact   101340
gccaaacctt taaaaactga aataaaattgt ttttatttca tcttttctct ttttctctct   101400
ctctaaggtg attgccaaga ctaaagaaac agctagaagg gcaaaagaca agaaaatcag   101460
taagatagta acagattatc caaagtagag cacggctcag gtgcagtggc tcatgcctgt   101520
aatcccagca ctttcggagg ctgacgcagg aggatcactt gagtccagga gtttgagacc   101580
agcctgggca acataatgaa acttcatctc tataaaaaaa aaaaatttaa atagccgagc   101640
atggtggtgt aagcctatag tcccagctat ttgggaggct gaggctggag gatcacttgg   101700
gcccaggagt tggagactac agtgagctat gattgtatca ctgcattaca gcctgggcaa   101760
tagggcaaga ccctgcctct aaacaaaaga taaacaaagt agagcataaa tggcttctaa   101820
atatatgtta tttatgtgta agactgggtt ctctaaaggt atcatttaat taaaatagat   101880
ttgcattctc aatctgtagg tatggattat gtataatgta tttaagatat gacttacagc   101940
gttcaccaat gtgactattc ccaagtgatc cagatggctg atgacatagt aatttgtaca   102000
tttgctgaga cctgatctga gtaggtatgt aacataactg agggagagca agtccatttg   102060
ccgaaagaaa gcctagcata tgacccagga gccacatctt cactcagcct tgttgctagg   102120
tttggcttag catatataat agcatagcat gtataattta tgacaaaaaa ttatactttg   102180 cacttttttaa ttagaacatt caaaatgatc tcaggaagtg gcaccagaga tcatcagtgg   102240
tctactgtac ttcgtgtgta tgtgtctgtg agtatgtatg tgtttgtgtg tgttcccaca   102300
ttctaaggca tgtcttttac aggttagtag aaaatgttga tagaaaatta tagatttcaa   102360
catctaaaac acagtaggtc actacattgt taaaacttgg aattttttat cttgttgtaa   102420
agtcaggcca accaaaccta aaatactgct acattgaaat agtgcaaaat attcaaaata   102480
ctatagttat agatttggta gtaggactgt accagacctg tcactctata caagacttat   102540
gccttgccct ttcacttacc tgttcccttt tacatctatc ttactagatg taatgctata   102600
aattatattt ctaatatatt ataatttatc atgtattata atgtatcaaa tattacaaat   102660
tatgttgcaa ctccccttac ctttcgtctg catattgcct cagaaagaac agatggatcc   102720
aacagacttc aaccacaggc ccttagtgac aaatagctct taatgctggg cttgccactt   102780
tgatgcattt ctaaagttat agaatgttaa atgcaccaag tcctttggtc attttatttc   102840
taccttagat ctaagccata actatacttt cccaaaaatt aaagtttgaa ttttaactta   102900
accatatata attggaaaag gaggttgggt tcgttaagtg taattttatc atgctttatt   102960
atcctttggg cattggatac agcagaacat gccaatttct atggcttctc atgtgacaga   103020
atatacttac taggatgcaa ttaaatactc ctcagagtat gtaaacaata aatgtaatca   103080
```

```
ttacattatt tttatattgt tctttcttat gcataatagt aagactgaaa atatagtgtt    103140
atttctgaaa tatgcatatt gttttgcttt tgatgattaa ataacattgt ccaaagtttt    103200
aggttttttg aaatcttata tttttaaca aaatatctag cctttccaaa acaagacctc     103260
aataattcgt ttaagaccca gagttgttcc tctccacata gatctcttaa aaaggcagag    103320
gatttatgac ctcaagagaa atcagagtat ccaaagtttg ctttaattca atgttttaaa    103380
aataaaattc cttagatttt atcaaaaatt gagattagtt tgattttgaa tcagatgccc    103440
tttgctcccc accccaaaat ggcattatga gcagactagg aattgataat agaaaattga    103500
acatatgaaa tatatcttta ccttgctttt taacaaggta ttcatgtcta tcgccttcat    103560
ttttaagtgc atcaataaaa tacatggtaa ttctcttagt gaaatatact atctacacta    103620
tgtacacact cccctgtctg aggtagagaa gtagagaata ttcacatttt tgaaacgtct    103680
atgctatttt tatttaaata cgagttctgg gcttgatttc attttggaac acgggtgtgt    103740
gcttaagttg aaccttttt tcctcttaag tcaaagttct tttttagttt cttcttttat     103800 cttttggct actatctctc tccttcatcc tcctggtgtg agttgttgag tgaaggtatt      103860
aattccatta tttgaggcta agtgacattg ttcaataatg cagcaaaaca atggttctac    103920
ccaaaatatc ttcaagtgta aaagcagtgg gcaaagaga aagtgcgctt ctgctgcttt    103980
gaatgtttaa ggctgtgaaa gttgatcaca caaattgggt cattcttgtt atcccaact     104040 aaaacaatca agaagcctgg gaggaaaagc attcaagaaa catcacattg ctccaaaagt    104100
gtaattttct acaagtccgc atgctgaggc tgcctgttgt aacctgggac caatttttc     104160 tgtaactgct gaaaaaactt gctgcagctc taggactaat tttgcccacc actgtcactc    104220
accaattgaa gcttactagc tccccagaac ctttctagtg ccaatgaact ttctcaaaga    104280
gcagcgtgta tcatttctct ttttcagaac acctccaacc tcctcttttgt tctttgggta    104340 taccaaagac caaccagcct tgaatttcaa ttttcttcc cacataaaag ttttaattta     104400
gaaatgtatc tctacatttc taactttgac aaagcataga taccagataa ttgatgaaac    104460
cttgctattt taacgatcac catgattac ttcccagtgt cttcagataa ccctcaacat     104520
ttgccaacat ttgatggact tcaaaatgag catatctttt taaaaaaaa ttattcacac     104580 tgacagcaag tacattggta tactctatat taaattatac cacagggttt acaaacaatt    104640
ggtgatgtcg ggcagtggtt tccaaggaac atacttaaca agacactcac aaggccctac    104700
aaacctgcat ttttaacaag ggccctagat gattctagaa gagtgtggtt tggaaagcaa    104760
tttttgcctt tattatgtgt cattttaaat atatttaaaa ttaaagttat aagtcataga    104820
attgaataaa gataatttcc ttacagaaag tattactagg tatctaaata caatatggtt    104880
caaaacagga aatttaaaaa gattatgtaa attctgtagt tgtattccta aagacagtag    104940
ctgaaatttt ttcctacttc tccttgtatc acttcccttt tccttcactt tcacttccct    105000
ggaattgtac ttcccaataa gctattagca gtgaaggaag cttcgtctca tgatctgttt    105060
tatagagcac ttcagctggg acgagtacga aatgataatc agttatatca gctattcaac    105120
cctacaggtt tatttaaaaa gaacttgaat aagcttttta gggagaaaga ggtcagtctc    105180
agccatttct gtttcctaat atagctttta agtctttcct tattagcaat gagggtcatt    105240
ccattgtaat ttttttgataa ccattttctt ttctgtgtgt caaatgcaga tataagatac    105300
tgaactgagt ctatttcact gttcgtaaaa caatcccatt tgaaaaaaaa aagtctacag    105360
ctattccagg gatagggcct agtagagaga gaataaaagg tattttctta ctatgtctct    105420
```

```
atatcctacc ctgtaggttc tcttattaag catacaggca tataccaaaa tccagacgtt   105480
tttctcattt attttattgc cctaacatat tctgggttaa tataatatca taatgaaaat   105540
ttgagaaaaa attgatttt tcaaaagtgt ttaacatttg ttatattggt agttttttt    105600 cttgtttgtg gtaaaaataa atagaaggtg cacttcacac cttcaagtat gattatattt   105660
tgaaaacaag tcatgaatac tcataaaatg caaattttaa tgttcttttt ttgttacagc   105720
caaactatat taggcacagt tgtaaattgg agttgaaatt taatatttct ttatagataa   105780
caatgttttt agaaataggt ttatgaaaca gtaaatatac aggtataggg ataaaattgt   105840
gtctgatggt catatgaagt gtttgttgtt atattctcct tggaatagct gccaaatatt   105900
ttagtatgct taaaatctac gaatgtgata gagtcaacaa atttagatca catattcaga   105960
aaaacatagt tagagaacta actattgaaa tgagcataca gcagtcttcc tttatctaca   106020
gggatacatt ctgaaacccc cactaggaca cctgaaattg cggatagtag caaaccctac   106080
atatactgtt ttttccaatg cttatgtacc tatgaaaaag tttaatttat aaactaggca   106140
cagtaagaga ttaacaacaa taactaataa caaaagagaa caattataat aatatactgt   106200
aataaaagtt atgtgggtat ggtctcgctt tctctttccc tctctctctg tctctaaata   106260
tcttagtatt ttggggttgc aattggtggt gggcaactga aaccatggaa aacaaaacca   106320
cggataaaag gagactactg tatatacttt ttaaaactga tgaaatatta aactcatgtt   106380
tcttctatat cccacccatt tcccccaccc aaacctagat agatatctta tttgatctgt   106440
aaacatttaa ttaatttgta aaagttaaga acttttttgaa gtaaaactgc aatatatcat   106500
cacacctaaa gaaataaaca ataattctta aatatcaagt cagtgttcaa atttccccaa   106560
ctacctcata tgtgttttcc atttgcttat gtagggttcc caatgagaat gaaataaagt   106620
tcttaggttg caattggcta atgctctctc acttctactt taagcggcag gttcccacta   106680
acttcttttt agttgcaatt tacttattga aattagacgt attctttgtc ttgtgtagtt   106740
tctcacagtg caaaatttgc tgattgtagc cactgttgta agcaatgaac atgttttca    106800 ccaccttata tttgctgtaa gttgtcagtg atagttaaat gttaatcaaa ttcaaattcg   106860
gatcacgtag ggcttttctt tttttgtttt ctttttctat ttatatattt atttatttat   106920
tttgagacgg agtctcactc cgtcaccagg ctggagtgca atggtgtgat ctgggctcac   106980
tgcaatctcc acctcccggg ttcaagtgat tcccctggct cagtctcccg agtagctggg   107040
actataggag aaccaccacg cccggctaac ttttttgtatt ttagtagaga tggggtttca   107100
ccatgttggc caggatgcta tagatctcct gacctcaccg atcatgtagg acttcaattg   107160
tcgaacaaac gaacctttaa tagcagttac accattagga tgacctgatc caacatcgag   107220
gtcgtaaacc ctattgtcga tttggactct agaataggat tgtgctgtca tcccagtgt    107280 agcttgttcc cacttgatga agttattgga tcagtgaaca atagcccact taaactagta   107340
cagtcttagt ttaagatggt gatgtgtatg tacttccatc agagggcaca taatacagta   107400
aatcctcact taacttcatc aatagtttct ggaaactgtg acttgaagca aaacaacata   107460
taacaaaacc agttttacca ttggctaatt gatataagca agaattaagt cctatggcaa   107520 attctctggac acaaaacac catcaaactc ctaaataaag ataaatcact tctgacatta   107580
aacattgaaa ttaatgtgag ctatatatac gtttaagaaa gattaataca aacaagtcaa   107640
ataacttacc taattatttc ggtggaggcc gcaggtggtt ggagcctatc ctggcagctc   107700
agggagcaat atgggaaccc accccggaca ggacgctgtt ccattactgc agggtgctct   107760
tgtacacacc cactcaccca ggctggaacc atgcagacac acacactcac ctaacctaca   107820
```

```
catctgtgta catccttcaa agttcagcca aataacatat aaacaaatcc agtaatatcc   107880
atcagtctta gttccgtcat aacaactcct ttttgatcat caaacaacaa acagggtagg   107940
tctgccatat ttacttgtct ggtccatatc aaaattttct aacaaattat attagaaaat   108000
caaatctctg tcagtttcaa aatcatggaa aaaaatttgc cttatttccc ttatacttgg   108060
atatcctaac agtaatctaa atattaatga gaaagttaat gatgtcgttt ccttctccct   108120
gttgtaaaga aggttttgct gtcccgtttg atcactaaga ctaattgaca ctcagaaaaa   108180
gcataggaaa cttctcagca tcacaaaagc tctgtcatct agagaagcta ggacttgagc   108240
tcaagtcctg tgacatggaa ggccttgtgc ctagccatcc tgcagcagag gcgtatctac   108300
caagaagtga aacactacga aaacagtatg tttactccac attttaaagt gaggtagttt   108360
ggggtggttc atattttatt taatttatat attatttgga tttttttttag tttataaaaa   108420 gggcattggc aagggcagaa tgatctgtaa gcttctctgc ccacctacca taagcatgat   108480
ctttagtgtg acctttcctt actgttagcc attttcttat acttctgcgt ccctgtcagt   108540
cacttccatg tgaagacatg gggaagcttt tttacatcag acatgttgtt gaaaatcagc   108600
cgcgttggct gagggattat ttgatctctt tctccaagtc cctttaggct cacattgcct   108660
ctctgttctt tgaattttca cttacccttta tcttcttata attactttgc tgaaataaat   108720
gcaaagcaac aaaaggtatt tagtgaagaa taccaacaaa gccatgacca tttcaggctg   108780
agttttgtag tattctttgt ctaggaagag atacctagaa aaattttctg accatgtatt   108840
tgattatttt ccttcaatat gtatagtctc agtcttcaaa tttcagaaaa gaatttgttt   108900
cttcattgtc atttaaaatt aatgtgttaa atatgtatgc ttttacatta taagtggtta   108960
taaaagttaa acacttagaa aaaagtcaa aataacatac atactatcca acaaaataac   109020
tttcatattt tattgtgttt tcttccaaac ttttacctt tgcgtctgaa ttctgtgtag    109080
gttgtatcta taatatagac aacactttat agcctgctaa atattatacc ataaataggt   109140
agttgttaca taattctcag gtaatagtaa tacaggtctt tatcataatc tactgagtag   109200
ttgaatgata atttttttta agacaaggtc tccctctgtc acccaggcta gaatgcagtg   109260
gcatgcacat ggctcactgt agcctctacc tcccaggctc aagtgatcct cctgcctcag   109320
cctcccaagt ggctgggact gtaggcatgt gccaccatgc ccagctattt atttgtattt   109380
ttagtagaga tgggggtttca ttgtaacagc ccaggctggt cttgaactcc tggactcaaa   109440
tgatccacct gcctcagcct cccaaagtgc tgaaatcaca ggagtgaacc actgcaccca   109500
gcaataattt tttaactctt cattattcat tgaacattta gttaacaatt ctaaaaattt   109560
tgtttcctgc tgtcattgat cttgtgaaaa atatctttgg actatagctg tggattattt   109620
cctaaatagt aaaattacttg agcaaaaagt ttacatactt tgagggttga taacccatgt   109680
tgccgcaatg tttccccgga ggcattgtgg agtttagaat gccagtagta atattaaggt   109740
gtgccatttt caagatccgt ggccaacatc cctatatgta agattttttcc aaaacatggt   109800 tctgattttt aaaagtgaaa aatgctactt catcatgttc ttttttgtgct tcttacttta   109860 aatattagaa tgaagaagga gccccacagg aaggaattct ggaagatatg cctgtggatc   109920
ctgacaatga ggcttatgaa atgccttctg aggtaggagt ccaagctgaa tctttctaac   109980
aagacagtac caaaaacctg tcattgtcac atttctcttt cattagtgct tagtgagaat   110040
catttgctct ctacatgctc attacgtgga caacttgcaa gttaagaata gttttttacat  110100 ttttaaaggg tccttaaaaa aaaagaggag gaggaagatg aagaagagga agaaaggatg   110160
```

```
taaaagaaat catatgtagt ccacatagct taatatactt actacttgac cctttacagg   110220
aaaagtttac taaccccctgc attagagaat atattttttag aaactttaca ttctaaaata   110280
aatttctaaa tggaaagtta gggaaatcaa tggaatgcca aaggaaggtt attatttttt   110340
gccatacatg tccaatggga tgacgcatag taaaataaaa gttacccaca caagttatag   110400
aataaaaaga taaatgcatg atttgcgaca attgatatat tccagtataa tgttttaaac   110460
aacacaatat gattgttaat tttattttga ttgaaaatga agtatctttt aatagaaaat   110520
gtatcaaaag ggaaattaga aaatactgtt agatgaataa aactggccca agaagaaaca   110580
gtaaatctga atagatttgt aacacagcga atagattaaa ttagtaataa aaaaaaaaac   110640
ctacctgcaa agaaaatccc aggccgagat ggcatcactg gtaaattcta ccaaacatttt   110700 aaagaggaat taatactaat tagttaacac caattaatat ctcttacaaa acagaagagg   110760
agacatttcc caactaattt tgtgagacca atattcccct gataatcaaa accaaatgaa   110820
gatatcacaa gaaagaaaac tatataatgg ctccattaaa aattgagttc aagtatgttg   110880
tagtttggtt atgtattatt cctcacggca ttattaaaag gcatgtcgag gatgggcaca   110940
gcagttcaca cctgtaatcc cgcactttgt gagccaaagt ggccaggtta cttgaggcca   111000
ggagttggag accagtctgg ccaacatggt gaaaccccat ctctactaaa aatacaaaaa   111060
ttagccgggc atggtggtac acgcctatgg ttccagctac ttgggaggct gaggcatgag   111120
agtcacttga acccaggagg cagaggttgc agtgagctga gatggcaccc ctgcactcca   111180
atcttggtaa cagagcaaga ctgtctcaca cagacacacg aaaggcatat tgataataat   111240
tcaacttata gaaattgaga ttaaattgtt tgtttgccta ataagaattt ccaatatttt   111300
ggggtctttt atgcaagaca cagtactaaa cacaatggaa aactatagag taattgacat   111360
taccaggaca taaggagttt acagtctggt aggtttgatg aaaaaaaata gaaattcatt   111420
cattcatttc ttcattatga ttcctttaac aaacataatt gattgtcttc gatgtaccag   111480
gcatcacagg agcaaaaata tataagacat actaaaagt aaaacatttt aaagatctgt   111540
ttcaatcaat caggagaagt tttattgagg aggtaatgtt gatctgggtg ggaaaaggta   111600
agagatatag taggtcaaaa caaacagagg acattctggc acaagggaat atcagaagca   111660
aaggcatgta tgtctgagca tgcaaatgga tatgtctgag aacagtgaat aattatgact   111720
caagcttagg aacaaggaaa atggtgatag attgaatttg cagctatggg tcaaagacaa   111780
gttatagagt attaggataa tcttgtcatt tcagcttgta ttctattcag aaaacaactt   111840
gagttattga agttatgctt atttgtttgt ttttaagcag aatcctgata ttattagagt   111900
tgctctttag gaggaataat ctgatcccct taattaaatc cattaatatt tgtgttgtgg   111960
atgctatcca gatactgtat ggagagcttg aggtttgaaa tacaagtaat aattgaagcc   112020
atagatgaag acgaaatttt caactgggag agtgaaagta gggaaaatgt atcttgcctt   112080
caaacatctt aatttccttc tgagaattag agcatcttag tctggaaaag gctttataga   112140
cagcttgatt ttgttctcac atttttacagg tgaagaaact gagaaccaga cagtccaact   112200
tatttgtcct accaaactag gtatatgatc attaaatggt gcatccggat cagaacctag   112260
atattttaac tctgactact actgtaattc acttttatat cagacaagaa agacacaact   112320
attaaaaata agataatatt tgctgcagaa tatttgcaaa acattgatt gtaaattta   112380 gtgtaagtgg ggagccattt cctatctcat tggctgtcag tgctgatgcg taattgaaac   112440
ttatactaac agtgtgtgct gtctttttga tttttctaat attaggaagg gtatcaagac   112500 tacgaaccctg aagcctaaga aatatctttg ctcccagttt cttgagatct gctgacagat   112560
```

```
gttccatcct gtacaagtgc tcagttccaa tgtgcccagt catgacattt ctcaaagttt 112620
ttacagtgta tctcgaagtc ttccatcagc agtgattgaa gtatctgtac ctgccccac  112680 tcagcatttc ggtgcttccc tttcactgaa gtgaatacat ggtagcaggg tctttgtgtg 112740
ctgtggattt tgtggcttca atctacgatg ttaaaacaaa ttaaaaacac ctaagtgact 112800
accacttatt tctaaatcct cactattttt ttgttgctgt tgttcagaag ttgttagtga 112860
tttgctatca tatattataa gattttaggt gtcttttaa tgatactgtc taagaataat  112920
gacgtattgt gaaatttgtt aatatatata atacttaaaa atatgtgagc atgaaactat 112980
gcacctataa atactaaata tgaaatttta ccattttgcg atgtgtttta ttcacttgtg 113040
tttgtatata aatggtgaga attaaaataa aacgttatct cattgcaaaa atattttatt 113100
tttatcccat ctcactttaa taataaaaat catgcttata agcaacatga attaagaact 113160
gacacaaagg acaaaaatat aaagttatta atagccattt gaagaaggag gaattttaga 113220
agaggtagaa aaaatggaac attaacccta cactcggaat tccctgaagc aacactgcca 113280
gaagtgtgtt ttggtatgca ctggttcctt aagtggctgt gattaattat tgaaagtggg 113340
gtgttgaaga ccccaactac tattgtagag tggtctattt ctcccttcaa tcctgtcaat 113400
gtttgcttta cgtattttgg ggaactgttg tttgatgtgt atgtgtttat aattgttata 113460 cattttttaat tgagcctttt attaacatat attgttattt ttgtctcgaa ataatttttt 113520
agttaaaatc tattttgtct gatattggtg tgaatgctgt acctttctga caataaataa 113580
tattcgacca tgaataaaaa aaaaaaaaaa gtgggttccc gggaactaag cagtgtagaa 113640
gatgattttg actacaccct ccttagagag ccataagaca cattagcaca tattagcaca 113700
ttcaaggctc tgagagaatg tggttaactt tgtttaactc agcattcctc acttttttt  113760 tttaatcatc agaaattctc tctctctctc tctcttttc tctcgctctc tttttttttt 113820 ttttttaca ggaaatgcct ttaaacatcg ttggaactac cagagtcacc ttaaaggaga  113880
tcaattctct agactgataa aaatttcatg gcctccttta aatgttgcca aatatatgaa 113940
ttctaggatt tttccttagg aaaggttttt ctctttcagg gaagatctat taactccca   114000 tgggtgctga aaataaactt gatggtgaaa aactctgtat aaattaattt aaaaattatt 114060
tggtttctct ttttaattat tctggggcat agtcatttct aaaagtcact agtagaaagt 114120
ataatttcaa gacagaatat tctagacatg ctagcagttt atatgtattc atgagtaatg 114180
tgatatatat tgggcgctgg tgaggaagga aggaggaatg agtgactata aggatggtta 114240
ccatagaaac ttccttttt acctaattga agagagacta ctacagagtg ctaagctgca  114300
tgtgtcatct tacactagag agaaatggta agtttcttgt tttatttaag ttatgtttaa 114360
gcaaggaaag gatttgttat tgaacagtat atttcaggaa ggttagaaag tggcggttag 114420
gatatatttt aaatctacct aaagcagcat attttaaaaa tttaaaagta ttggtattaa 114480
attaagaaat agaggacaga actagactga tagcagtgac ctagaacaat ttgagattag 114540
gaaagttgtg accatgaatt taaggattta tgtggataca aattctcctt taaagtgttt 114600
cttcccttaa tatttatctg acggtaattt ttgagcagtg aattacttta tatatcttaa 114660
tagtttattt gggaccaaac acttaaacaa aaagttcttt aagtcatata agccttttca 114720
ggaagcttgt tcatattca ctcccgagac attcacctgc caagtggcct gaggatcaat  114780
ccagtcctag gttattttg cagacttaca ttctcccaag ttattcagcc tcatatgact  114840
ccacggtcgg ctttaccaaa acagttcaga gtgcactttg gcacacaatt gggaacagaa 114900
```

```
caatctaatg tgtggtttgg tattccaagt ggggtctttt tcagaatctc tgcactagtg    114960
tgagatgcaa acatgtttcc tcatctttct ggcttatcca g                        115001
```

<210> SEQ ID NO 3
<211> LENGTH: 1096
<212> TYPE: DNA
<213> ORGANISM: Homo sapiens

<400> SEQUENCE: 3

```
gaattcatta gccatggatg tattcatgaa aggactttca aaggccaagg agggagttgt      60
ggctgctgct gagaaaacca acagggtgt ggcagaagca gcaggaaaga caaagagggg     120
tgttctctat gtaggctcca aaccaagga gggagtggtg catggtgtgg caacagtggc     180
tgagaagacc aaagagcaag tgacaaatgt tggaggagca gtggtgacgg tgtgacagc     240 agtagcccag aagacagtgg agggagcagg gagcattgca gcagccactg ctttgtcaa     300 aaaggaccag ttgggcaagg aagggtatca agactacgaa cctgaagcct aagaaatatc   360
tttgctccca gtttcttgag atctgctgac agatgttcca tcctgtacaa gtgctcagtt     420
ccaatgtgcc cagtcatgac atttctcaaa gtttttacag tgtatctcga agtcttccat    480
cagcagtgat tgaagtatct gtacctgccc ccactcagca tttcggtgct tcccttttcac  540 tgaagtgaat acatggtagc agggtctttg tgtgctgtgg attttgtggc ttcaatctac    600
gatgttaaaa caaattaaaa acacctaagt gactaccact tatttctaaa tcctcactat    660 tttttttgttg ctgttgttca gaagttgtta gtgatttgct atcatatatt ataagatttt  720
taggtgtctt ttaatgatac tgtctaagaa taatgacgta ttgtgaaatt tgttaatata   780
tataatactt aaaaatatgt gagcatgaaa ctatgcacct ataaatacta aatatgaaat    840 tttaccatt tgcgatgtgt tttattcact tgtgtttgta tataaatggt gagaattaaa    900
ataaaacgtt atctcattgc aaaaatattt tatttttatc ccatctcact ttaataataa   960
aaatcatgct tataagcaac atgaattaag aactgacaca aaggacaaaa atataaagtt    1020
attaatagcc atttgaagaa ggaggaattt tagaagaggt agagaaaatg gaacattaac   1080
cctacactcg gaattc                                                     1096
```

<210> SEQ ID NO 4
<211> LENGTH: 411
<212> TYPE: DNA
<213> ORGANISM: Homo sapiens

<400> SEQUENCE: 4

```
taaaggaatt cattagccat ggatgtattc atgaaaggac tttcaaaggc caaggaggga     60
gttgtggctg ctgctgagaa aaccaaacag ggtgtggcag aagcagcagg aaagacaaaa   120
gagggtgttc tctatgtagt ggctgagaag accaaagagc aagtgacaaa tgttggagga   180
gcagtggtga cggtgtgac agcagtagcc cagaagacag tggagggagc agggagcatt   240
gcagcagcca ctggctttgt caaaaaggac cagttgggca agaatgaaga aggagcccca   300
caggaaggaa ttctggaaga tatgcctgtg gatcctgaca atgaggctta tgaaatgcct   360
tctgaggaag ggtatcaaga ctacgaacct gaagcctaag aaatatcttt g             411
```

<210> SEQ ID NO 5
<211> LENGTH: 1208
<212> TYPE: DNA
<213> ORGANISM: Homo sapiens

<400> SEQUENCE: 5

-continued

| | |
|---|---|
| agagagggg cgagcgaccg agcgccgcga cgcggaagtg aggtgcgtgc gggctgcagc | 60 |
| gcagaccccg gcccggcccc tccgagagcg tcctgggcgc tccctcacgc cttgccttca | 120 |
| agccttctgc ctttccaccc tcgtgagcgg agaactggga gtggccattc gacgacaggt | 180 |
| tagcgggttt gcctcccact cccccagcct cgcgtcgccg gctcacagcg gcctcctctg | 240 |
| gggacagtcc cccccgggtg ccgcctccgc ccttcctgtg cgctccttt ccttcttctt | 300 |
| tcctattaaa tattatttgg gaattgttta aattttttt ttaaaaaaaa gagagaggcg | 360 |
| gggaggagtc ggagttgtgg agaagcagag ggactcagtg tggtgtaaag gaattcatta | 420 |
| gccatggatg tattcatgaa aggactttca aaggccaagg agggagttgt ggctgctgct | 480 |
| gagaaaacca aacagggtgt ggcagaagca gcaggaaaga caaagagggg tgttctctat | 540 |
| gtaggctcca aaaccaagga gggagtggtg catggtgtgg caacagtggc tgagaagacc | 600 |
| aaagagcaag tgacaaatgt tggaggagca gtggtgacgg gtgtgacagc agtagcccag | 660 |
| aagacagtgg agggagcagg gagcattgca gcagccactg gctttgtcaa aaaggaccag | 720 |
| ttgggcaaga atgaagaagg agccccacag gaaggaattc tggaagatat gcctgtggat | 780 |
| cctgacaatg aggcttatga aatgccttct gaggaagggt atcaagacta cgaacctgaa | 840 |
| gcctaagaaa tatctttgct cccagtttct tgagatctgc tgacagatgt tccatcctgt | 900 |
| acaagtgctc agttccaatg tgcccagtca tgacatttct caaagttttt acagtgtatc | 960 |
| tcgaagtctt ccatcagcag tgattgaagt atctgtacct gcccccactc agcatttcgg | 1020 |
| tgcttccctt tcactgaagt gaatacatgg tagcagggtc tttgtgtgct gtggatttg | 1080 |
| tggcttcaat ctacgatgtt aaaacaaatt aaaaacacct aagtgactac cacttatttc | 1140 |
| taaatcctca ctattttttg ttgctgttga aaaaaaaaa aaaaaaaaa aaaaaaaaa | 1200 |
| aaaaaaaa | 1208 |

<210> SEQ ID NO 6
<211> LENGTH: 708
<212> TYPE: DNA
<213> ORGANISM: Homo sapiens

<400> SEQUENCE: 6

| | |
|---|---|
| agcgggagaa ggagaaggag gaggactagg aggaggagga cggcgacgac cagaagggc | 60 |
| ccaagagagg gggcgagcga ccgagcgcgc gacgcggaag tgaggtgcgt gcgggctgca | 120 |
| gcgcagaccc cggcccggcc cctccgagag cgtcctgggc gctccctcac gccttgcctt | 180 |
| caagccttct gcctttccac cctcgtgagc ggagaactgg gagtggccat cgacgacag | 240 |
| tgtggtgtaa aggaattcat tagccatgga tgtattcatg aaaggacttt caaaggccaa | 300 |
| ggagggagtt gtggctgctg ctgagaaaac caaacagggt gtggcagaag cagcaggaaa | 360 |
| gacaaaagag ggtgttctct atgtaggctc caaaaccaag gagggagtgg tgcatggtgt | 420 |
| ggcaacagtg gctgagaaga ccaaagagca agtgacaaat gttggaggag cagtggtgac | 480 |
| gggtgtgaca gcagtagccc agaagacagt ggagggagca gggagcattg cagcagccac | 540 |
| tggctttgtc aaaaaggacc agttgggcaa gaatgacaga aggagccaca caggaaggac | 600 |
| attctggcag atatgcctgt ggatcctgac aatgaggctt atgacatgcc ttctgaggaa | 660 |
| gggtatcaag actacgaacc tgaagcctaa gacatatctt tgctccca | 708 |

<210> SEQ ID NO 7
<211> LENGTH: 516
<212> TYPE: DNA

<213> ORGANISM: Homo sapiens

<400> SEQUENCE: 7

```
ggaggacggc gacgaccaga aggggcccaa gagatggggc gagcgaccga gcgccgcgac     60
gcggaagtga gtgtggtgta aaggaattca ttagccatgg atgtattcat gaaaggactt    120
tcaaaggcca aggagggagt tgtggctgct gctgagaaaa ccaaacaggg tgtggcagaa    180
gcagcaggaa agacattttt tggtgttctc tatgtaggct ccaaaaccaa ggagggagtg    240
gtgcatggtg tggcaacagt ggctgagaag accaaagagc aagtgacaaa tgttggagga    300
gcagtggtga cgggtgtgac agcagtagcc cagaagacag tggagggagc agggagcatt    360
gcagcagcca ctggctttgt caaaaaggac cagttgggca agaatgaaga aggagcccca    420
caggaaggaa ttctggaaga tatgcctgtg gatcctgaca atgaggctta tgaaatgcct    480
tctgaggaag ggtatcaaga ctacgaacct gaagcc                             516
```

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8

```
acgaacctga agcctaagaa atatct                                          26
```

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9

```
gagcacttgt acaggatgga acat                                            24
```

<210> SEQ ID NO 10
<211> LENGTH: 29
<212> TYPE: DNA
<213> ORGANISM: Artificial Sequence
<220> FEATURE:
<223> OTHER INFORMATION: Probe

<400> SEQUENCE: 10

```
tgctcccagt ttcttgagat ctgctgaca                                       29
```

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11

```
aattcctttaa caccacactg                                                20
```

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
atggctaatg aattccttta                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
gaatacatcc atggctaatg                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
gtcctttcat gaatacatcc                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
tttgaaagtc ctttcatgaa                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
tccttggcct ttgaaagtcc                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
ctcagcagca gccacaactc                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
ttggttttct cagcagcagc                                              20

<210> SEQ ID NO 19
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 19
atagagaaca ccctcttttg                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
gttttggagc ctacatagag                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
tccttggttt tggagcctac                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
ttgccacacc atgcaccact                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
ccaacatttg tcacttgctc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
tgtcacaccc gtcaccactg                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
actggtcctt tttgacaaag                                              20
```

```
<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
cattcttgcc caactggtcc                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
gtcaggatcc acaggcatat                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28
ttcataagcc tcattgtcag                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
aaggcatttc ataagcctca                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
ttcctcagaa ggcatttcat                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
gatacccttc ctcagaaggc                                              20

<210> SEQ ID NO 32
<211> LENGTH: 20
<212> TYPE: DNA
<213> ORGANISM: Artificial Sequence
<220> FEATURE:
```

<223> OTHER INFORMATION: Synthetic Oligonucleotide

<400> SEQUENCE: 32
cgtagtcttg ataccettcc                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
tttcttaggc ttcaggttcg                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
agatatttct taggcttcag                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
ggagcaaaga tatttcttag                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
agcagatctc aagaaactgg                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
actgagcact tgtacaggat                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
ttggaactga gcacttgtac                                              20

```
<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
ggcacattgg aactgagcac                                                     20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
ttgagaaatg tcatgactgg                                                     20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
tgtaaaaact ttgagaaatg                                                     20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
gaagacttcg agatacactg                                                     20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
tcaatcactg ctgatggaag                                                     20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 44
tacagatact tcaatcactg                                                     20

<210> SEQ ID NO 45
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 45
gaccctgcta ccatgtattc                                                    20

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 46
agcacacaaa gaccctgcta                                                    20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
atccacagca cacaaagacc                                                    20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
gaagccacaa aatccacagc                                                    20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
ggtagtcact taggtgtttt                                                    20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 50
ataagtggta gtcacttagg                                                    20

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
ttagaaataa gtggtagtca                                                    20

<210> SEQ ID NO 52
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 52
aacttctgaa caacagcaac                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
cttataatat atgatagcaa                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 54
gtatcattaa aagacaccta                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 55
gtcattattc ttagacagta                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 56
tatttttgca atgagataac                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 57
aataaaatat ttttgcaatg                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 58
```

```
gcttataagc atgattttta                                      20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
aattcatgtt gcttataagc                                      20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 60
gtgtcagttc ttaattcatg                                      20

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 61
ggctattaat aactttatat                                      20

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 62
ttcttcaaat ggctattaat                                      20

<210> SEQ ID NO 63
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 63
ttctggcagt gttgcttcag                                      20

<210> SEQ ID NO 64
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 64
cagtgcatac caaaacacac                                      20

<210> SEQ ID NO 65
<211> LENGTH: 20
<212> TYPE: DNA
<213> ORGANISM: Artificial Sequence
```

-continued

```
<220> FEATURE:
<223> OTHER INFORMATION: Synthetic Oligonucleotide

<400> SEQUENCE: 65
cttaaggaac cagtgcatac                                         20

<210> SEQ ID NO 66
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 66
atcacagcca cttaaggaac                                         20

<210> SEQ ID NO 67
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 67
tcaataatta atcacagcca                                         20

<210> SEQ ID NO 68
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 68
ccactctaca atagtagttg                                         20

<210> SEQ ID NO 69
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 69
tatcagacaa aatagatttt                                         20

<210> SEQ ID NO 70
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 70
ttcacaccaa tatcagacaa                                         20

<210> SEQ ID NO 71
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 71
attgtcagaa aggtacagca                                         20
```

<210> SEQ ID NO 72
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 72
aatattattt attgtcagaa                                                    20

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
catggtcgaa tattatttat                                                    20

<210> SEQ ID NO 74
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 74
tcgcaaaatg gtaaaatttc                                                    20

<210> SEQ ID NO 75
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 75
gtctgcgctg cagcccgcac                                                    20

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 76
ggaggcaaac ccgctaacct                                                    20

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 77
gtttacctac ctacatagag                                                    20

<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 78
gttttggagc ctacaaaaac                                         20

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 79
ttctcagcca ctggtacaaa                                         20

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 80
ccattcccaa gagacccaga                                         20

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 81
agaagaatca attgctttac                                         20

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 82
taatcattta aaccttagta                                         20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83
gatacccttc ctaatattag                                         20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 84
gatacccttc cttgcccaac                                         20

<210> SEQ ID NO 85
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 85
gccactacat agagaacacc                                              20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 86
cctttacacc acactgagtc                                              20

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 87
atatctgcca gaatgtcctt                                              20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 88
ttacaccaca ctcacttccg                                              20

<210> SEQ ID NO 89
<211> LENGTH: 22
<212> TYPE: DNA
<213> ORGANISM: Artificial Sequence
<220> FEATURE:
<223> OTHER INFORMATION: Primer

<400> SEQUENCE: 89
ggtgcttccc tttcactgaa gt                                           22

<210> SEQ ID NO 90
<211> LENGTH: 24
<212> TYPE: DNA
<213> ORGANISM: Artificial Sequence
<220> FEATURE:
<223> OTHER INFORMATION: Primer

<400> SEQUENCE: 90
acatcgtaga ttgaagccac aaaa                                         24

<210> SEQ ID NO 91
<211> LENGTH: 32
<212> TYPE: DNA
<213> ORGANISM: Artificial Sequence
<220> FEATURE:
<223> OTHER INFORMATION: Probe

<400> SEQUENCE: 91
```

-continued

| | |
|---|---|
| aatacatggt agcagggtct ttgtgtgctg tg | 32 |

<210> SEQ ID NO 92
<211> LENGTH: 18
<212> TYPE: DNA
<213> ORGANISM: Artificial Sequence
<220> FEATURE:
<223> OTHER INFORMATION: Primer

<400> SEQUENCE: 92

| | |
|---|---|
| ggagcaggga gcattgca | 18 |

<210> SEQ ID NO 93
<211> LENGTH: 22
<212> TYPE: DNA
<213> ORGANISM: Artificial Sequence
<220> FEATURE:
<223> OTHER INFORMATION: Primer

<400> SEQUENCE: 93

| | |
|---|---|
| ccttcttcat tcttgcccaa ct | 22 |

<210> SEQ ID NO 94
<211> LENGTH: 17
<212> TYPE: DNA
<213> ORGANISM: Artificial Sequence
<220> FEATURE:
<223> OTHER INFORMATION: Probe

<400> SEQUENCE: 94

| | |
|---|---|
| cactggcttt gtcaaaa | 17 |

<210> SEQ ID NO 95
<211> LENGTH: 19
<212> TYPE: DNA
<213> ORGANISM: Artificial Sequence
<220> FEATURE:
<223> OTHER INFORMATION: Primer

<400> SEQUENCE: 95

| | |
|---|---|
| tggcagaagc agcaggaaa | 19 |

<210> SEQ ID NO 96
<211> LENGTH: 21
<212> TYPE: DNA
<213> ORGANISM: Artificial Sequence
<220> FEATURE:
<223> OTHER INFORMATION: Primer

<400> SEQUENCE: 96

| | |
|---|---|
| tccttggttt tggagcctac a | 21 |

<210> SEQ ID NO 97
<211> LENGTH: 17
<212> TYPE: DNA
<213> ORGANISM: Artificial Sequence
<220> FEATURE:
<223> OTHER INFORMATION: Probe

<400> SEQUENCE: 97

| | |
|---|---|
| caaaagaggg tgttctc | 17 |

<210> SEQ ID NO 98
<211> LENGTH: 20
<212> TYPE: DNA

<213> ORGANISM: Artificial Sequence
<220> FEATURE:
<223> OTHER INFORMATION: Synthetic Oligonucleotide

<400> SEQUENCE: 98
gttgccacac catgcaccac                                          20

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
tgttgccaca ccatgcacca                                          20

<210> SEQ ID NO 100
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 100
ctgttgccac accatgcacc                                          20

<210> SEQ ID NO 101
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 101
actgttgcca caccatgcac                                          20

<210> SEQ ID NO 102
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 102
cactgttgcc acaccatgca                                          20

<210> SEQ ID NO 103
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 103
ccactgttgc cacaccatgc                                          20

<210> SEQ ID NO 104
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 104
gccactgttg ccacaccatg                                          20

<210> SEQ ID NO 105
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 105
agccactgtt gccacaccat                                                   20

<210> SEQ ID NO 106
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 106
cagccactgt tgccacacca                                                   20

<210> SEQ ID NO 107
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 107
tcagccactg ttgccacacc                                                   20

<210> SEQ ID NO 108
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 108
ctcagccact gttgccacac                                                   20

<210> SEQ ID NO 109
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 109
tctcagccac tgttgccaca                                                   20

<210> SEQ ID NO 110
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 110
ttctcagcca ctgttgccac                                                   20

<210> SEQ ID NO 111
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 111
cttctcagcc actgttgcca                    20

<210> SEQ ID NO 112
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 112
tcttctcagc cactgttgcc                    20

<210> SEQ ID NO 113
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 113
gtcttctcag ccactgttgc                    20

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 114
ggtcttctca gccactgttg                    20

<210> SEQ ID NO 115
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 115
tggtcttctc agccactgtt                    20

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 116
ttggtcttct cagccactgt                    20

<210> SEQ ID NO 117
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 117
tttggtcttc tcagccactg                    20

-continued

```
<210> SEQ ID NO 118
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 118
ctttggtctt ctcagccact                                             20

<210> SEQ ID NO 119
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 119
tctttggtct tctcagccac                                             20

<210> SEQ ID NO 120
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 120
ctctttggtc ttctcagcca                                             20

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 121
gctctttggt cttctcagcc                                             20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 122
tgctctttgg tcttctcagc                                             20

<210> SEQ ID NO 123
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 123
ttgctctttg gtcttctcag                                             20

<210> SEQ ID NO 124
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 124
cttgctcttt ggtcttctca                                               20

<210> SEQ ID NO 125
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 125
acttgctctt tggtcttctc                                               20

<210> SEQ ID NO 126
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 126
cacttgctct ttggtcttct                                               20

<210> SEQ ID NO 127
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 127
tcacttgctc tttggtcttc                                               20

<210> SEQ ID NO 128
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 128
gtcacttgct ctttggtctt                                               20

<210> SEQ ID NO 129
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 129
tgtcacttgc tctttggtct                                               20

<210> SEQ ID NO 130
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 130
ttgtcacttg ctctttggtc                                               20

<210> SEQ ID NO 131
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 131
tttgtcactt gctctttggt                                                 20

<210> SEQ ID NO 132
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 132
atttgtcact tgctctttgg                                                 20

<210> SEQ ID NO 133
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 133
catttgtcac ttgctctttg                                                 20

<210> SEQ ID NO 134
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 134
acatttgtca cttgctcttt                                                 20

<210> SEQ ID NO 135
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 135
aacatttgtc acttgctctt                                                 20

<210> SEQ ID NO 136
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 136
caacatttgt cacttgctct                                                 20

<210> SEQ ID NO 137
<211> LENGTH: 1296
<212> TYPE: DNA
<213> ORGANISM: Mus musculus

<400> SEQUENCE: 137
acagccctca cgcaccgcac ctccaaccaa cccgtcccct ccctaggaag aggagcgaag     60
```

-continued

```
gcacgaggca ggcgagggc ggggagaggc gctgacaaat cagctgcggg ggcgacgtga    120
aggagccagg gagccagagc gcccggcagc aggcagcaga cggcaggaga ccagcaggtg    180 ttcccctgc ccctgcctgc ccttgcctct ttcattgaaa ttagattggg gaaaacagga    240
agaatcggag ttcttcagaa gcctaggag ccgtgtggag caaaaataca tctttagcca    300
tggatgtgtt catgaaagga cttcaaagg ccaaggaggg agttgtggct gctgctgaga    360
aaaccaagca gggtgtggca gaggcagctg gaaagacaaa agagggagtc ctctatgtag    420
gttccaaaac taaggaagga gtggttcatg gagtgacaac agtggctgag aagaccaaag    480
agcaagtgac aaatgttgga ggagcagtgg tgactggtgt gacagcagtc gctcagaaga    540
cagtggaggg agctgggaat atagctgctg ccactggctt tgtcaagaag gaccagatgg    600
gcaagggtga ggagggtac ccacaggaag gaatcctgga agacatgcct gtggatcctg    660
gcagtgaggc ttatgaaatg ccttcagagg aaggctacca agactatgag cctgaagcct    720
aagaatgtca ttgcacccaa tctcctaaga tctgccggct gctcttccat ggcgtacaag    780
tgctcagttc caatgtgccc agtcatgacc ttttctcaaa gctgtacagt gtgtttcaaa    840
gtcttccatc agcagtgatc ggcgtcctgt acctgcccct cagcatcccg gtgctcccct    900
ctcactacag tgaaaacctg gtagcagggt cttgtgtgct gtggatattg ttgtggcttc    960
acacttaaat tgttagaaga aacttaaaac acctaagtga ctaccactta tttctaaatc   1020
ttcatcgttt tctttttgtt gctgttctta agaagttgtg atttgctcca agagttttag   1080
gtgtcctgaa tgactctttc tgtctaagaa tgatgtgttg tgaaatttgt taatatatat   1140
tttaaaatta tgtgagcatg agactatgca cctataaata ttaatttatg aattttacag   1200
ttttgtgatg tgttttatta acttgtgttt gtatataaat ggtggaaaat aaaataaaat   1260
attatccatt gcaaaatcaa aaaaaaaaaa aaaaaa                             1296
```

<210> SEQ ID NO 138
<211> LENGTH: 24
<212> TYPE: DNA
<213> ORGANISM: Artificial Sequence
<220> FEATURE:
<223> OTHER INFORMATION: Primer

<400> SEQUENCE: 138

```
agaccaaaga gcaagtgaca aatg                                            24
```

<210> SEQ ID NO 139
<211> LENGTH: 23
<212> TYPE: DNA
<213> ORGANISM: Artificial Sequence
<220> FEATURE:
<223> OTHER INFORMATION: Primer

<400> SEQUENCE: 139

```
cctccactgt cttctgggct act                                             23
```

<210> SEQ ID NO 140
<211> LENGTH: 23
<212> TYPE: DNA
<213> ORGANISM: Artificial Sequence
<220> FEATURE:
<223> OTHER INFORMATION: Probe

<400> SEQUENCE: 140

```
tggaggagca gtggtgacgg gtg                                             23
```

```
<210> SEQ ID NO 141
<211> LENGTH: 23
<212> TYPE: DNA
<213> ORGANISM: Artificial Sequence
<220> FEATURE:
<223> OTHER INFORMATION: Primer

<400> SEQUENCE: 141
gtcattgcac ccaatctcct aag                                               23

<210> SEQ ID NO 142
<211> LENGTH: 21
<212> TYPE: DNA
<213> ORGANISM: Artificial Sequence
<220> FEATURE:
<223> OTHER INFORMATION: Primer

<400> SEQUENCE: 142
gactgggcac attggaactg a                                                 21

<210> SEQ ID NO 143
<211> LENGTH: 24
<212> TYPE: DNA
<213> ORGANISM: Artificial Sequence
<220> FEATURE:
<223> OTHER INFORMATION: Probe

<400> SEQUENCE: 143
cggctgctct tccatggcgt acaa                                              24
```

MODULATION OF ALPHA SYNUCLEIN EXPRESSION

SEQUENCE LISTING

The present application is being filed along with a Sequence Listing in electronic format. The Sequence Listing is provided as a file entitled BIOL0139USC2SEQ_ST25.txt created Sep. 17, 2020, which is 184 Kb in size. The information in the electronic format of the sequence listing is incorporated herein by reference in its entirety.

FIELD OF THE INVENTION

Embodiments of the present invention provide methods, compounds, and compositions for inhibiting expression of alpha-synuclein mRNA and protein in an animal. Such methods, compounds, and compositions are useful to treat, prevent, or ameliorate neurodegenerative diseases, including, Parkinson's disease, dementia, multiple system atrophy, and Alzheimer's disease.

BACKGROUND OF THE INVENTION

Alpha-synuclein (also known as α-synuclein, SNCA, and α-SYN) is a small, highly charged 140-amino acid residue protein, predominantly expressed in central nervous system (CNS) neurons, where it is localized at presynaptic terminals in close proximity to synaptic vesicles (Iwai, et al., *Neuron*. 1995. 14: 467-475). Alpha-synuclein can associate with lipid membranes by forming amphipathic α-helices, as shown in vitro (Davidson, et al., *J. Biol. Chem*. 1998. 273: 9443-9449). Although the function of alpha-synuclein is still poorly understood, several studies suggest that it is involved in modulating synaptic transmission, the density of synaptic vesicles, and neuronal plasticity (Cabin et al., *J. Neurosci*. 2002. 22: 8797-8807). It has also been suggested that alpha-synuclein may have a chaperone function, as indicated by its effectiveness in preventing aggregation of proteins in in vitro assays (Souza et al., *FEBS Lett*. 2000. 474: 116-119). Moreover, in vivo assays demonstrate that alpha-synuclein chaperone activity is instrumental in promoting the assembly of the SNARE-complex, which is essential for neurotransmitter release in the presynaptic terminals of the brain (Burre et al., *Science*. 329: 1663-1667). Decreased SNARE-complex assembly is associated with neurological impairment, thus, indicating a link between presynaptic alpha-synuclein aggregates and neurodegeneration (Kramer and Schulz-Schaeffer, *J. Neurosci*. 2007. 27: 1405-1410). Knockout mouse models of alpha-synuclein are not lethal, and brain morphology is intact, suggesting that alpha-synuclein is not required for neuronal development and/or that compensatory pathways are present (Abeliovich et al., *Neuron*. 2000. 25: 239-252).

Misfolding, aggregation, and fibrillation of alpha-synuclein are implicated as critical factors in several neurodegenerative diseases, including, Parkinson's disease, Lewy body variant of Alzheimer's disease, diffuse Lewy body disease, dementia with Lewy bodies, and multiple system atrophy (Schulz-Schaeffer *Acta Neuropathol*. 2010. 120: 131-143; Yoshida. *Neuropathology*. 2007. 27: 484-493). In each of these cases, alpha-synuclein protein is misfolded and assembles in aggregates in Lewy bodies and Lewy neurites (Uversky. *J. Neurochem*. 2007. 103: 17-37). Several recent studies have shown that lipidic environments that promote alpha-synuclein folding also accelerate alpha-synuclein aggregation, suggesting that the lipid-associated conformation of alpha-synuclein may be relevant to alpha-synuclein misfolding in neurodegenerative diseases (Conway et al., *Science*. 2001. 294: 6-9; Lee et al., *J. Biol. Chem*. 2002. 277: 671-678). Mutations at position 53, where alanine is changed to threonine, and at position 30, where alanine is changed to proline, have been shown to cause alpha-synuclein to be in a random coil state, so that aggregation is more likely to occur (Clayton and George, *J. Neurosci*. 1999. 58: 120-129).

There is a currently a lack of acceptable options for treating such neurodegenerative disorders. It is therefore an object herein to provide compounds and methods for the treatment of such diseases and disorder.

SUMMARY OF THE INVENTION

Provided herein are methods, compounds, and compositions for modulating expression of alpha-synuclein mRNA and protein. In certain embodiments, alpha-synuclein specific inhibitors modulate expression of alpha-synuclein mRNA and protein. In certain embodiments, alpha-synuclein specific inhibitors are nucleic acids, proteins, antibodies, or small molecules.

In certain embodiments, modulation can occur in a cell or tissue. In certain embodiments, the cell or tissue is in an animal. In certain embodiments, the animal is a human. In certain embodiments, alpha-synuclein mRNA levels are reduced. In certain embodiments, alpha-synuclein protein levels are reduced. In certain embodiments, alpha-synuclein mRNA and protein levels are reduced. Such reduction can occur in a time-dependent manner or in a dose-dependent manner.

Also provided are methods, compounds, and compositions useful for preventing, treating, and ameliorating diseases, disorders, and conditions. In certain embodiments, such diseases, disorders, and conditions are neurodegenerative diseases, disorders, and conditions. In certain embodiments, such neurodegenerative diseases, disorders, and conditions include Parkinson's Disease, dementia, multiple system atrophy (also Shy-Drager syndrome), sporadic and familial Alzheimer's Disease, Lewy body variant of Alzheimer's disease, diffuse Lewy body disease, dementia with Lewy bodies, and pure autonomic failure (also known as Bradbury-Eggleston syndrome). In certain embodiments, such diseases, disorders, and conditions are termed synucleinopathies. In certain embodiments, such synucleinopathies include Parkinson's disease, dementia with Lewy bodies, multiple system atrophy, and pure autonomic failure.

Such diseases, disorders, and conditions can have one or more risk factors, causes, or outcomes in common. Certain risk factors and causes for development of a neurodegenerative disease, and, in particular, a synucleinopathy, include older age, exposure to neurotoxins, genetic predisposition, and trauma.

In certain embodiments, methods of treatment include administering an alpha-synuclein specific inhibitor to an individual in need thereof.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical agent" means the substance or substances in a pharmaceutical composition that provide a therapeutic benefit when administered to an individual. For example, in certain embodiments an antisense oligonucleotide targeted to an alpha-synuclein nucleic acid is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to, administering by a medical professional and self-administering.

"Alpha-synuclein nucleic acid" or "α-synuclein" or "SNCA" or "a-SYN" means any nucleic acid encoding alpha-synuclein. For example, in certain embodiments, an alpha-synuclein nucleic acid includes a DNA sequence encoding alpha-synuclein, an RNA sequence transcribed from DNA encoding alpha-synuclein (including genomic DNA comprising introns and exons), and an mRNA sequence encoding alpha-synuclein. "alpha-synuclein mRNA" means an mRNA encoding an alpha-synuclein protein.

"Alpha-synuclein specific inhibitor" refers to any agent capable of inhibiting the expression of alpha-synuclein mRNA and/or alpha-synuclein protein with few to no off-target effects. Alpha-synuclein specific inhibitors include, but are not limited to, nucleic acids (including antisense compounds), peptides, antibodies, small molecules, and other agents capable of inhibiting the expression of alpha-synuclein mRNA and/or alpha-synuclein protein. In certain embodiments, by specifically modulating alpha-synuclein mRNA expression and/or alpha-synuclein protein expression, alpha-synuclein specific inhibitors affect other downstream proteins and molecules.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is is capable of undergoing hybridization to a target nucleic acid through hydrogen bonding.

"Antisense inhibition" means reduction of target nucleic acid levels or target protein levels in the presence of an antisense compound complementary to a target nucleic acid as compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two atoms. A bicyclic sugar is a modified sugar.

"Bicyclic nucleoside" means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Identifying an animal at risk for neurodegenerative disease" means identifying an animal having been diagnosed with a neurodegenerative disease or identifying an animal predisposed to develop a neurodegenerative disease. Such identification may be accomplished by any method including evaluating an individual's medical history and standard clinical tests or assessments.

"Immediately adjacent" means there are no intervening elements between the immediately adjacent elements.

"Inhibiting alpha-synuclein" means reducing expression of alpha-synuclein mRNA and/or protein levels in the presence of an alpha-synuclein specific inhibitor as compared to expression of alpha-synuclein mRNA and/or protein levels in the absence of an alpha-synuclein specific inhibitor.

"Individual" means a human or non-human animal selected for treatment or therapy.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Neurodegenerative disease" means a disease characterized by progressive loss of structure or function of neurons, including death of neurons.

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," "target mRNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Embodiments of the present invention provide methods, compounds, and compositions for inhibiting alpha-synuclein mRNA and protein expression.

Embodiments of the present invention provide methods for the treatment, prevention, or amelioration of diseases, disorders, and conditions associated with alpha-synuclein in an individual in need thereof. Also contemplated are methods for the preparation of a medicament for the treatment, prevention, or amelioration of a disease, disorder, or condition associated with alpha-synuclein. Alpha-synuclein associated diseases, disorders, and conditions include neurodegenerative diseases and synucleinopathies, which include Parkinson's Disease, dementia, multiple system atrophy (also Shy-Drager syndrome), sporadic and familial Alzheimer's Disease, Lewy body variant of Alzheimer's disease, diffuse Lewy body disease, and dementia with Lewy bodies.

Embodiments of the present invention provide for the use of an alpha-synuclein specific inhibitor for treating, preventing, or ameliorating an alpha-synuclein associated disease. In certain embodiments, alpha-synuclein specific inhibitors are nucleic acids (including antisense compounds), peptides, antibodies, small molecules, and other agents capable of inhibiting the expression of alpha-synuclein mRNA and/or alpha-synuclein protein.

In certain embodiments of the present invention, alpha-synuclein specific inhibitors are peptides or proteins, such as, but not limited to, synthetic construct alpha-synuclein (68-78), N-methylated at Gly73 as described in *Neurosci. Lett.* 2004. 359: 89-93; N-methylated derivative of SNCA (25-35) as described in *J. Biol. Chem.* 2000. 275: 25109-25112; ASI peptides as described in *FASEB J.* 2004.18: 1315-1317; RGAVVTGR-amide and RGGAVVT-GRRRRRR-amide as described in *Biochem. Soc. Trans.* 2005. 33: 1106-1110; FK506 as described in *J. Neurosci.* 2010. 30: 2454-2463; tissue transglutaminase as described in *Protein Sci.* 2008. 17: 1395-1402; beta-synuclein as described in *J. Biol. Chem.* 2005. 280: 7562-7569; and peptidyl compounds which are retroenantiomers of the alpha-synuclein sequence as described in US 2009/0286745.

In certain embodiments of the present invention, alpha-synuclein specific inhibitors are antibodies, such as, but not limited to, human single-chain Fv (scFv) antibody, D10, as described in *Mol. Ther.* 2004. 10: 1023-1031; human alpha-SNCA antibodies as described in U.S. Pat. No. 7,727,957; anti-synuclein antibodies as described in U.S. Pat. No. 6,890,535; humanized or chimeric 9E4 antibody as described in USPPN 2010/0278814; humanized version of mouse monoclonal antibody 6H7 as described in USPPN 2010/0031377; and humanized anti-synuclein monoclonal antibody as described in USPPN 2008/0300204.

In certain embodiments of the present invention, alpha-synuclein specific inhibitors are small molecules, such as, but not limited to, curcumin, nicotine, and wine-related polyphenols as described in *Curr. Pharm. Des.* 2008. 14: 3247-3266; 4% $H_2O_2$ as described in *Biochim. Biophys. Acta* 2005. 1703: 157-169; selegiline as described in *J. Mol. Biol.* 2010. Nov. 1. Epub ahead of print; baicalein as described in *J. Neurochem.* 2010. 114: 419-429; cyclic tetrapyrrole phthalocyanine tetrasulfonate as described in *Proc. Natl. Acad. Sci USA.* 2009. 106: 1057-62; SNX-0723 as described in *J. Pharmacol. Exp. Ther.* 2010. 332: 849-857; N'-benzylidene-benzohydrazide compounds as described in *Biochem. Biophys. Res. Commun.* 2010. 391: 461-466; MG132 and epoxomicin as described in *Neurotox. Res.* 2010. 17: 215-227; congo red and Lacmoid as described in *Biochemistry.* 2009. 48: 8322-8334; flavonoid quinine as described in *Biochemistry.* 2009. 48: 8206-8224; valproic acid as described in *Neurotox. Res.* 2010. 17: 130-141; 3,4-dihydroxyphenylacetic acid (DOPAC) as described in *J. Mol. Biol.* 2009. 388: 597-610; PAMAM dendrimers as described in *Macromol. Biosci.* 2009. 9: 230-238; dopamine as described in *PLoS One.* 2008. 3: e3394; melatonin as described in *J. Pineal Res.* 2007. 42: 125-130; rifampicin as described in *Brain Res.* 2007. 1139: 220-225 and *Chem. Biol.* 2004. 11: 1513-1521; ganglioside GM1 as described in *Biochemistry.* 2007. 46: 4868-1877; 4-hydroxy-2-nonenal as described in *J. Biol. Chem.* 2007. 282: 5862-5870; trehalose as described in *J. Biol. Chem.* 2007. 282: 5641-5652; 1,2-dipalmitoyl-sn-glycero-3-phosphate/1,2-dipalmitoyl-sn-glycero-3-phosphocholine and 1,2-dipalmitoyl-sn-glycero-3-phospho-RAC-(1-glycerol)/1,2-dipalmitoyl-sn-glycero-3-phosphocholine as described in *J. Biol. Chem.* 2003. 278: 16873-16877; bis- and tris-dihydroxyaryl compounds and their methylenedioxy analogs as described in USPPN 2010/0179223 and U.S. Pat. No. 7,763,747; 5-(fluoromethyl)piperidine-3,4-diol, 5-(chloromethyl)piperidine-3,4-diol as described in USPPN 2010/0261753; ramelteon as described in USPPN 2010/0056622; cleavage agents as described in USPPN 2010/0036122; *Uncaria tomentosa* extract, *gingko biloba*, green tea extract, grape seed extract and curcumin as described in USPPN 2009/0123575; catechin or green tea extract as described in USPPN 2008/0306143; farnesyl transferase inhibitor as described in USPPN 2007/0213366.

Embodiments of the present invention provide antisense compounds targeted to an alpha-synuclein nucleic acid. In certain embodiments, the alpha-synuclein nucleic acid is any of the sequences set forth in GENBANK Accession No. NM_000345.3, incorporated herein as SEQ ID NO: 1; the complement of GENBANK Accession No. NT_016354.17 truncated from nucleotides 15140000 to Ser. No. 15/255, 000, incorporated herein as SEQ ID NO: 2; GENBANK Accession No. NM_007308.1, incorporated herein as SEQ ID NO: 3; GENBANK Accession No. L36674.1, incorporated herein as SEQ ID NO: 4; GENBANK Accession No. BC013293.2, incorporated herein as SEQ ID NO: 5; GENBANK Accession No. BG701026.1, incorporated herein as SEQ ID NO: 6; or GENBANK Accession No. BM069769.1, incorporated herein as SEQ ID NO: 7.

In certain embodiments, the invention provides a compound comprising a modified oligonucleotide. In certain embodiments, the compound of the invention comprises a modified oligonucleotide consisting of 12 to 30 linked nucleosides.

In certain embodiments, the compound of the invention may comprise a modified oligonucleotide comprising a nucleobase sequence at least 80%, at least 85%, at least 90%, at least 95%, at least 96%, at least 97%, at least 98%, at least 99% complementary to an equal length portion of SEQ ID NO: 1, 2, 3, 4, 5, 6, or 7. In certain embodiments, the compound of the invention may comprise a modified oligonucleotide comprising a nucleobase sequence 100% complementary to an equal length portion of SEQ ID NO: 1, 2, 3, 4, 5, 6, or 7.

In certain embodiments, the invention provides a compound comprising a modified oligonucleotide comprising a nucleobase sequence complementary to at least a portion of nucleobases 404 to 463 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 404 to 463 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 40% inhibition of human mRNA levels as determined using an RT-PCR assay method, optionally in SH-SY5Y cells (e.g., as described in Example 6).

In certain embodiments, the invention provides a compound comprising a modified oligonucleotide comprising a nucleobase sequence complementary to at least a portion of nucleobases 107 to 126 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 107 to 126 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 70% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 236 to 301 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 236 to 301 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 70% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 304 to 331 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 304 to 331 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 70% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 361 to 400 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 361 to 400 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 70% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 404 to 423 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 404 to 423 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 90% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 444 to 463 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 444 to 463 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 90% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 469 to 488 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 469 to 488 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 90% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 542 to 573 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 542 to 573 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 60% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 607 to 721 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 607 to 721 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 30% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 734 to 837 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 734 to 837 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 30% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 881 to 927 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 881 to 927 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 60% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 952 to 983 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 952 to 983 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 40% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 1001 to 1020 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1001 to 1020 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 80% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 1030 to 1049 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1030 to 1049 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 30% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 1055 to 1091 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1055 to 1091 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 80% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 1242 to 1261 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1242 to 1261 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 20% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 1292 to 1333 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1292 to 1333 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 20% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 1345 to 1374 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1345 to 1374 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 20% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 1432 to 1501 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1432 to 1501 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 30% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 1522 to 1541 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1522 to 1541 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 40% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nucleobases 1703 to 1742 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1703 to 1742 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 60% inhibition of human mRNA levels as determined using an RT-PCR assay method, optionally in HuVEC cells (e.g., as described in Example 1).

Embodiments of the present invention provide, a modified oligonucleotide consisting of 12 to 30 linked nucleosides having a nucleobase sequence comprising at least 12 contiguous nucleobases of a nucleobase sequence selected from among the nucleobase sequences recited in SEQ ID NOs: 11 to 88 and 98 to 136.

In certain embodiments, the modified oligonucleotide is a single-stranded oligonucleotide.

In certain embodiments, the modified oligonucleotide has a nucleobase sequence that is 100% complementary to a human alpha-synuclein nucleic acid.

In certain embodiments, the modified oligonucleotide comprises at least one modified internucleoside linkage.

In certain embodiments, the at least one modified internucleoside linkage is a phosphorothioate internucleoside linkage.

In certain embodiments, the at least one nucleoside of the modified oligonucleotide comprises a modified sugar.

In certain embodiments, the modified sugar is a bicyclic sugar.

In certain embodiments, the bicyclic sugar comprises a 4'-CH(CH$_3$)—O-2' bridge.

In certain embodiments, the at least one tetrahydropyran modified nucleoside wherein a tetrahydropyran ring replaces the furanose ring.

In certain embodiments, each of the at least one tetrahydropyran modified nucleoside has the structure:

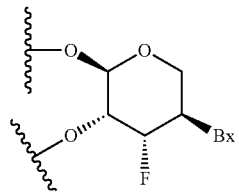

wherein Bx is an optionally protected heterocyclic base moiety.

In certain embodiments, the modified sugar comprises a 2'-O-methoxyethyl group.

In certain embodiments, the at least one nucleoside of the modified oligonucleotide comprises a modified nucleobase.

In certain embodiments, the modified nucleobase is a 5-methylcytosine.

In certain embodiments, the modified oligonucleotide comprises:
(i) a gap segment consisting of linked deoxy nucleosides;
(ii) a 5' wing segment consisting of linked nucleosides;
(iii) a 3' wing segment consisting of linked nucleosides; wherein the gap segment is positioned between the 5' wing segment and the 3' wing segment and wherein each nucleoside of each wing segment comprises a modified sugar.

In certain embodiments, the modified oligonucleotide comprises:
(i) a gap segment consisting of ten linked deoxynucleosides;
(ii) a 5' wing segment consisting of five linked nucleosides;
(iii) a 3' wing segment consisting of five linked nucleosides; wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage; and wherein each cytosine is a 5-methylcytosine.

Embodiments of the present invention provide methods for identifying an animal having a neurodegenerative disease and administering to said animal a therapeutically effective amount of a composition comprising a modified oligonucleotide consisting of 12 to 30 linked nucleosides having a nucleobase sequence comprising at least 12 contiguous nucleobases of a nucleobase sequence selected from among the nucleobases sequences recited in SEQ ID NOs: SEQ ID NOs: 11 to 88 and 98 to 136.

In certain embodiments, the administration reduces expression of alpha-synuclein.

In certain embodiments, the administration improves motor coordination.

In certain embodiments, the administration improves olfaction.

In certain embodiments, the administration improves spatial memory.

In certain embodiments, the administration reduces aggregation of alpha-synuclein.

Embodiments of the present invention provide, a modified oligonucleotide consisting of 12 to 30 linked nucleosides and having a nucleobase sequence comprising a portion of at least 8, 9, 10, 11, 12, 13, 14, 15, 16, 17, 18, 19, or 20 contiguous nucleobases complementary to an equal length portion of nucleobases 404 to 463 of SEQ ID NO: 1; and wherein the nucleobase sequence of the modified oligonucleotide is at least 90%, 91%, 92%, 93%, 94%, 95%, 96%, 97%, 98%, 99%, or 100% complementary to SEQ ID NO: 1.

Embodiments of the present invention provide, the use of any antisense oligonucleotide described herein for reducing expression of alpha-synuclein in an animal.

Embodiments of the present invention provide, the use of any antisense oligonucleotide described herein for improving motor coordination in an animal.

Embodiments of the present invention provide, the use of any antisense oligonucleotide described herein for reducing aggregation of alpha-synuclein in an animal.

Embodiments of the present invention provide, the use of any antisense oligonucleotide described herein for use in treating an animal having a disease or condition associated with alpha-synuclein by administering to the animal a therapeutically effective amount of the compound so that expression of alpha-synuclein is inhibited.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an alpha-synuclein nucleic acid is 12 to 30 subunits in length. In other words, such antisense compounds are from 12 to 30 linked subunits. In other embodiments, the antisense compound is 8 to 80, 12 to 50, 15 to 30, 18 to 24, 19 to 22, or 20 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments antisense oligonucleotides targeted to an alpha-synuclein nucleic acid may be shortened or truncated. For example, a single subunit may be deleted from the 5' end (5' truncation), or alternatively from the 3' end (3' truncation). A shortened or truncated antisense compound targeted to an alpha-synuclein nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (*Proc. Natl. Acad. Sci. USA* 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (*J. Natl. Cancer Inst.* 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (*Nuc. Acid. Res.* 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an alpha-synuclein nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers of the present invention include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 5-8-5, or 6-8-6.

In certain embodiments, the antisense compound has a "wingmer" motif, having a wing-gap or gap-wing configuration, i.e. an X-Y or Y-Z configuration as described above for the gapmer configuration. Thus, wingmer configurations of the present invention include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to an alpha-synuclein nucleic acid possess a 5-10-5 gapmer motif.

In certain embodiments, an antisense compound targeted to an alpha-synuclein nucleic acid has a gap-widened motif.

Target Nucleic Acids, Target Regions and Nucleotide Sequences

Nucleotide sequences that encode alpha-synuclein include, without limitation, the following: GENBANK Accession No. NM_000345.3, incorporated herein as SEQ ID NO: 1; the complement of GENBANK Accession No. NT_016354.17 truncated from nucleotides 15140000 to Ser. No. 15/255,000, incorporated herein as SEQ ID NO: 2;

GENBANK Accession No. NM_007308.1, incorporated herein as SEQ ID NO: 3; GENBANK Accession No. L36674.1, incorporated herein as SEQ ID NO: 4; GENBANK Accession No. BC013293.2, incorporated herein as SEQ ID NO: 5; GENBANK Accession No. BG701026.1, incorporated herein as SEQ ID NO: 6; or GENBANK Accession No. BM069769.1, incorporated herein as SEQ ID NO: 7.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for alpha-synuclein can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in alpha-synuclein mRNA levels are indicative of inhibition of alpha-synuclein expression. Reductions in levels of an alpha-synuclein protein are also indicative of inhibition of target mRNA expression. Further, phenotypic changes are indicative of inhibition of alpha-synuclein expression. For example, improved motor coordination, reduced incidence of resting tremor, reduced incidence of bradykinesia (slow movement), reduced rigidity or inflexibility, improved balance, improved fine motor dexterity, improved gross motor coordination, reduced aggregation of alpha-synuclein, recovery from loss in olfaction, and improved autonomic function, such as, decreased orthostatic hypotension.

Hybridization

In some embodiments, hybridization occurs between an antisense compound disclosed herein and an alpha-synuclein nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with an alpha-synuclein nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an alpha-synuclein nucleic acid).

Non-complementary nucleobases between an antisense compound and an alpha-synuclein nucleic acid may be tolerated provided that the antisense compound remains able to specifically hybridize to a target nucleic acid. Moreover, an antisense compound may hybridize over one or more segments of an alpha-synuclein nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an alpha-synuclein nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, *Genome Res.*, 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to an alpha-synuclein nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an alpha-synuclein nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an alpha-synuclein nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an alpha-synuclein nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise a chemically modified ribofuranose ring moiety. Examples of chemically modified ribofuranose rings include, without limitation, addition of substituent groups (including 5' and 2' substituent groups); bridging of non-geminal ring atoms to form bicyclic nucleic acids (BNA); replacement of the ribosyl ring oxygen atom with S, N(R), or C(R1)(R)2 (R=H, $C_1$-$C_{12}$ alkyl or a protecting group); and combinations thereof. Examples of chemically modified sugars include, 2'-F-5'-methyl substituted nucleoside (see, PCT International Application WO 2008/101157, published on Aug. 21, 2008 for other disclosed 5', 2'-bis substituted nucleosides), replacement of the ribosyl ring oxygen atom with S with further substitution at the 2'-position (see, published U.S. Patent Application US2005/0130923, published on Jun. 16, 2005), or, alternatively, 5'-substitution of a BNA (see, PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-OCH$_3$, and 2'-O(CH$_2$)$_2$OCH$_3$ substituent groups. The substituent at the 2' position can also be selected from allyl, amino, azido, thio, O-allyl, O—$C_1$-$C_{10}$ alkyl, OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In certain embodiments, antisense compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-(CH$_2$)—O-2' (LNA); 4'-(CH$_2$)$_2$—S-2'; 4'-(CH$_2$)$_2$—O-2' (ENA); 4'-CH(CH$_3$)—O-2' and 4'-CH(CH$_2$OCH$_3$)—O-2', and analogs thereof (see, U.S. Pat. No. 7,399,845, issued on Jul. 15, 2008); 4'-C(CH$_3$)(CH$_3$)—O-2', and analogs thereof (see, published PCT International Application WO2009/006478, published Jan. 8, 2009); 4'-CH$_2$—N(OCH$_3$)-2', and analogs thereof (see, published PCT International Application WO2008/150729, published Dec. 11, 2008); 4'-CH$_2$—O—N(CH$_3$)-2' (see, published U.S. Patent Application US2004/0171570, published Sep. 2, 2004); 4'-CH$_2$—N(R)—O-2', wherein R is H, $C_1$-$C_{12}$ alkyl, or a protecting group (see, U.S. Pat. No. 7,427,672, issued on Sep. 23, 2008); 4'-CH$_2$—C(H)(CH$_3$)-2' (see, Chattopadhyaya, et al., *J. Org. Chem.*, 2009, 74, 118-134); and 4'-CH$_2$—C(=CH$_2$)-2', and analogs thereof (see, published PCT International Application WO 2008/154401, published on Dec. 8, 2008). Also see, for example: Singh et al., *Chem. Commun.*, 1998, 4, 455-456; Koshkin et al., *Tetrahedron*, 1998, 54, 3607-3630; Wahlestedt et al., *Proc. Nat. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 6,670,461, 7,053,207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent Ser. Nos. 12/129,154, 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)

=C($R_b$)—, —C($R_a$)=N—, —C(=N$R_a$)—, —C(=O)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, O$J_1$, N$J_1J_2$, S$J_1$, $N_3$, COO$J_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

In certain embodiments, the bridge of a bicyclic sugar moiety is, —[C($R_a$)($R_b$)]$_n$—, —[C($R_a$)($R_b$)]$_n$—O—, —C($R_aR_b$)—N(R)—O— or, —C($R_aR_b$)—O—N(R)—. In certain embodiments, the bridge is 4'-CH$_2$-2', 4'-(CH$_2$)$_2$-2', 4'-(CH$_2$)$_3$-2', 4'—CH$_2$—O-2', 4'-(CH$_2$)$_2$—O-2', 4'—CH$_2$—O—N(R)-2', and 4'-CH$_2$—N(R)—O-2'-, wherein each R is, independently, H, a protecting group, or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-Methyleneoxy (4'-CH$_2$—O-2') BNA, (B) β-D-Methyleneoxy (4'-CH$_2$—O-2') BNA, (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

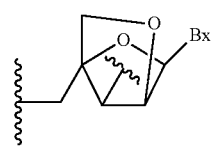

(A)

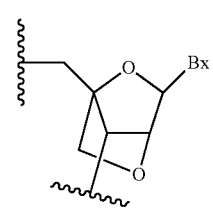

(B)

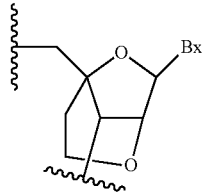

(C)

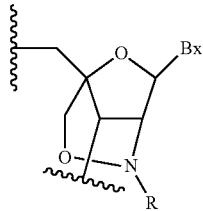

(D)

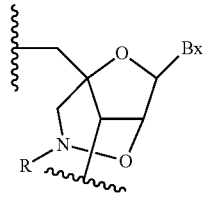

(E)

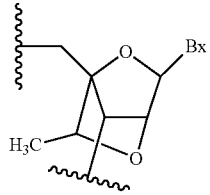

(F)

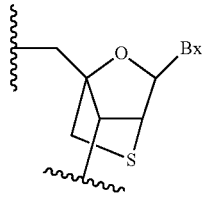

(G)

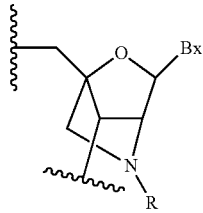

(H)

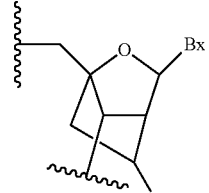

(I)

-continued

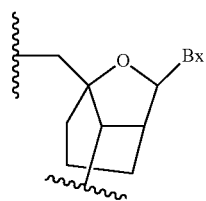

(J)

wherein Bx is the base moiety and R is, independently, H, a protecting group or $C_1$-$C_{12}$ alkyl.

In certain embodiments, bicyclic nucleoside having Formula I

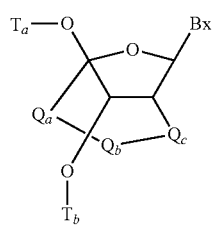

I wherein:
Bx is a heterocyclic base moiety;
-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O—, or —N($R_c$)—O—$CH_2$;
$R_c$ is $C_1$-$C_{12}$ alkyl or an amino protecting group; and
$T_a$ and $T_b$ are each, independently, H, a hydroxyl protecting group, a conjugate group, a reactive phosphorus group, a phosphorus moiety, or a covalent attachment to a support medium.

In certain embodiments, bicyclic nucleoside having Formula II:

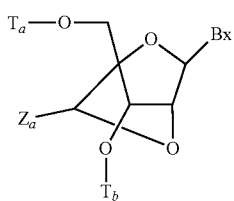

II wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC(=X)NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In certain embodiments, bicyclic nucleoside having Formula III:

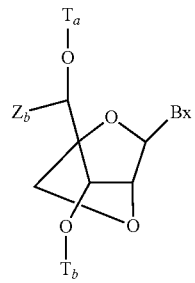

III wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(=O)—).

In certain embodiments, bicyclic nucleoside having Formula IV:

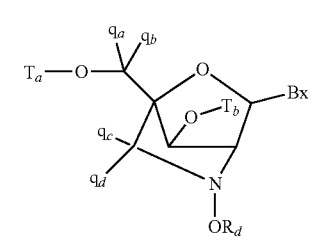

IV wherein:
Bx is a heterocyclic base moiety;
$T_a$ and $T_b$ are each, independently H, a hydroxyl protecting group, a conjugate group, a reactive phosphorus group, a phosphorus moiety, or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl, or substituted $C_1$-$C_6$ aminoalkyl;

In certain embodiments, bicyclic nucleoside having Formula V:

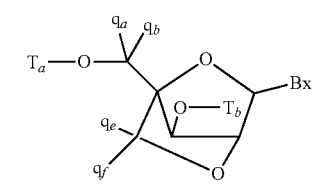

V wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;
or $q_e$ and $q_f$ together are =C($q_g$)($q_h$);
$q_g$ and $q_h$ are each, independently, H, halogen, $C_1$-$C_{12}$ alkyl, or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$—O-2') BNA, and 2'-thio-BNAs, have also been prepared (see, e.g., Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel comformationally restricted high-affinity oligonucleotide analog, has been described in the art (see, e.g., Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleoside having Formula VI:

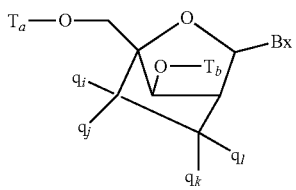

VI wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$, or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl, or substituted $C_1$-$C_{12}$ alkyl.

One carbocyclic bicyclic nucleoside having a 4'-($CH_2$)$_3$-2' bridge and the alkenyl analog, bridge 4'-CH=CH—$CH_2$-2', have been described (see, e.g., Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (see, e.g., Srivastava et al., *J Am. Chem. Soc.* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom.

As used herein, "monocyclic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[($CH_2$)$_n$O]$_m$$CH_3$, O($CH_2$)$_n$$NH_2$, O($CH_2$)$_n$$CH_3$, O($CH_2$)$_n$$ONH_2$, $OCH_2$C(=O)N(H)$CH_3$, and O($CH_2$)$_n$ON[($CH_2$)$_n$$CH_3$]$_2$, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; $SCH_3$; OCN; Cl; Br; CN; $CF_3$; $OCF_3$; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving pharmacokinetic properties; and a group for improving the pharmacodynamic properties of an antisense compound, and other substituents having similar properties. In certain embodiments, modified nucleosides comprise a 2'-MOE side chain (see, e.g., Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (see, e.g., Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), mannitol nucleic acid (MNA) (see Leumann, C J. *Bioorg. & Med. Chem.* (2002) 10:841-854), fluoro HNA (F-HNA), or those compounds having Formula X:

Formula X:

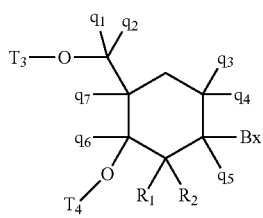

wherein independently for each of said at least one tetrahydropyran nucleoside analog of Formula X:
Bx is a heterocyclic base moiety;
$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;
$q_1$, $q_2$, $q_3$, $q_4$, $q_5$, $q_6$ and q are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and
one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S, or $NJ_1$, and each $J_1$, $J_2$, and $J_3$ is, independently, H or $C_1$-$C_6$ alkyl.

In certain embodiments, the modified THP nucleosides of Formula X are provided wherein $q_m$, $q_n$, $q_p$, $q_r$, $q_s$, $q_t$, and $q_u$ are each H. In certain embodiments, at least one of $q_m$, $q_n$, $q_p$, $q_r$, $q_s$, $q_t$, and $q_u$ is other than H. In certain embodiments, at least one of $q_m$, $q_n$, $q_p$, $q_r$, $q_s$, $q_t$ and $q_u$ is methyl. In certain embodiments, THP nucleosides of Formula X are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N(Rm)(Rn), or O—$CH_2$—C(=O)—N(Rm)(Rn), where each Rm and $R_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see, e.g., review article: Leumann, J. C, Bioorganic & Medicinal Chemistry, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified, or a combination thereof) are maintained for hybridization with an appropriate nucleic acid target.

In certain embodiments, antisense compounds comprise one or more nucleotides having modified sugar moieties. In certain embodiments, the modified sugar moiety is 2'-MOE. In certain embodiments, the 2'-MOE modified nucleotides are arranged in a gapmer motif. In certain embodiments, the modified sugar moiety is a cEt. In certain embodiments, the cEt modified nucleotides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an alpha-synuclein nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an alpha-synuclein nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of alpha-synuclein nucleic acids can be tested in vitro in a variety of cell types. Cell types used for such analyses are available from commercial vendors (e.g. American Type Culture Collection, Manassas, VA; Zen-Bio, Inc., Research Triangle Park, NC; Clonetics Corporation, Walkersville, MD) and are cultured according to the vendor's instructions using commercially available reagents (e.g. Invitrogen Life Technologies, Carlsbad, CA). Illustrative cell types include, but are not limited to, HuVEC cells and SH-SY5Y cells.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, CA). Antisense oligonucleotides may be mixed with LIPOFECTIN in OPTI-MEM 1 (Invitrogen, Carlsbad, CA) to achieve the desired final concentration of antisense oligonucleotide and a LIPOFECTIN concentration that may range from 2 to 12 μg/mL per 100 nM antisense oligonucleotide.

Another reagent used to introduce antisense oligonucleotides into cultured cells includes LIPOFECTAMINE (Invitrogen, Carlsbad, CA). Antisense oligonucleotide is mixed with LIPOFECTAMINE in OPTI-MEM 1 reduced serum medium (Invitrogen, Carlsbad, CA) to achieve the desired concentration of antisense oligonucleotide and a LIPOFECTAMINE concentration that may range from 2 to 12 μg/mL per 100 nM antisense oligonucleotide.

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, CA) according to the manufacturer's recommended protocols.

Analysis of Inhibition of Target Levels or Expression

Inhibition of levels or expression of an alpha-synuclein nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, CA and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, CA) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, CA). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, CA). Cyclophilin A expression is quantified by real time PCR, by being run simultaneously with the target, multiplexing, or separately. Total RNA is quantified using RIBOGREEN RNA quantification reagent (Invetrogen, Inc. Eugene, OR). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to an alpha-synuclein nucleic acid. Methods for designing real-time PCR probes and primers are well known in the art, and may include the use of software such as PRIMER EXPRESS Software (Applied Biosystems, Foster City, CA).

Analysis of Protein Levels

Antisense inhibition of alpha-synuclein nucleic acids can be assessed by measuring alpha-synuclein protein levels. Protein levels of alpha-synuclein can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, MI), or can be prepared via conventional monoclonal or polyclonal antibody generation methods well known in the art. Antibodies useful for the detection of mouse, rat, monkey, and human alpha-synuclein are commercially available.

In Vivo Testing of Antisense Compounds

Antisense compounds, for example, antisense oligonucleotides, are tested in animals to assess their ability to inhibit expression of alpha-synuclein and produce phenotypic changes, such as, improved motor coordination, improved olfaction, improved spatial memory, reduced incidence of resting tremor, reduced incidence of bradykinesia (slow movement), reduced rigidity or inflexibility, improved balance, improved fine motor dexterity, improved gross motor coordination, reduced aggregation of alpha-synuclein, and improved autonomic function, such as, decreased orthostatic hypotension. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, subcutaneous, intramuscular, intraarterial, or intracranial administration, e.g., intrathecal or intracerebroventricular administration. Calculation of antisense oligonucleotide dosage and dosing frequency depends upon many factors such as route of administration and animal body weight. Following a period of treatment with antisense oligonucleotides, RNA is isolated from liver tissue and changes in alpha-synuclein nucleic acid expression are measured. Changes in alpha-synuclein protein levels are also measured.

Certain Indications

In certain embodiments, the invention provides methods, compounds, and compositions of treating an individual comprising administering one or more pharmaceutical compositions of the present invention. In certain embodiments, the individual has a neurodegenerative disease. In certain embodiments, the neurodegenerative disease is Parkinson's Disease, dementia, multiple system atrophy (also Shy-Drager syndrome), sporadic and familial Alzheimer's Disease, Lewy body variant of Alzheimer's disease, diffuse Lewy body disease, or dementia with Lewy bodies. In certain embodiments, the individual has a synucleinopathy. In certain embodiments, the synucleinopathy is Parkinson's Disease, dementia with Lewy bodies, or multiple system atrophy. In certain embodiments, the individual is at risk for developing a neurodegenerative disease and/or a synucleinopathy. This includes individuals having one or more risk factors for developing a neurodegenerative disease and/or synucleinopathy, including, include older age, exposure to neurotoxins, and genetic predisposition. In certain embodiments, the individual has been identified as in need of treatment for a neurodegenerative disease and/or synucleinopathy. In certain embodiments the invention provides methods for prophylactically reducing alpha-synuclein expression in an individual. Certain embodiments include treating an individual in need thereof by administering to an individual a therapeutically effective amount of an antisense compound targeted to an alpha-synuclein nucleic acid.

In certain embodiments, administration of an antisense compound targeted to an alpha-synuclein nucleic acid results in reduction of alpha-synuclein expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to an alpha-synuclein nucleic acid results in improved motor coordination, improved olfaction, improved spatial memory, reduced incidence of resting tremor, reduced incidence of bradykinesia (slow movement), reduced rigidity or inflexibility, improved balance, improved fine motor dexterity, improved gross motor coordination, reduced aggregation of alpha-synuclein, and improved autonomic function, such as, decreased orthostatic hypotension. In certain embodiments, administration of an alpha-synuclein antisense compound improves motor coordination, reduces incidence of resting tremor, reduces incidence of bradykinesia (slow movement), reduces rigidity or inflexibility, improves balance, improves fine motor dexterity, improves gross motor coordination, reduces aggregation of alpha-synuclein, improves autonomic function, and decreases orthostatic hypotension by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to alpha-synuclein are used for the preparation of a medicament for treating a patient suffering or susceptible to a neurodegenerative disease and/or synucleinopathy.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

Certain Combination Therapies

In certain embodiments, one or more pharmaceutical compositions of the present invention are co-administered with one or more other pharmaceutical agents. In certain embodiments, one or more pharmaceutical compositions of the present invention are antisense oligonucleotides. In certain embodiments, one or more other pharmaceutical agents are any of peptides, antibodies, or small molecules. In certain embodiments, the peptides, antibodies, or small molecules are any of those described hereinabove (e.g., see Certain Embodiments above).

In certain embodiments, such one or more other pharmaceutical agents are designed to treat the same disease, disorder, or condition as the one or more pharmaceutical compositions of the present invention. In certain embodiments, such one or more other pharmaceutical agents are designed to treat a different disease, disorder, or condition as the one or more pharmaceutical compositions of the present invention. In certain embodiments, such one or more other pharmaceutical agents are designed to treat an undesired side effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention are co-administered with another pharmaceutical agent to produce a combinational effect. In certain embodiments, one or more pharmaceutical compositions of the present invention are co-administered with another pharmaceutical agent to produce a synergistic effect.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately. In certain embodiments, one or more other pharmaceutical agents include levodopa, dopamine agonists, COMT inhibitors, and antidepressants.

In certain embodiments, one more pharmaceutical compositions of the present invention are administered with physical therapy.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Alpha-Synuclein (SNCA) in HuVEC Cells

Antisense oligonucleotides targeted to an SNCA nucleic acid were tested for their effects on SNCA mRNA in vitro. Cultured HuVEC cells at a density of 5,000 cells per well were transfected using LipofectAMINE2000® reagent with 10 nM antisense oligonucleotide. After a treatment period of approximately 24 hours, RNA was isolated from the cells and SNCA mRNA levels were measured by quantitative real time PCR using the human primer probe set RTS2621 (forward sequence ACGAACCTGAAGCCTAAGAAATATCT, designated herein as SEQ ID NO: 8; reverse sequence GAGCACTTGTACAGGATGGAACAT, designated herein as SEQ ID NO: 9; probe sequence TGCTCCCAGTTTCTTGAGATCTGCTGACA, designated herein as SEQ ID NO: 10). SNCA mRNA levels were adjusted according to total RNA content, as measured by RIBOGREEN. Results are presented as percent inhibition of SNCA, relative to untreated control cells.

The chimeric antisense oligonucleotides in Tables 1, 2, and 3 were designed as 5-10-5 MOE gapmers. The gapmers are 20 nucleosides in length, wherein the central gap segment is comprised of ten 2'-deoxynucleosides and is flanked on both sides (in the 5' and 3' directions) by wings comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytidine residues throughout each gapmer are 5-methylcytidines. "Start site" indicates the 5'-most nucleoside to which the gapmer is targeted in the human gene sequence. "Stop site" indicates the 3'-most nucleoside to which the gapmer is targeted in the human gene sequence. Each gapmer listed in Table 1 is targeted to SEQ ID NO: 1 (GENBANK Accession No. NM_000345.3). Each gapmer listed in Table 2 is targeted to SEQ ID NO: 2 (the complement of GENBANK Accession No. NT_016354.17 truncated from nucleotides 15140000 to Ser. No. 15/255,000). Each gapmer listed in Table 3 is targeted to either SEQ ID NO: 3 (GENBANK Accession No. NM_007308.1), SEQ ID NO: 4 (GENBANK Accession No. L36674.1), SEQ ID NO: 5 (GENBANK Accession No. BC013293.2), SEQ ID NO: 6 (GENBANK Accession No. BG701026.1), or SEQ ID NO: 7 (GENBANK Accession No. BM069769.1).

As shown in Tables 1 and 2, several of the gapmers exhibited at least 50% inhibition, as measured by primer probe set RTS2621, including ISIS numbers: 387973, 387974, 387975, 387976, 387977, 387978, 387979, 387980, 387981, 387982, 387983, 387984, 387985, 387986, 387987, 387988, 387989, 387990, 387991, 387994, 387995, 387996, 387997, 387998, 387999, 388000, 388001, 388002, 388004, 388005, 388006, 388007, 388008, 388009, 388010, 388012, 388013, 388014, 388016, 388017, 388021, 388025, 388026, 388027, 388029, 388032, 388033, and 3880309.

Several of the gapmers exhibited at least 60% inhibition, including ISIS numbers: 387973, 387974, 387975, 387976, 387977, 387978, 387979, 387980, 387981, 387982, 387983, 387984, 387985, 387986, 387988, 387989, 387990, 387994, 387995, 387996, 387997, 387998, 387999, 388000, 388001, 388002, 388004, 388005, 388006, 388007, 388008, 388009, 388010, 388014, 388016, 388017, 388026, 388027, 388029, 388032, 388033, and 388039.

Several of the gapmers exhibited at least 70% inhibition, including ISIS numbers: 387973, 387974, 387975, 387976, 387977, 387978, 387979, 387980, 387981, 387982, 387983, 387984, 387985, 387986, 387989, 387994, 387995, 387996, 387997, 387998, 387999, 388000, 388001, 388004, 388006, 388008, 388009, 388010, 388014, 388016, 388017, 388027, 388029, and 388039.

Several of the gapmers exhibited at least 80% inhibition, including ISIS numbers: 387973, 387974, 387975, 387976, 387978, 387979, 387981, 387983, 387984, 387985, 387986, 387994, 387998, 387999, 388000, 388001, 388004, 388006, 388008, 388009, 388010, 388014, 388016, and 388017.

Several of the gapmers exhibited at least 90% inhibition, including ISIS numbers: 387973, 387975, 387983, 387984, 387985, 387986, 387994, 387998, and 388004.

TABLE 1

Inhibition of human SNCA mRNA levels by chimeric antisense oligonucleotides having 5-10-5 MOE wings and deoxy gap targeted to SEQ ID NO: 1

| Start Site | Stop Site | Oligo ID | Sequence | % inhibition | SEQ ID NO |
|---|---|---|---|---|---|
| 236 | 255 | 387973 | AATTCCTTTACACCACACTG | 92 | 11 |
| 246 | 265 | 387974 | ATGGCTAATGAATTCCTTTA | 89 | 12 |
| 256 | 275 | 387975 | GAATACATCCATGGCTAATG | 90 | 13 |
| 266 | 285 | 387976 | GTCCTTTCATGAATACATCC | 89 | 14 |
| 273 | 292 | 387977 | TTTGAAAGTCCTTTCATGAA | 78 | 15 |
| 282 | 301 | 387978 | TCCTTGGCCTTTGAAAGTCC | 88 | 16 |
| 304 | 323 | 387979 | CTCAGCAGCAGCCACAACTC | 80 | 17 |
| 312 | 331 | 387980 | TTGGTTTTCTCAGCAGCAGC | 77 | 18 |
| 361 | 380 | 387981 | ATAGAGAACACCCTCTTTTG | 83 | 19 |
| 375 | 394 | 387982 | GTTTTGGAGCCTACATAGAG | 77 | 20 |
| 381 | 400 | 387983 | TCCTTGGTTTTGGAGCCTAC | 91 | 21 |
| 404 | 423 | 387984 | TTGCCACACCATGCACCACT | 92 | 22 |
| 444 | 463 | 387985 | CCAACATTTGTCACTTGCTC | 95 | 23 |
| 469 | 488 | 387986 | TGTCACACCCGTCACCACTG | 96 | 24 |
| 542 | 561 | 387987 | ACTGGTCCTTTTTGACAAAG | 58 | 25 |
| 554 | 573 | 387988 | CATTCTTGCCCAACTGGTCC | 65 | 26 |
| 607 | 626 | 387989 | GTCAGGATCCACAGGCATAT | 78 | 27 |
| 622 | 641 | 387990 | TTCATAAGCCTCATTGTCAG | 63 | 28 |
| 629 | 648 | 387991 | AAGGCATTTCATAAGCCTCA | 52 | 29 |
| 637 | 656 | 387992 | TTCCTCAGAAGGCATTTCAT | 39 | 30 |
| 644 | 663 | 387993 | GATACCCTTCCTCAGAAGGC | 40 | 31 |
| 653 | 672 | 387994 | CGTAGTCTTGATACCCTTCC | 93 | 32 |
| 671 | 690 | 387995 | TTTCTTAGGCTTCAGGTTCG | 77 | 33 |
| 676 | 695 | 387996 | AGATATTTCTTAGGCTTCAG | 71 | 34 |
| 683 | 702 | 387997 | GGAGCAAAGATATTTCTTAG | 77 | 35 |
| 702 | 721 | 387998 | AGCAGATCTCAAGAAACTGG | 92 | 36 |
| 734 | 753 | 387999 | ACTGAGCACTTGTACAGGAT | 86 | 37 |
| 739 | 758 | 388000 | TTGGAACTGAGCACTTGTAC | 87 | 38 |
| 745 | 764 | 388001 | GGCACATTGGAACTGAGCAC | 87 | 39 |
| 764 | 783 | 388002 | TTGAGAAATGTCATGACTGG | 67 | 40 |
| 774 | 793 | 388003 | TGTAAAACTTTGAGAAATG | 31 | 41 |
| 792 | 811 | 388004 | GAAGACTTCGAGATACACTG | 94 | 42 |
| 808 | 827 | 388005 | TCAATCACTGCTGATGGAAG | 66 | 43 |
| 818 | 837 | 388006 | TACAGATACTTCAATCACTG | 82 | 44 |
| 881 | 900 | 388007 | GACCCTGCTACCATGTATTC | 68 | 45 |
| 891 | 910 | 388008 | AGCACACAAAGACCCTGCTA | 88 | 46 |
| 897 | 916 | 388009 | ATCCACAGCACACAAAGACC | 80 | 47 |
| 908 | 927 | 388010 | GAAGCCACAAAATCCACAGC | 86 | 48 |
| 952 | 971 | 388011 | GGTAGTCACTTAGGTGTTTT | 49 | 49 |
| 958 | 977 | 388012 | ATAAGTGGTAGTCACTTAGG | 57 | 50 |
| 964 | 983 | 388013 | TTAGAAATAAGTGGTAGTCA | 57 | 51 |
| 1001 | 1020 | 388014 | AACTTCTGAACAACAGCAAC | 82 | 52 |
| 1030 | 1049 | 388015 | CTTATAATATATGATAGCAA | 34 | 53 |
| 1055 | 1074 | 388016 | GTATCATTAAAAGACACCTA | 86 | 54 |
| 1072 | 1091 | 388017 | GTCATTATTCTTAGACAGTA | 82 | 55 |
| 1242 | 1261 | 388018 | TATTTTTGCAATGAGATAAC | 28 | 56 |
| 1249 | 1268 | 388019 | AATAAAATATTTTTGCAATG | 0 | 57 |
| 1292 | 1311 | 388020 | GCTTATAAGCATGATTTTTA | 31 | 58 |
| 1302 | 1321 | 388021 | AATTCATGTTGCTTATAAGC | 51 | 59 |
| 1314 | 1333 | 388022 | GTGTCAGTTCTTAATTCATG | 20 | 60 |
| 1345 | 1364 | 388023 | GGCTATTAATAACTTATAT | 29 | 61 |
| 1355 | 1374 | 388024 | TTCTTCAAATGGCTATTAAT | 45 | 62 |
| 1432 | 1451 | 388025 | TTCTGGCAGTGTTGCTTCAG | 59 | 63 |
| 1452 | 1471 | 388026 | CAGTGCATACCAAAACACAC | 61 | 64 |
| 1462 | 1481 | 388027 | CTTAAGGAACCAGTGCATAC | 77 | 65 |
| 1472 | 1491 | 388028 | ATCACAGCCACTTAAGGAAC | 31 | 66 |
| 1482 | 1501 | 388029 | TCAATAATTAATCACAGCCA | 70 | 67 |
| 1522 | 1541 | 388030 | CCACTCTACAATAGTAGTTG | 44 | 68 |
| 1693 | 1712 | 388031 | TATCAGACAAAATAGATTTT | 0 | 69 |
| 1703 | 1722 | 388032 | TTCACACCAATATCAGACAA | 67 | 70 |
| 1723 | 1742 | 388033 | ATTGTCAGAAAGGTACAGCA | 64 | 71 |
| 1733 | 1752 | 388034 | AATATTATTTATTGTCAGAA | 0 | 72 |
| 1741 | 1760 | 388035 | CATGGTCGAATATTATTTAT | 5 | 73 |
| 1170 | 1189 | 388037 | TCGCAAAATGGTAAAATTTC | 35 | 74 |
| 107 | 126 | 388039 | GTCTGCGCTGCAGCCCGCAC | 79 | 75 |

TABLE 2

Inhibition of human SNCA mRNA levels by chimeric antisense oligonucleotides having 5-10-5 MOE wings and deoxy gap targeted to SEQ ID NO: 2

| Start Site | Stop Site | Oligo ID | Sequence | % inhibition | SEQ ID NO |
|---|---|---|---|---|---|
| 3451 | 3470 | 387973 | AATTCCTTTACACCACACTG | 92 | 11 |
| 3461 | 3480 | 387974 | ATGGCTAATGAATTCCTTTA | 89 | 12 |
| 3471 | 3490 | 387975 | GAATACATCCATGGCTAATG | 90 | 13 |
| 3481 | 3500 | 387976 | GTCCTTTCATGAATACATCC | 89 | 14 |
| 3488 | 3507 | 387977 | TTTGAAAGTCCTTTCATGAA | 78 | 15 |
| 3497 | 3516 | 387978 | TCCTTGGCCTTTGAAAGTCC | 88 | 16 |
| 3519 | 3538 | 387979 | CTCAGCAGCAGCCACAACTC | 80 | 17 |
| 3527 | 3546 | 387980 | TTGGTTTTCTCAGCAGCAGC | 77 | 18 |
| 3576 | 3595 | 387981 | ATAGAGAACACCCTCTTTTG | 83 | 19 |
| 10958 | 10977 | 387983 | TCCTTGGTTTTGGAGCCTAC | 91 | 21 |
| 10981 | 11000 | 387984 | TTGCCACACCATGCACCACT | 92 | 22 |
| 16775 | 16794 | 387985 | CCAACATTTGTCACTTGCTC | 95 | 23 |
| 16800 | 16819 | 387986 | TGTCACACCCGTCACCACTG | 96 | 24 |
| 16873 | 16892 | 387987 | ACTGGTCCTTTTTGACAAAG | 58 | 25 |
| 109906 | 109925 | 387989 | GTCAGGATCCACAGGCATAT | 78 | 27 |
| 109921 | 109940 | 387990 | TTCATAAGCCTCATTGTCAG | 63 | 28 |
| 109928 | 109947 | 387991 | AAGGCATTTCATAAGCCTCA | 52 | 29 |
| 112485 | 112504 | 387994 | CGTAGTCTTGATACCCTTCC | 93 | 32 |
| 112503 | 112522 | 387995 | TTTCTTAGGCTTCAGGTTCG | 77 | 33 |
| 112508 | 112527 | 387996 | AGATATTCTTAGGCTTCAG | 71 | 34 |
| 112515 | 112534 | 387997 | GGAGCAAAGATATTCTTAG | 77 | 35 |
| 112534 | 112553 | 387998 | AGCAGATCTCAAGAAACTGG | 92 | 36 |
| 112566 | 112585 | 387999 | ACTGAGCACTTGTACAGGAT | 86 | 37 |
| 112571 | 112590 | 388000 | TTGGAACTGAGCACTTGTAC | 87 | 38 |
| 112577 | 112596 | 388001 | GGCACATTGGAACTGAGCAC | 87 | 39 |
| 112596 | 112615 | 388002 | TTGAGAAATGTCATGACTGG | 67 | 40 |
| 112606 | 112625 | 388003 | TGTAAAAACTTTGAGAAATG | 31 | 41 |
| 112624 | 112643 | 388004 | GAAGACTTCGAGATACACTG | 94 | 42 |
| 112640 | 112659 | 388005 | TCAATCACTGCTGATGGAAG | 66 | 43 |
| 112650 | 112669 | 388006 | TACAGATACTTCAATCACTG | 82 | 44 |
| 112713 | 112732 | 388007 | GACCCTGCTACCATGTATTC | 68 | 45 |
| 112723 | 112742 | 388008 | AGCACACAAAGACCCTGCTA | 88 | 46 |
| 112729 | 112748 | 388009 | ATCCACAGCACACAAAGACC | 80 | 47 |
| 112740 | 112759 | 388010 | GAAGCCACAAAATCCACAGC | 86 | 48 |
| 112784 | 112803 | 388011 | GGTAGTCACTTAGGTGTTTT | 49 | 49 |
| 112790 | 112809 | 388012 | ATAAGTGGTAGTCACTTAGG | 57 | 50 |
| 112796 | 112815 | 388013 | TTAGAAATAAGTGGTAGTCA | 57 | 51 |
| 112833 | 112852 | 388014 | AACTTCTGAACAACAGCAAC | 82 | 52 |
| 112862 | 112881 | 388015 | CTTATAATATATGATAGCAA | 34 | 53 |
| 112887 | 112906 | 388016 | GTATCATTAAAAGACACCTA | 86 | 54 |
| 112904 | 112923 | 388017 | GTCATTATTCTTAGACAGTA | 82 | 55 |
| 113074 | 113093 | 388018 | TATTTTTGCAATGAGATAAC | 28 | 56 |
| 113081 | 113100 | 388019 | AATAAAATATTTTTGCAATG | 0 | 57 |
| 113124 | 113143 | 388020 | GCTTATAAGCATGATTTTTA | 31 | 58 |
| 113134 | 113153 | 388021 | AATTCATGTTGCTTATAAGC | 51 | 59 |
| 113146 | 113165 | 388022 | GTGTCAGTTCTTAATTCATG | 20 | 60 |
| 113177 | 113196 | 388023 | GGCTATTAATAACTTTATAT | 29 | 61 |
| 113187 | 113206 | 388024 | TTCTTCAAATGGCTATTAAT | 45 | 62 |
| 113264 | 113283 | 388025 | TTCTGGCAGTGTTGCTTCAG | 59 | 63 |
| 113284 | 113303 | 388026 | CAGTGCATACCAAAACACAC | 61 | 64 |
| 113294 | 113313 | 388027 | CTTAAGGAACCAGTGCATAC | 77 | 65 |
| 113304 | 113323 | 388028 | ATCACAGCCACTTAAGGAAC | 31 | 66 |
| 113314 | 113333 | 388029 | TCAATAATTAATCACAGCCA | 70 | 67 |
| 113354 | 113373 | 388030 | CCACTCTACAATAGTAGTTG | 44 | 68 |
| 113525 | 113544 | 388031 | TATCAGACAAAATAGATTTT | 0 | 69 |
| 113535 | 113554 | 388032 | TTCACACCAATATCAGACAA | 67 | 70 |
| 113555 | 113574 | 388033 | ATTGTCAGAAAGGTACAGCA | 64 | 71 |
| 113565 | 113584 | 388034 | AATATTATTTATTGTCAGAA | 0 | 72 |
| 113573 | 113592 | 388035 | CATGGTCGAATATTATTTAT | 5 | 73 |
| 113002 | 113021 | 388037 | TCGCAAAATGGTAAAATTTC | 35 | 74 |
| 2053 | 2072 | 388039 | GTCTGCGCTGCAGCCCGCAC | 79 | 75 |
| 2183 | 2202 | 388040 | GGAGGCAAACCCGCTAACCT | 63 | 76 |
| 3590 | 3609 | 388042 | GTTTACCTACCTACATAGAG | 8 | 77 |
| 10952 | 10971 | 388043 | GTTTTGGAGCCTACAAAAAC | 56 | 78 |
| 16748 | 16767 | 388044 | TTCTCAGCCACTGGTACAAA | 40 | 79 |
| 49342 | 49361 | 388045 | CCATTCCCAAGAGACCCAGA | 92 | 80 |
| 73617 | 73636 | 388046 | AGAAGAATCAATTGCTTTAC | 85 | 81 |
| 94236 | 94255 | 388047 | TAATCATTTAAACCTTAGTA | 32 | 82 |
| 112476 | 112495 | 388048 | GATACCCTTCCTAATATTAG | 46 | 83 |

TABLE 3

Inhibition of human SNCA mRNA levels by chimeric antisense oligonucleotides having 5-10-5 MOE wings and deoxy gap targeted to SEQ ID NOs: 3-7

| Target SEQ ID NO | Start Site | Stop Site | Oligo ID | Sequence | % inhibition | SEQ ID NO |
|---|---|---|---|---|---|---|
| 3 | 310 | 329 | 388036 | GATACCCTTCCTTGCCCAAC | 12 | 84 |
| 4 | 124 | 143 | 388038 | GCCACTACATAGAGAACACC | 78 | 85 |
| 5 | 392 | 411 | 388041 | CCTTTACACCACACTGAGTC | 91 | 86 |
| 6 | 595 | 614 | 388049 | ATATCTGCCAGAATGTCCTT | 86 | 87 |
| 7 | 62 | 81 | 388050 | TTACACCACACTCACTTCCG | 55 | 88 |

Example 2: Dose-Dependent Antisense Inhibition of Human SNCA in HuVEC Cells

Eleven gapmers, exhibiting over 84 percent or greater in vitro inhibition of human SNCA in the study described in Example 1, were tested at various doses in HuVEC cells. Cells were plated at a density of 6,000 cells per well and transfected using LipofectAMINE2000® reagent with 0.08 nM, 0.25 nM, 0.74 nM, 2.22 nM, 6.67 nM, and 20.00 nM concentrations of antisense oligonucleotide, as specified in Table 4. After a treatment period of approximately 16 hours, RNA was isolated from the cells and SNCA mRNA levels were measured by quantitative real-time PCR. Human SNCA primer probe set RTS2621 (described herein above in Example 1) was used to measure mRNA levels. SNCA mRNA levels were adjusted according to total RNA content, as measured by RIBOGREEN. Results are presented as percent inhibition of SNCA, relative to untreated control cells. As illustrated in Table 4, SNCA mRNA levels were reduced in a dose-dependent manner in antisense oligonucleotide treated cells.

TABLE 4

Dose-dependent antisense inhibition of human SNCA in HuVEC cells

| Oligo ID | 0.08 nM | 0.25 nM | 0.74 nM | 2.22 nM | 6.67 nM | 20.00 nM | IC$_{50}$ (nM) |
|---|---|---|---|---|---|---|---|
| 387973 | 0 | 11 | 23 | 46 | 72 | 81 | 2.6 |
| 387975 | 9 | 8 | 25 | 57 | 72 | 83 | 2.1 |
| 387978 | 13 | 28 | 39 | 68 | 81 | 89 | 1.1 |
| 387983 | 0 | 8 | 17 | 49 | 75 | 85 | 2.6 |
| 387984 | 3 | 15 | 30 | 66 | 82 | 86 | 1.5 |
| 387985 | 0 | 6 | 24 | 66 | 77 | 89 | 1.8 |
| 387986 | 0 | 17 | 33 | 67 | 77 | 84 | 1.7 |
| 388004 | 0 | 11 | 30 | 65 | 78 | 86 | 1.8 |
| 388008 | 2 | 0 | 26 | 59 | 77 | 88 | 2.1 |
| 388010 | 0 | 8 | 24 | 54 | 71 | 87 | 2.3 |
| 388041 | 0 | 10 | 27 | 55 | 77 | 86 | 2.2 |

Example 3: Dose-Dependent Antisense Inhibition of Human SNCA in SH-SY5Y Cells Gapmers were selected from the study described in Example 2 and tested at various doses in SH-SY5Y cells. Cells were plated at a density of 20,000 cells per well and transfected using electroporation with 5 µM, 10 µM, and 20 µM concentrations of antisense oligonucleotide, as specified in Table 5. After a treatment period of approximately 16 hours, RNA was isolated from the cells and SNCA mRNA levels were measured by quantitative real-time PCR. Human SNCA primer probe set RTS2620 (forward sequence GGTGCTTCCCTTTCACTGAAGT, designated herein as SEQ ID NO: 89; reverse sequence ACATCGTAGATTGAAGCCACAAAA, designated herein as SEQ ID NO: 90, probe sequence AATACATGGTAGCAGGGTCTTTGTGTGCTGTG, designated herein as SEQ ID NO: 91) was used to measure mRNA levels. SNCA mRNA levels were adjusted according to total RNA content, as measured by RIBOGREEN. Results are presented as percent inhibition of SNCA, relative to untreated control cells. As illustrated in Table 5, SNCA mRNA levels were reduced in a dose-dependent manner in antisense oligonucleotide treated cells.

TABLE 5

Dose-dependent antisense inhibition of human SNCA in SH-SY5Y cells

| Oligo ID | 5 µM | 10 µM | 20 µM |
|---|---|---|---|
| 387978 | 79 | 85 | 94 |
| 387984 | 79 | 92 | 96 |
| 387985 | 54 | 82 | 93 |
| 387986 | 63 | 84 | 91 |
| 388004 | 71 | 88 | 92 |

Example 4: Tolerability of Antisense Oligonucleotides Targeting Human SNCA in a Mouse Model ISIS oligonucleotides that demonstrated dose-dependent inhibition in the studies described herein in Examples 2 and 3 were evaluated for tolerability in a mouse model by monitoring changes in the levels of various metabolic markers in C57BL/6 mice.

Treatment

C57BL/6 mice were injected with 50 mg/kg of ISIS 387973, ISIS 387975, ISIS 387978, ISIS 387983, ISIS 387984, ISIS 387985, ISIS 387986, ISIS 388004, ISIS 388008, ISIS 388010, or ISIS 388041 administered subcutaneously twice a week for 3 weeks. A control group of mice was injected with phosphate buffered saline (PBS) administered subcutaneously twice a week for 3 weeks. Mice were sacrificed 48 hrs after receiving the last dose. Plasma was collected for further analysis.

Liver Function

To evaluate the effect of ISIS oligonucleotides on hepatic function, plasma concentrations of transaminases were measured using an automated clinical chemistry analyzer (Hitachi Olympus AU400e, Melville, NY). Plasma concentrations of ALT (alanine transaminase) and AST (aspartate transaminase) were measured at the end of the treatment period. The results presented in Table 6 indicate that liver transaminases were within normal parameters for all the ISIS oligonucleotides, except for ISIS 387986.

TABLE 6

Effect of antisense oligonucleotide treatment on ALT and AST (IU/L) of C57BL/6 mice

|  | ALT | AST |
|---|---|---|
| PBS | 32 | 62 |
| ISIS 387973 | 37 | 65 |
| ISIS 387975 | 67 | 94 |
| ISIS 387978 | 33 | 51 |
| ISIS 387983 | 45 | 81 |
| ISIS 387984 | 60 | 75 |
| ISIS 387985 | 30 | 49 |
| ISIS 387986 | 780 | 384 |
| ISIS 388004 | 36 | 59 |
| ISIS 388008 | 48 | 66 |
| ISIS 388010 | 73 | 79 |
| ISIS 388041 | 61 | 90 |

Body and Organ Weights

The body weights of the mice, as well as liver, spleen and kidney weights were measured at the end of the study. All the weights measured were within 13% that of the corresponding weights in the PBS control. The results demonstrate that none of the ISIS oligonucleotides had any adverse effect on the overall health of the mice.

Example 5: Potency of Antisense Oligonucleotides Targeting Human SNCA in a Transgenic Mouse Model (SNCA PAC Mice)

The ISIS oligonucleotides were further evaluated for potency in the SNCA PAC (PAC-Tg(SNCA$^{WT}$) Snca$^{-/-}$) transgenic mouse model. These mice harbor a knockout Snca allele and a transgene encoding human SNCA under a PAC (P1 artificial chromosome construct) promoter.

Treatment

Groups of 4 SNCA PAC mice each were injected with 100 µg of ISIS 387973, ISIS 387975, ISIS 387978, ISIS 387983, ISIS 387984, ISIS 387985, ISIS 388004, ISIS 388008, ISIS 388010, or ISIS 388041 administered via an intrastriatal bolus injection. A control group of mice was injected with phosphate buffered saline (PBS) administered via an intrastriatal bolus injection. Mice were sacrificed 2 weeks after receiving the injection. Brain tissue was collected for further analysis.

RNA Analysis

RNA was extracted from the striatal and cortical tissues of the brain for real-time PCR analysis of human SNCA mRNA. The results are presented in Table 7, and demonstrate that most of the ISIS oligonucleotides inhibit human SNCA mRNA significantly compared to the PBS control.

TABLE 7

Percent inhibition of human SNCA mRNA in SNCA PAC mice compared to the PBS control

| Oligo ID | Striatum | Cortex |
|---|---|---|
| 387973 | 99 | 92 |
| 387975 | 93 | 65 |
| 387978 | 39 | 69 |
| 387983 | 97 | 65 |
| 387984 | 90 | 78 |
| 387985 | 98 | 75 |
| 388004 | 98 | 54 |
| 388008 | 0 | 0 |
| 388010 | 0 | 15 |
| 388041 | 99 | 74 |

Example 6: Antisense Inhibition of Human SNCA in SH-SY5Y Cells by Oligonucleotides Designed by Microwalk Additional gapmers were designed targeting the region of the SNCA gene between the target sites of ISIS 387984 (start site 404 of SEQ ID NO: 1) and ISIS 387985 (start site 444 of SEQ ID NO: 1), which demonstrated significant inhibition of SNCA mRNA. These gapmers were designed by creating gapmers shifted by one nucleobase from each other (i.e. "microwalk") of the region between the two gapmers. The new antisense oligonucleotides were designed as 5-10-5 gapmers. These gapmers were tested in vitro. ISIS 387984 and ISIS 387985 were also included in the assay for comparison. Cultured SH-SY5Y cells at a density of 5,000 cells per well were transfected using electroporation with 2,000 nM antisense oligonucleotide. After a treatment period of approximately 24 hours, RNA was isolated from the cells and SNCA mRNA levels were measured by quantitative real-time PCR. Two human primer probe set 672 (forward sequence TGGCAGAAGCAGCAGGAAA, designated herein as SEQ ID NO: 95; reverse sequence TCCTTGGTTTTGGAGCCTACA, designated herein as SEQ ID NO: 96; probe sequence CAAAAGAGGGTGTTCTC, designated herein as SEQ ID NO: 97) and primer probe set 673 (forward sequence GGAGCAGGGAGCATTGCA, designated herein as SEQ ID NO: 92; reverse sequence CCTTCTTCATTCTTGCCCAACT, designated herein as SEQ ID NO: 93; probe sequence CACTGGCTTTGTCAAAA, designated herein as SEQ ID NO: 94) were individually used to measure SNCA mRNA levels. SNCA mRNA levels were adjusted according to total RNA content, as measured by Cyclophilin levels. Results are presented as percent inhibition of SNCA, relative to untreated control cells. The results are presented in Table 8.

The 5-10-5 MOE gapmers are 20 nucleosides in length, wherein the central gap segment is comprised of ten 2'-deoxynucleotides and is flanked on both sides (in the 5' and 3' directions) by wings comprising five nucleosides each. The internucleoside linkages throughout each gapmer are phosphorothioate (P=S) linkages. All cytidine residues throughout each gapmer are 5-methylcytidines. "Target start site" indicates the 5'-most nucleoside to which the gapmer is targeted. "Target stop site" indicates the 3'-most nucleoside to which the gapmer is targeted. Each gapmer listed in Table 8 is targeted SEQ ID NO: 1 (GENBANK Accession No. NM_000345.3).

As shown in Table 8, several of the gapmers exhibited at least 50% inhibition, as measured by primer probe set 673, including ISIS numbers: 387984, 489351, 489352, 489353, 489354, 489355, 489356, 489357, 489358, 489359, 489360, 489361, 489362, 489364, 489365, 489366, 489367, 489368, 489369, 489371, 489372, 489373, 489374, 489375, 489381, 489382, 489383, 489387, and 387985.

Several of the gapmers exhibited at least 60% inhibition, including ISIS numbers: 387984, 489351, 489352, 489353, 489355, 489356, 489357, 489358, 489359, 489360, 489361, 489366, 489371, 489372, 489373, 489374, 489381, 489383, and 387985.

Several of the gapmers exhibited at least 70% inhibition, including ISIS numbers: 387984, 489351, 489352, 489356, 489357, 489358, 489359, 489360, 489361, 489373, 489374, 489381, and 387985.

Several of the gapmers exhibited at least 80% inhibition, including ISIS numbers: 489357, 489358, 489359, and 489360.

Two of the gapmers exhibited at least 85% inhibition, including ISIS numbers: 489357 and 489358.

One gapmer exhibited at least 90% inhibition, which is ISIS 489357.

TABLE 8

Inhibition of human SNCA mRNA levels by chimeric antisense oligonucleotides targeted to SEQ ID NO: 1

| Target Start Site | Target Stop Site | Oligo ID | Sequence | % inhibition (primer probe set 672) | % inhibition (primer probe set 673) | SEQ ID NO |
|---|---|---|---|---|---|---|
| 404 | 423 | 387984 | TTGCCACACCATGCACCACT | 79 | 76 | 22 |
| 405 | 424 | 489351 | GTTGCCACACCATGCACCAC | 81 | 76 | 98 |
| 406 | 425 | 489352 | TGTTGCCACACCATGCACCA | 75 | 70 | 99 |
| 407 | 426 | 489353 | CTGTTGCCACACCATGCACC | 70 | 64 | 100 |
| 408 | 427 | 489354 | ACTGTTGCCACACCATGCAC | 62 | 56 | 101 |
| 409 | 428 | 489355 | CACTGTTGCCACACCATGCA | 67 | 61 | 102 |
| 410 | 429 | 489356 | CCACTGTTGCCACACCATGC | 82 | 79 | 103 |
| 411 | 430 | 489357 | GCCACTGTTGCCACACCATG | 92 | 90 | 104 |
| 412 | 431 | 489358 | AGCCACTGTTGCCACACCAT | 90 | 87 | 105 |
| 413 | 432 | 489359 | CAGCCACTGTTGCCACACCA | 89 | 83 | 106 |
| 414 | 433 | 489360 | TCAGCCACTGTTGCCACACC | 88 | 84 | 107 |
| 415 | 434 | 489361 | CTCAGCCACTGTTGCCACAC | 83 | 76 | 108 |
| 416 | 435 | 489362 | TCTCAGCCACTGTTGCCACA | 64 | 57 | 109 |
| 417 | 436 | 489363 | TTCTCAGCCACTGTTGCCAC | 54 | 49 | 110 |
| 418 | 437 | 489364 | CTTCTCAGCCACTGTTGCCA | 65 | 59 | 111 |
| 419 | 438 | 489365 | TCTTCTCAGCCACTGTTGCC | 58 | 53 | 112 |
| 420 | 439 | 489366 | GTCTTCTCAGCCACTGTTGC | 68 | 64 | 113 |
| 421 | 440 | 489367 | GGTCTTCTCAGCCACTGTTG | 62 | 51 | 114 |
| 422 | 441 | 489368 | TGGTCTTCTCAGCCACTGTT | 61 | 54 | 115 |
| 423 | 442 | 489369 | TTGGTCTTCTCAGCCACTGT | 61 | 53 | 116 |
| 424 | 443 | 489370 | TTTGGTCTTCTCAGCCACTG | 55 | 49 | 117 |
| 425 | 444 | 489371 | CTTTGGTCTTCTCAGCCACT | 75 | 68 | 118 |
| 426 | 445 | 489372 | TCTTTGGTCTTCTCAGCCAC | 65 | 60 | 119 |
| 427 | 446 | 489373 | CTCTTTGGTCTTCTCAGCCA | 79 | 75 | 120 |
| 428 | 447 | 489374 | GCTCTTTGGTCTTCTCAGCC | 76 | 72 | 121 |
| 429 | 448 | 489375 | TGCTCTTTGGTCTTCTCAGC | 58 | 51 | 122 |
| 430 | 449 | 489376 | TTGCTCTTTGGTCTTCTCAG | 46 | 38 | 123 |
| 431 | 450 | 489377 | CTTGCTCTTTGGTCTTCTCA | 49 | 46 | 124 |
| 432 | 451 | 489378 | ACTTGCTCTTTGGTCTTCTC | 44 | 34 | 125 |
| 433 | 452 | 489379 | CACTTGCTCTTTGGTCTTCT | 46 | 35 | 126 |
| 434 | 453 | 489380 | TCACTTGCTCTTTGGTCTTC | 50 | 45 | 127 |
| 435 | 454 | 489381 | GTCACTTGCTCTTTGGTCTT | 80 | 73 | 128 |
| 436 | 455 | 489382 | TGTCACTTGCTCTTTGGTCT | 67 | 58 | 129 |
| 437 | 456 | 489383 | TTGTCACTTGCTCTTTGGTC | 70 | 65 | 130 |
| 438 | 457 | 489384 | TTTGTCACTTGCTCTTTGGT | 42 | 31 | 131 |

TABLE 8-continued

Inhibition of human SNCA mRNA levels by chimeric
antisense oligonucleotides targeted to
SEQ ID NO: 1

| Target Start Site | Target Stop Site | Oligo ID | Sequence | % inhibition (primer probe set 672) | % inhibition (primer probe set 673) | SEQ ID NO |
|---|---|---|---|---|---|---|
| 439 | 458 | 489385 | ATTTGTCACTTGCTCTTTGG | 54 | 43 | 132 |
| 440 | 459 | 489386 | CATTTGTCACTTGCTCTTTG | 42 | 38 | 133 |
| 441 | 460 | 489387 | ACATTTGTCACTTGCTCTTT | 58 | 50 | 134 |
| 442 | 461 | 489388 | AACATTTGTCACTTGCTCTT | 46 | 39 | 135 |
| 443 | 462 | 489389 | CAACATTTGTCACTTGCTCT | 59 | 49 | 136 |
| 444 | 463 | 387985 | CCAACATTTGTCACTTGCTC | 76 | 71 | 23 |

Example 7: Potency of Antisense Oligonucleotides Targeting Human SNCA in a Transgenic Mouse Model (SNCA PAC Mice)

The ISIS oligonucleotides that demonstrated significant inhibition in the study described herein in Example 6 were further evaluated for potency in SNCA PAC mice.

Treatment

Groups of 12 SNCA PAC mice each were injected with 50 µg of ISIS 387985, ISIS 489351, ISIS 489352, ISIS 489356, ISIS 489357, ISIS 489358, ISIS 489359, ISIS 489360, ISIS 489373, ISIS 489374, ISIS 489381, or ISIS 489383 administered via an intrastriatal bolus injection. A control group of mice was injected with phosphate buffered saline (PBS) administered via an intrastriatal bolus injection. Mice were sacrificed 2 weeks after receiving the injection. Brain tissue was collected for further analysis.

RNA Analysis

RNA was extracted from the hippocampal, striatal and cortical tissues of the brain for real-time PCR analysis of human SNCA mRNA using primer probe set 673 (described herein in Example 6 above). The results are presented in Table 9, and demonstrate that most of the ISIS oligonucleotides inhibit human SNCA mRNA significantly compared to the PBS control.

TABLE 9

Percent (%) inhibition of human SNCA mRNA in
SNCA PAC mice compared to the PBS control

| Oligo ID | Cortex | Striatum | Hippocampus |
|---|---|---|---|
| 387985 | 86 | 76 | 72 |
| 489351 | 77 | 31 | 28 |
| 489352 | 81 | 38 | 54 |
| 489356 | 83 | 0 | 43 |
| 489357 | 91 | 49 | 76 |
| 489358 | 75 | 0 | 76 |
| 489359 | 81 | 62 | 65 |
| 489360 | 72 | 0 | 70 |
| 489373 | 78 | 34 | 64 |
| 489374 | 77 | 53 | 82 |
| 489381 | 73 | 34 | 72 |
| 489383 | 59 | 61 | 34 |

Example 8: Potency of Antisense Oligonucleotides Targeting Human SNCA in a Transgenic Mouse Model (Thy1-aSYN Mice)

The ISIS oligonucleotides that demonstrated significant inhibition in the study described herein in Example 7 were further evaluated in Thy1-aSYN mice.

Treatment

Groups of 4 Thy1-aSYN mice each were injected with 50 µg of ISIS 387985, ISIS 489352, ISIS 489356, and ISIS 489357 administered via an intrastriatal bolus injection. Mice were anesthetized with sodium pentobarbitone (66 mg/kg Nembutal in sterile 0.9% saline, i.p.). The scalps of the mice were then shaved and, following loss of the pedal reflex, mice were placed in a stereotaxic frame (David Kopf Instruments, CA). To maintain a surgical plane of anesthesia, mice were administered with isoflurane (1-2% in 100% oxygen at 0.5 L/min) via a nose cone, as required. The scalp was sterilized using three alternating wipes of Betadine and 70% ethanol. An incision was made in the scalp and the skull surface exposed and bregma positively identified. A hole was drilled in the skull at 0.5 mm AP, 2 mm ML, relative to bregma. ISIS 387985, ISIS 489352, ISIS 489356, and ISIS 489357 at a dose of 50 µg in a 2 µL solution was injected unilaterally into the right striatum, using a 10 uL Hamilton syringe with a 27 gauge needle connected to a microsyringe pump controller (KD Scientific 310) at a flow rate of 0.2 uL/min. The DV coordinate was measured at 3 mm below the skull surface. The needle was left in place for a further 3 minutes after injection to allow diffusion of the solution into the brain. After slowly withdrawing the syringe, the scalp was sutured and mice were subcutaneously injected with 0.5 mL warm sterile saline to aid rehydration, and placed on a warm water heat pad and monitored until they regained consciousness and mobility. A group of 4 mice was injected with PBS in a similar manner. Mice were returned to their home cage and supplied with mashed food on the cage floor. The body weights and health of mice was monitored daily post-surgery. Mice were sacrificed 2 weeks after receiving the injection. Brain tissue was collected for further analysis. A group of 4 mice was injected with PBS in a similar manner.

RNA Analysis

RNA was extracted from the striatal and cortical tissues of the brain for real-time PCR analysis of human SNCA mRNA normalized to Cyclophilin A mRNA. The results are presented in Table 10.

TABLE 10

Percent inhibition of human SNCA mRNA in Thy1-aSYN mice compared to the PBS control

| Oligo ID | Cortex | Striatum |
|---|---|---|
| 387985 | 67 | 63 |
| 489352 | 50 | 18 |
| 489356 | 56 | 20 |
| 489357 | 64 | 53 |

Protein Analysis

Protein was extracted from cell lysates of the striatal and cortical tissues of the brain and quantified by western blot analysis using anti-alpha-synuclein, clone Syn211 (Millipore, NY). The results were normalized to alpha-tubulin and are presented in Table 11.

TABLE 11

Percent inhibition of human SNCA protein levels in Thy1-aSYN mice compared to the PBS control

| Oligo ID | Cortex | Striatum |
|---|---|---|
| 387985 | 24 | 37 |
| 489352 | 30 | 51 |
| 489356 | 0 | 66 |
| 489357 | 0 | 78 |

Quantification of Antisense Oligonucleotide Levels in Brain Sections

The rostral and caudal regions of striatal and cortical tissues of the brain were individually stained using immunofluorescent antibodies against the antisense oligonucleotides (Ab6653, ISIS Pharmaceuticals, CA) or mouse anti-SNCA (BD Transduction Laboratories, CA). Images of the stained sections were acquired using a microarray scanner (Agilent Technologies, CA). Immunofluorescent intensity was quantified using ImageJ (NIH). The results of the quantification of immunofluorescence are presented in Tables 12 and 13. The results from Table 12 demonstrate the even distribution of the antisense oligonucleotides to different regions of the brain, relative to the PBS control level, which was designated zero intensity. Table 13 presents the SNCA protein levels in the corresponding brain sections, and demonstrates inhibition of SNCA by some of the ISIS oligonucleotides.

TABLE 12

Antisense oligonucleotide levels in Thy1-aSYN mice compared to the PBS control (arbitrary units)

| Oligo ID | Cortex (rostral) | Striatum (rostral) | Cortex (caudal) | Striatum (caudal) |
|---|---|---|---|---|
| 387985 | 22607 | 25225 | 29899 | 34625 |
| 489352 | 34604 | 30315 | 32535 | 36067 |
| 489356 | 26615 | 22943 | 26549 | 24441 |
| 489357 | 25219 | 25095 | 27427 | 30458 |

TABLE 13

Percent reduction in SNCA levels in Thy1-aSYN mice compared to the PBS control

| Oligo ID | Cortex (rostral) | Striatum (rostral) | Cortex (caudal) | Striatum (caudal) |
|---|---|---|---|---|
| 387985 | 17 | 23 | 37 | 16 |
| 489352 | 14 | 12 | 28 | 10 |
| 489356 | 0 | 0 | 0 | 0 |
| 489357 | 0 | 0 | 21 | 0 |

Evaluation of Toxicity Due to Antisense Oligonucleotide Administration in Brain Sections The rostral and caudal regions of striatal and cortical tissues of the brain were also individually stained with immunofluorescent antibodies rabbit anti-GFAP (Dako Inc, CA) or anti-NeuN (Chemicon Inc). Images of the stained sections were acquired using a microarray scanner (Agilent Technologies, CA). Immunofluorescent intensity was quantified using ImageJ (NIH). The results of the quantification are presented in Tables 14 and 15. Table 14 shows the levels of glial fibrillary acidic protein (GFAP), which is moderately increased in a non-specific manner as a result of antisense oligonucleotide administration. This is an expected outcome (Chiasson et al., *Cell. Mol. Neurobiol.* 1994. 14: 507-521) and the results demonstrate that the increase is non-significant. Table 15 presents the data on NeuN, a neuron marker that indicates neuronal toxicity. The results indicate none of the ISIS oligonucleotides induced increase in NeuN levels relative to the PBS control.

The brain sections were separately stained with rabbit anti-Iba1 (Wako Chem. Inc, CA) to detect microglial cells, followed by probing with a biotinylated secondary antibody. The sections were developed using a complex of avidin-biotin peroxidase. The sections were then developed by DAB substrate. The optical fractionator function of Stereo Investigator (MicroBrightField) was used to count 4 representative samples of Iba1-positive microglial cells in the striatum and cortex. The microglia were then scored as either resting or activated microglia. The scoring was based on morphological criteria of either ramified (resting) or amoeboid (activated) appearance. Activated microglia are a marker of neuronal toxicity. The average of the results was expressed as a percent of the number of activated Iba1-positive cells compared to the total number of Iba1-positive cells. The results are presented in Table 18, and demonstrate that treatment with either ISIS 387985 or ISIS 489357 does not cause microglial activation. Hence, treatment with either antisense oligonucleotide did not cause any neural toxicity.

TABLE 14

Percent increase in GFAP levels in Thy1-aSYN mice compared to the PBS control

| Oligo ID | Cortex (caudal) | Striatum (caudal) |
|---|---|---|
| 387985 | 70 | 128 |
| 489352 | 66 | 151 |
| 489356 | 61 | 82 |
| 489357 | 120 | 130 |

TABLE 15

Percent change in NeuN levels in Thy1-aSYN mice compared to the PBS control

| Oligo ID | Cortex (caudal) | Striatum (caudal) |
|---|---|---|
| 387985 | −11 | −11 |
| 489352 | −28 | −38 |
| 489356 | −5 | −1 |
| 489357 | −10 | −15 |

TABLE 16

Percent of activated microglia in Thy1-aSYN mice

| | Cortex | Striatum |
|---|---|---|
| PBS | 7 | 19 |
| ISIS 387985 | 26 | 27 |
| ISIS 489352 | 43 | 49 |
| ISIS 489356 | 35 | 66 |
| ISIS 489357 | 21 | 37 |

Example 9: Potency of Antisense Oligonucleotides Targeting Human SNCA in a Transgenic Mouse Model (Thy1-aSYN Mice)

Some of the ISIS oligonucleotides from the study described herein in Example 5 were further evaluated in Thy1-aSYN mice, which overexpress human SNCA (Rockenstein et al., J. Neurosci. Res. 68: 568-578, 2002). ISIS 387978, ISIS 387983, ISIS 387984, and ISIS 387985 all target the transgene mRNA in Thy-aSYN mice and were tested in this model.

The target sites of the human oligonucleotides to the human mRNA sequence, SEQ ID NO: 1 (GENBANK Accession No. NM_000345.3) are presented in Table 17. Some of the human oligonucleotides are cross-reactive with mouse SNCA sequences. The greater the complementarity between the human oligonucleotide and the murine sequence, the more likely the human oligonucleotide can cross-react with the murine sequence. The target start sites of the human oligonucleotides to the murine sequence SEQ ID NO: 137 (GENBANK Accession No NM_001042451.1) are also presented in Table 17. 'n/a' indicates that the antisense oligonucleotide has more than 3 mismatches to the murine sequence.

TABLE 17

Target Start Sites of antisense oligonucleotides targeting SEQ ID NO: 1 and SEQ ID NO: 137

| Human Target Start Site | ISIS No | Murine Target Start Site | SEQ ID NO |
|---|---|---|---|
| 282 | 387978 | 318 | 16 |
| 381 | 387983 | n/a | 20 |
| 404 | 387984 | n/a | 22 |
| 444 | 387985 | 480 | 23 |

Treatment

Groups of 4 Thy1-aSYN mice each were injected with 50 µg of ISIS 387978, ISIS 387983, ISIS 387984, or ISIS 387985, administered via intrastriatal bolus injection. Mice were anesthetized with sodium pentobarbitone (66 mg/kg Nembutal in sterile 0.9% saline, i.p.). The scalps of the mice were then shaved and, following loss of the pedal reflex, mice were placed in a stereotaxic frame (David Kopf Instruments, CA). To maintain a surgical plane of anesthesia, mice were administered with isoflurane (1-2% in 100% oxygen at 0.5 L/min) via a nose cone, as required. Oxygen was administered throughout the surgery and for 30 min post-surgically. The temperature of the mice was monitored using a rectal probe thermometer (Physitemp). The scalp was sterilized using three alternating wipes of Betadine and 70% ethanol. An incision was made in the scalp and the skull surface exposed and bregma positively identified. After ensuring that the skull surface was flat, i.e. a dorsoventral (DV) deviation of <0.2 mm at bregma +/−2 mm anterior-posterior (AP), a hole was drilled in the skull at 0.5 mm AP, 2 mm medialateral (ML), relative to bregma. Each of the ISIS oligonucleotides at a concentration of 50 mg/mL in a 2 µL solution was injected unilaterally into the right striatum, using a 10 µL Hamilton syringe with a 27 gauge needle connected to a microsyringe pump controller (KD Scientific 310) at a flow rate of 0.2 µL/min. The DV coordinate was measured at 3 mm below the skull surface. The needle was left in place for a further 3 minutes after injection to allow diffusion of the solution into the brain. After slowly withdrawing the syringe, the scalp was sutured, and the mice were subcutaneously injected with 0.5 mL warm sterile PBS, to aid rehydration. The mice were placed on a warm water heat pad and monitored until they regained consciousness and mobility. A group of 4 mice was injected with PBS in a similar manner. The animals were then returned to their home cage and supplied with mashed food on the cage floor. The body weights and health of mice was monitored daily post-surgery. Mice were sacrificed 2 weeks after receiving the injection by cervical dislocation.

The brains of the mice were immediately collected and dissected. Using a coronal brain matrix, 1 mm slices of the brain were harvested for mRNA and protein extraction. A 1 mm slice immediately rostral to the injection site was taken for mRNA and a 1 mm slice immediately caudal to the injection site was taken for protein analyses. The striatum and cortex from the ipsilateral hemisphere were dissected on ice.

RNA Analysis

For mRNA purification, brain tissue was rapidly frozen on dry ice in 2 mL tubes containing 0.5 mL GITC/BME and sterile ceramic beads. RNA was extracted from the striatal and cortical tissues of the brain for real-time PCR analysis of human SNCA mRNA normalized to Cyclophilin A mRNA. Human SNCA mRNA levels were measured using human primer probe set RTS2618 (forward sequence AGACCAAAGAGCAAGTGACAAATG, designated herein as SEQ ID NO: 138; reverse sequence CCTCCACTGTCTTCTGGGCTACT, designated herein as SEQ ID NO: 139; probe sequence TGGAGGAGCAGTGGTGACGGGTG, designated as SEQ ID NO: 140). The results are presented in Table 18, expressed as percent inhibition compared to the PBS control. Mouse SNCA mRNA levels were also measured using murine primer probe set RTS2956 (forward sequence GTCATTGCACCCAATCTCCTAAG, designated herein as SEQ ID NO: 141; reverse sequence GACTGGGCACATTGGAACTGA, designated herein as SEQ ID NO: 142; probe sequence CGGCTGCTCTTCCATGGCGTACAA, designated herein as SEQ ID NO: 143). The results are presented in Table 19, expressed as percent inhibition compared to the PBS control. Since ISIS 387978 and ISIS 387985 both target SEQ ID NO: 137, treatment with either antisense oligonucleotide inhibits murine SNCA mRNA expression.

TABLE 18

Percent inhibition of human SNCA mRNA in Thy1-aSYN mice compared to the PBS control

| ISIS No | Striatum | Cortex |
|---|---|---|
| 387978 | 35 | 0 |
| 387983 | 16 | 0 |
| 387984 | 67 | 35 |
| 387985 | 89 | 70 |

TABLE 19

Percent inhibition of murine SNCA mRNA in Thy1-aSYN mice compared to the PBS control

| ISIS No | Striatum | Cortex |
|---|---|---|
| 387978 | 62 | 44 |
| 387983 | 16 | 0 |
| 387984 | 18 | 2 |
| 387985 | 84 | 83 |

Protein Analysis

Tissue samples for protein analysis were rapidly frozen in tubes containing sterile ceramic beads. Protein levels of SNCA were measured by western blot analysis using an anti-SNCA antibody (Signet, #4D6) targeting both human and murine SNCA. The results are presented in Table 20, expressed as percent inhibition compared to the PBS control.

TABLE 20

Percent inhibition of SNCA protein levels in Thy1-aSYN mice compared to the PBS control

| ISIS No | Striatum | Cortex |
|---|---|---|
| 387978 | 0 | 0 |
| 387983 | 9 | 0 |
| 387984 | 0 | 0 |
| 387985 | 29 | 76 |

Immunofluorescence Analysis

One coronal section from each brain was taken at the level of the caudal striatum. After washing in PBS, the sections were incubated in M.O.M. mouse IgG blocking reagent (Vector Laboratories, PK-2200) for 1 hour. Sections were then incubated overnight at 4° C. in 2% NGS, 0.5% Triton X-100 in PBS with primary antibodies, mouse anti-NeuN (1:500 dilution; Chemicon MAB377) and 6653Ab rabbit anti-ASO (1:3,000 dilution; ISIS Pharmaceuticals). After washing in PBS, the sections were incubated for 2 hours in 5% NGS in PBS with secondary antibodies, Cy3-conjugated goat anti-rabbit (1:250 dilution; Millipore) and Cy5-conjugated goat anti-mouse (1:250 dilution; Jackson Immunoresearch). Several sections were incubated with secondary antibodies alone, omitting primary antibody incubation, to serve as controls. After washing in PBS, sections were mounted onto glass microscope slides in water and dried overnight. Slides were scanned using a high-resolution microarray scanner (Agilent) using lasers to excite the Cy3 and Cy5 fluorochromes. The images of the scanned sections were then analyzed using ImageJ (NIH) to quantify the intensity of the immunofluorescent staining. The average intensity of staining in the striatum and cortex of the ipsilateral and contralateral hemispheres from the brains of mice receiving ASOs was calculated and compared to that of the control mice. The immunofluorescence intensity of the PBS control was considered the baseline and was arbitrarily designated as 1.00. The results are presented in Table 21 and indicate that there was negligible neuronal toxicity in most of the ISIS oligonucleotides tested.

TABLE 21

NeuN quantification by immunofluorescent intensity in the striatum and cortex

|  | Striatum | Cortex |
|---|---|---|
| PBS | 1.00 | 1.00 |
| 387978 | 0.47 | 0.85 |
| 387983 | 0.77 | 1.17 |
| 387984 | 0.78 | 1.02 |
| 387985 | 0.90 | 0.96 |

The distribution of ASO, as displayed by Ab6653 staining, was widespread throughout the ipsilateral hemisphere, including the striatum and cortex, extending along the entire rostral-caudal axis of the striatum. Other brain structures, including the globus pallidus, the rostral extent of the hippocampus and the thalamus, were also immunopositive.

Example 10: Effect on Behavior of Thy1-aSYN Mice after Administration of Antisense Oligonucleotides Targeting Human SNCA ISIS 387985, which demonstrated significant potency in the studies described above is administered to Thy1-aSYN mice. Motor function, olfaction, and spatial memory are tested in the mice.

Treatment

Groups of 16 male Thy1-aSYN mice each, 3.5 months in age, are infused ICV, using Alzet minipump model #2002 with brain infusion kit, with 50 µg/day of ISIS 387985 or with sterile PBS for 2 weeks. This is followed by 2 weeks washout, wherein the minipump is removed and mice are allowed to recover. The mice are tested behaviorally between 4.5 months and 5 months of age. The tests used to analyze behavior are a motor test, which includes a challenging beam and pole task (Fleming, S. M. et al., J Neurosci. 24: 9434-9440, 2004), an olfaction test using a buried pellet (Fleming, S. M. et al., Eur. J. Neurosci. 28: 247-256, 2008), and a spatial working memory test using novel place recognition (Magen et al., submitted). Mice are euthanized at 5 months of age. The brain and peripheral tissues are harvested for biochemical and histological analysis.

What is claimed is:

1. A compound comprising a modified oligonucleotide consisting of 12 to 30 linked nucleosides and having a nucleobase sequence comprising at least 14 contiguous nucleobases of the nucleobase sequence of SEQ ID NO: 11, wherein at least one nucleoside of the modified oligonucleotide comprises a modified sugar moiety, wherein at least one internucleoside linkage of the modified oligonucleotide is a phosphorothioate internucleoside linkage, and wherein the compound is single-stranded.

2. The compound of claim 1, wherein each internucleoside linkage of the modified oligonucleotide is a phosphorothioate internucleoside linkage.

3. The compound of claim 1, wherein at least one nucleobase of the modified oligonucleotide is a 5-methylcytosine.

4. The compound of claim 1, wherein at least one nucleoside of the modified oligonucleotide is a bicyclic nucleoside.

5. The compound of claim 4, wherein each bicyclic nucleoside comprises a sugar moiety comprising a chemical bridge between the 4' and 2' positions of the sugar, wherein each chemical bridge is independently selected from: 4'-CH(R)-O-2' and 4'-(CH$_2$)$_2$—O-2', wherein each R is independently selected from C1-C6 alkyl, H, and C1-C6 alkoxy.

6. The compound of claim 5, wherein at least one chemical bridge between the 4' and 2' positions of the sugar is 4'-CH(R)-O-2' and wherein R is independently selected from methyl, H, and —CH$_2$—O—CH$_3$—.

7. The compound of claim 6, wherein the at least one chemical bridge is 4'-CH$_2$-O-2'.

8. The compound of claim 5, wherein each bicyclic sugar comprises a 4'-CH$_2$-O-2' chemical bridge between the 4' and 2' positions of the sugar.

9. The compound of claim 1, wherein at least one nucleoside of the modified oligonucleotide comprises a modified sugar moiety comprising a 2'-O-methoxyethyl group or a 2'-O-methyl group.

10. The compound of claim 1, wherein the modified oligonucleotide comprises from 8 to 15 linked deoxyribonucleosides.

11. The compound of claim 1, wherein the modified oligonucleotide comprises 10 linked β-D-deoxyribonucleosides.

12. The compound of claim 1, wherein the modified oligonucleotide consists of 16-20 linked nucleosides.

13. The compound of claim 1, consisting of the modified oligonucleotide.

14. The compound of claim 1, wherein the compound comprises a conjugate group.

15. The compound of claim 1, wherein the modified oligonucleotide consists of 17 linked nucleosides and has a nucleobase sequence comprising 17 contiguous nucleobases of the nucleobase sequence of SEQ ID NO: 11.

16. A compound comprising a single stranded modified oligonucleotide consisting of 17 linked nucleosides and having a nucleobase sequence comprising 17 contiguous nucleobases of the nucleobase sequence of SEQ ID NO: 11, wherein
  (i) the modified oligonucleotide comprises at least one bicyclic nucleoside; and
  (ii) the modified oligonucleotide comprises at least 9 linked β-D-deoxyribonucleosides.

17. A compound of claim 16, consisting of the modified oligonucleotide.

18. The compound of claim 16, wherein each internucleoside linkage of the modified oligonucleotide is a phosphorothioate internucleoside linkage.

19. A compound of claim 16, wherein each bicyclic nucleoside comprises a sugar moiety comprising a 4'-CH$_2$-O-2' chemical bridge between the 4' and 2' positions of the sugar.

20. A compound of claim 16, wherein the modified oligonucleotide comprises at least one 5-methylcytosine.

21. A compound of claim 16, wherein the modified oligonucleotide comprises 10 linked β-D-deoxyribonucleosides.

22. A pharmaceutical composition comprising the oligomeric compound of claim 1 and a pharmaceutically acceptable diluent or carrier.

23. A pharmaceutical composition comprising the oligomeric compound of claim 18 and a pharmaceutically acceptable diluent or carrier.

24. The pharmaceutical composition of claim 23, comprising a pharmaceutically acceptable diluent, wherein the pharmaceutically acceptable diluent is phosphate buffered saline (PBS).

25. The pharmaceutical composition of claim 24, wherein the pharmaceutical composition consists essentially of the compound and phosphate buffered saline (PBS), and the compound consists of the modified oligonucleotide.

26. The pharmaceutical composition of claim 22, comprising a pharmaceutically acceptable diluent, wherein the pharmaceutically acceptable diluent is phosphate buffered saline (PBS).

\* \* \* \* \*

UNITED STATES PATENT AND TRADEMARK OFFICE
CERTIFICATE OF CORRECTION

| | | |
|---|---|---|
| PATENT NO. | : 12,043,831 B2 | Page 1 of 1 |
| APPLICATION NO. | : 17/024359 | |
| DATED | : July 23, 2024 | |
| INVENTOR(S) | : Susan M. Freier | |

It is certified that error appears in the above-identified patent and that said Letters Patent is hereby corrected as shown below:

In the Claims

Column 207, Line 10, in Claim 23: delete "claim 18" and replace it with "claim 16"

Signed and Sealed this
Seventeenth Day of September, 2024

Katherine Kelly Vidal
*Director of the United States Patent and Trademark Office*